(12) United States Patent  
Smith et al.

(10) Patent No.: US 7,985,241 B2  
(45) Date of Patent: Jul. 26, 2011

(54) SURGICAL FASTENER

(75) Inventors: Kevin W. Smith, Coral Gables, FL (US); Juergen A. Kortenbach, Miami Springs, FL (US); Robert Sixto, Jr., Miami, FL (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 783 days.

(21) Appl. No.: 11/931,351

(22) Filed: Oct. 31, 2007

(65) Prior Publication Data

US 2008/0147116 A1  Jun. 19, 2008

Related U.S. Application Data

(60) Division of application No. 10/846,898, filed on May 13, 2004, and a continuation-in-part of application No. 10/252,069, filed on Sep. 20, 2002, now Pat. No. 6,966,919, and a continuation-in-part of application No. 10/252,078, filed on Sep. 20, 2002, now Pat. No. 7,678,122, and a continuation-in-part of application No. 10/252,079, filed on Sep. 20, 2002, now Pat. No. 7,033,378.

(60) Provisional application No. 60/496,061, filed on Aug. 18, 2003, provisional application No. 60/505,008, filed on Sep. 22, 2003, provisional application No. 60/517,724, filed on Nov. 6, 2003.

(51) Int. Cl.  
*A61B 17/04* (2006.01)

(52) U.S. Cl. .......................... 606/220; 606/151; 606/219

(58) Field of Classification Search .......... 606/151–158, 606/219–221, 300, 302, 303, 310–312, 314; 24/331, 334, 499, 500  
See application file for complete search history.

(56) References Cited

U.S. PATENT DOCUMENTS

| | | |
|---|---|---|
| 0,065,407 A | 6/1867 | Lusk, Jr. |
| 2,108,206 A | 2/1938 | Meeker |
| 3,551,987 A | 1/1971 | Wilkinson |
| 3,814,104 A | 6/1974 | Irnich |
| 4,060,089 A | 11/1977 | Noiles |
| 4,060,897 A | 12/1977 | Greenstein |
| 4,402,445 A * | 9/1983 | Green .............................. 227/19 |

(Continued)

FOREIGN PATENT DOCUMENTS

DE   100 13 927   9/2001

(Continued)

*Primary Examiner* — Darwin P Erezo  
(74) *Attorney, Agent, or Firm* — Mayback & Hoffman, P.A.; Gregory L. Mayback; Rebecca A. Tie

(57) ABSTRACT

A surgical fastener with a safety position includes a lower base having piercing posts each having fixed and coupling ends, first and second base portions respectively attached to the posts, a hinge coupling the base portions, and a bias device imparting force on at least one base portion toward the other and at an angle to the hinge axis. Also provided is an upper fastening portion receiving and selectively coupling the posts. The lower base has a piercing position for coupling with the upper fastener portion where the posts are substantially parallel and a folded position where a distance between a coupling end of the first piercing post and the coupling end of the second piercing post is less than a distance between the fixed end of the first piercing post and the fixed end of the second piercing post.

19 Claims, 84 Drawing Sheets

U.S. PATENT DOCUMENTS

| | | | |
|---|---|---|---|
| 4,416,267 A | 11/1983 | Garren | |
| 4,434,796 A * | 3/1984 | Karapetian et al. | 606/75 |
| 4,531,522 A * | 7/1985 | Bedi et al. | 606/220 |
| 4,532,927 A * | 8/1985 | Miksza, Jr. | 606/220 |
| 4,534,352 A * | 8/1985 | Korthoff | 606/220 |
| 4,889,119 A * | 12/1989 | Jamiolkowski et al. | 606/220 |
| 4,935,027 A | 6/1990 | Yoon | |
| 5,009,827 A | 4/1991 | Abu-Isa et al. | |
| 5,037,433 A | 8/1991 | Wilk | |
| 5,088,979 A | 2/1992 | Filipi et al. | |
| 5,222,963 A | 6/1993 | Brinkerhoff et al. | |
| 5,254,126 A | 10/1993 | Filipi et al. | |
| 5,346,504 A | 9/1994 | Ortiz et al. | |
| 5,389,103 A | 2/1995 | Melzer et al. | |
| 5,395,030 A | 3/1995 | Kuramoto et al. | |
| 5,403,326 A | 4/1995 | Harrison et al. | |
| 5,423,857 A * | 6/1995 | Rosenman et al. | 606/219 |
| 5,433,721 A | 7/1995 | Hooven | |
| 5,465,894 A | 11/1995 | Clark et al. | |
| 5,558,665 A | 9/1996 | Kieturakis | |
| 5,571,116 A | 11/1996 | Bolanos et al. | |
| 5,573,496 A | 11/1996 | McPherson et al. | |
| 5,584,856 A | 12/1996 | Jameel | |
| 5,649,937 A | 7/1997 | Bito et al. | |
| 5,676,674 A | 10/1997 | Bolanos et al. | |
| 5,787,897 A | 8/1998 | Kieturakis | |
| 5,792,153 A | 8/1998 | Swain et al. | |
| 5,810,882 A | 9/1998 | Bolduc et al. | |
| 5,865,724 A | 2/1999 | Palmer | |
| 5,868,141 A | 2/1999 | Ellias | |
| 5,887,594 A | 3/1999 | LoCicero | |
| 5,897,562 A | 4/1999 | Bolanos et al. | |
| 5,901,895 A | 5/1999 | Heaton et al. | |
| 5,980,538 A | 11/1999 | Fuchs | |
| 5,984,932 A | 11/1999 | Yoon | |
| 6,009,877 A | 1/2000 | Edwards | |
| 6,067,990 A | 5/2000 | Kieturakis | |
| 6,074,401 A | 6/2000 | Gardiner | |
| 6,086,600 A | 7/2000 | Kortenbach | |
| 6,113,609 A | 9/2000 | Adams | |
| 6,139,563 A | 10/2000 | Cosgrove et al. | |
| 6,206,891 B1 | 3/2001 | Jamiolkowski et al. | |
| 6,206,897 B1 | 3/2001 | Jamiolkowski et al. | |
| 6,210,419 B1 | 4/2001 | Mayenberger | |
| 6,312,437 B1 | 11/2001 | Kortenbach | |
| 6,325,503 B1 | 12/2001 | McCue, Jr. et al. | |
| 6,361,540 B1 | 3/2002 | Gauderer et al. | |
| 6,387,104 B1 | 5/2002 | Pugsley, Jr. | |
| 6,394,995 B1 | 5/2002 | Solar et al. | |
| 6,461,366 B1 | 10/2002 | Seguin | |
| 6,551,328 B2 * | 4/2003 | Kortenbach | 606/139 |
| 6,574,497 B1 | 6/2003 | Pacetti | |
| 6,616,626 B2 | 9/2003 | Crank et al. | |
| 6,663,640 B2 * | 12/2003 | Kortenbach | 606/142 |
| 6,669,713 B2 | 12/2003 | Adams | |
| 6,673,100 B2 | 1/2004 | Diaz et al. | |
| 6,736,828 B1 | 5/2004 | Adams | |
| 6,790,214 B2 | 9/2004 | Kraemer | |
| 6,835,200 B2 | 12/2004 | Laufer | |
| 6,921,361 B2 | 7/2005 | Suzuki | |
| 6,966,919 B2 * | 11/2005 | Sixto et al. | 606/153 |
| 7,033,378 B2 * | 4/2006 | Smith et al. | 606/220 |
| 7,083,636 B2 * | 8/2006 | Kortenbach | 606/220 |
| 2001/0049469 A1 | 12/2001 | Kortenbach | |
| 2002/0035370 A1 | 3/2002 | Kortenbach | |
| 2002/0040226 A1 | 4/2002 | Laufer | |
| 2002/0111534 A1 | 8/2002 | Suzuki | |
| 2002/0193816 A1 | 12/2002 | Laufer et al. | |
| 2003/0055442 A1 | 3/2003 | Laufer | |
| 2003/0065340 A1 | 4/2003 | Geitz | |
| 2003/0120285 A1 | 6/2003 | Kortenbach | |
| 2003/0236536 A1 | 12/2003 | Grigoryants et al. | |
| 2004/0010271 A1 | 1/2004 | Kortenbach | |
| 2004/0087976 A1 | 5/2004 | DeVries | |
| 2004/0097986 A1 | 5/2004 | Adams | |
| 2004/0158264 A1 | 8/2004 | Adams | |
| 2004/0162568 A1 | 8/2004 | Saadat | |
| 2004/0193117 A1 | 9/2004 | Laufer | |
| 2004/0193184 A1 | 9/2004 | Laufer | |
| 2004/0193193 A1 | 9/2004 | Laufer | |
| 2004/0193194 A1 | 9/2004 | Laufer | |
| 2004/0194790 A1 | 10/2004 | Laufer | |
| 2004/0225305 A1 | 11/2004 | Ewers | |

FOREIGN PATENT DOCUMENTS

| | | |
|---|---|---|
| EP | 0 095 249 | 11/1983 |
| EP | 0 480 428 | 4/1992 |
| EP | 0 576 265 | 12/1993 |
| EP | 0 646 356 | 4/1995 |
| EP | 1 277 442 | 1/2003 |
| EP | 1 447 052 | 8/2004 |
| EP | 1 452 125 | 9/2004 |
| GB | 2 128 478 | 5/1984 |
| WO | 99 22649 | 5/1999 |
| WO | 01 85034 | 11/2001 |
| WO | 02 24080 | 3/2002 |
| WO | 02 094105 | 11/2002 |
| WO | 03 090633 | 11/2003 |
| WO | 2004 019787 | 3/2004 |
| WO | 2004 019788 | 3/2004 |

* cited by examiner

SURGICAL FASTENER

CROSS-REFERENCE TO RELATED APPLICATIONS

This application claims is a divisional of co-pending U.S. patent application Ser. No. 10/846,898, filed May 13, 2004, which application:
- claims the benefit of U.S. Provisional Patent Application Ser. Nos. 60/496,061, filed Aug. 18, 2003, 60/505,008, filed Sep. 22, 2003, and 60/517,724, filed Nov. 6, 2003; and
- is a continuation in part of U.S. patent application Ser. Nos. 10/252,069, filed Sep. 20, 2002, now U.S. Pat. No. 6,966,919; 10/252,078, filed Sep. 20, 2002, now U.S. Pat. Nos. 7,678,122; and 10/252,079, filed Sep. 20, 2002, now U.S. Pat. No. 7,033,378; the complete disclosures of which are each hereby incorporated by reference herein in their entirety.

BACKGROUND OF THE INVENTION

1. Field of the Invention

The invention relates to surgical fasteners, endoscopic surgical instruments, and procedures. More particularly, the invention relates to surgical fasteners, endoscopic instruments, and procedures for the transoral plication and fastening together of portions of the stomach for the treatment of GERD.

2. State of the Art

Gastroesophageal reflux disease (GERD) or persistent heartburn is caused by an improper relaxation of the lower esophageal sphincter (LES) that allows the frequent regurgitation of acidic stomach contents into the esophagus. If left untreated, chronic reflux may cause esophageal stricture, bleeding ulcers, perforation, and scarring. Continued reflux may lead to Barrett's esophagus, which involves changes in the cells that make up the esophagus and may lead to cancer.

The current mode of treatment is primarily pharmacological starting with antacids and progressing to proton pump inhibitors (PPIs). The progression of the disease is noted by the development of a hiatal hernia caused by the stomach being forced into the thoracic cavity. The pharmacological treatment ends with double and triple dosing of PPIs. At the point that the patient is not responding to the PPIs, surgical intervention is often recommended.

The current standard for surgery is the Nissen fundoplication. The fundoplication procedure involves wrapping the fundus of the stomach around the lower end of the esophagus and fastening it in place to make the lower esophageal sphincter less compilable. Traditionally, this procedure is accomplished through open surgery with the use of sutures to secure the plicated fundus of the stomach around the esophagus without penetrating (incising) the stomach. However, with the advent of laparoscopic surgery came the development of a corresponding laparoscopic Nissen procedure.

In an effort to further reduce the invasiveness of treatment for GERD, endoscopic techniques are being explored. Techniques that are currently under trials include the implantation of bulking agents, cautery techniques to produce scarring, and suturing or otherwise fastening internal tissue.

For example, U.S. Pat. No. 5,403,326 to Harrison et al. (hereinafter referred to as "Harrison") discloses a method of performing endoscopic fundoplication using surgical staples or two-part surgical fasteners. The procedure disclosed by Harrison involves performing two percutaneous endoscopic gastrotomies (incisions through the skin into the stomach) and the installation of two ports through which a stapler, an endoscope, and an esophageal manipulator (invagination device) are inserted. Under view of the endoscope, the esophageal manipulator is used to pull the interior of the esophagus into the stomach. When the esophagus is in position, with the fundus of the stomach plicated, the stapler is moved into position around the lower end of the esophagus and the plicated fundus is stapled to the esophagus. The process is repeated at different axial and rotary positions until the desired fundoplication is achieved. While, the procedure disclosed by Harrison is a vast improvement over open surgery, it is still relatively invasive, requiring two incisions through the stomach.

U.S. Pat. No. 5,571,116 to Bolanos et al. (hereinafter referred to as "Bolanos") discloses a non-invasive treatment of gastroesophageal reflux disease that utilizes a remotely operable invagination device and a remotely operable surgical stapler, both of which are inserted transorally through the esophagus. According to the methods disclosed by Bolanos, the invagination device is inserted first and is used to clamp the gastroesophageal junction. The device is, then, moved distally, pulling the clamped gastroesophageal junction into the stomach, thereby invaginating the junction and involuting the surrounding fundic wall. The stapler is, then, inserted transorally and delivered to the invaginated junction where it is used to staple the fundic wall.

Bolanos discloses several different invagination devices and several different staplers. Generally, each of the staplers disclosed by Bolanos has an elongate body and a spring biased anvil that is rotatable approximately 15 degrees away from the body in order to locate the invaginated gastroesophageal junction between the body and the anvil. The body contains a staple cartridge holding a plurality of staples, and a staple-firing knife. Each of the invagination devices disclosed by Bolanos has a jaw member that is rotatable by at least 45 degrees and, in some cases, more than 90 degrees to an open position for grasping the gastroesophageal junction. One of the chief disadvantages of the methods and apparatus disclosed by Bolanos is that the stapler and the invagination device are separately inserted but must both be present in the esophagus at the same time. With some of the embodiments disclosed, the presence of both instruments is significantly challenged by the size of the esophagus. Moreover, the esophagus cannot form a seal about both the instruments and, thus, it is difficult to insufflate the stomach to facilitate the procedure. In addition, the actuating mechanism of the device disclosed by Bolanos is awkward. In particular, the stapler anvil is biased to the open position, and it is not clear whether or not the stapler anvil can be locked in a closed position without continuously holding down a lever. In addition, it appears that the staple-firing trigger can be operated inadvertently before the anvil is in the closed position, which would result in inadvertent ejection of staples into the stomach or the esophagus of the patient.

U.S. Pat. No. 6,086,600 to Kortenbach discloses an endoscopic surgical instrument adapted to perform fundoplication between the stomach wall and the esophagus. The instrument includes a flexible tube, a grasping and fastening end effector coupled to the distal end of the tube, and a manual actuator coupled to the proximal end of the tube. The manual actuator is coupled to the end effector by a plurality of flexible cables that extend through the tube. The tube contains a lumen for receiving a manipulatable endoscope and the end effector includes a passage for for the distal end of the endoscope. The end effector has a store for a plurality of male fastener parts, a store for a plurality of female fastener parts, a rotatable grasper, a rotatable fastener head for aligning a female fastener part and a male fastener part with tissues therebetween, and a firing member for pressing a male fastener part through tissues grasped by the grasper and into a female fastener part. According to a stated preferred embodiment, the overall diameters of the flexible tube and the end effector (when rotated to the open position) do not exceed approximately 20 mm so that the instrument may be delivered transorally to the fundus of the stomach.

While transoral fundoplication devices and methods hold promise, it is still difficult to deliver and manipulate the necessary apparatus transorally. One reason for the difficulty is that the overall diameter, or more accurately the cross-sectional area, of the equipment is too large. Moreover, even if the Kortenbach device could be reduced to 20 mm in diameter (314 mm$^2$ cross sectional area), it would still be difficult to manipulate. Those skilled in the art will appreciate that larger instruments are less pliable and the plication and fastening procedure requires that the instruments be retroflexed nearly 180 degrees. Moreover, it will be appreciated that large instruments obscure the endoscopic view of the surgical site.

Recently, PCT WO 00/78227 (NDO Surgical Inc.) has disclosed a device sized to receive an endoscope and that is purportedly capable of plicating and damaging portions of the stomach wall to effect serosa-to-serosa contact that results in stomach wall tissue adhesion. As a result, compliance of the tissue about the esophagus would be reduced and a flap (i.e., valve) would be formed about the LES. For such a purpose, the plication and adhesion should, preferably, be created at the horseshoe-shaped tissue in the stomach surrounding the LES. The distance from the Z-line (esophageal/stomach borderline) to the horseshoe-shaped target tissue is approximately 1 to 3 cm into the stomach and plication at this location permits the greatest stress to be placed on the tissue about the LES. To approach plication at this location, the device has a particularly complicated and unwieldy multi-component end effector adapted to grab tissue, plicate the tissue, and fasten the tissue together. That is, while the above referenced device appears to offer a solution, it may not be practical to implement mechanically or operate during the procedure. Further, the above referenced device, while respectfully having a relatively smaller diameter than other prior art (approximately 18 mm in diameter and 254 mm$^2$ in cross-sectional area), maintains that cross-sectional area over its entire length. In addition to limited flexibility, the size of the device renders it difficult to traverse the Cricopharyngeal Junction. Moreover, while it is desirable to plicate the stomach wall in a direction parallel to the esophagus in order to satisfactorily reduce compliance of the tissue, it is noted that the end effector of the above referenced device is unable to approach the target tissue from the desired direction.

It is also preferable that any fastener used for the apposition of tissue in the stomach cavity be removable in the event of tissue ischemia, vagus nerve irritation, or continued reflux, and be relatively non-injurious to the patient should the fastener inadvertently become loose from the device or dislodged from the tissue. In addition, current fasteners are difficult to locate within the stomach through an endoscope if it becomes necessary to find the fastener for removal.

SUMMARY OF THE INVENTION

It is, therefore, a feature of the invention to provide methods and apparatus for transoral plication and fastening of tissue of the stomach wall.

It is another feature of the invention to provide an apparatus for transoral plication and fastening of tissue that is adapted to form a plication at a location substantially adjacent the lower esophageal sphincter.

It is also a feature of the invention to provide an apparatus for transoral plication and fastening of tissue that is adapted to approach the stomach tissue in a direction substantially parallel to the esophagus.

It is an additional feature of the invention to provide an apparatus that has a relatively small cross-sectional area and is adapted for transoral plication and fastening of tissue.

It is a further feature of the invention to provide an endoscopic apparatus for transoral plication and fastening of tissue that can be detached from the endoscope while the endoscope is located within the stomach.

It is a further feature of the invention to provide methods and an apparatus for transoral plication and fastening of tissue that damages tissue such that adhesion occurs during healing.

It is still another feature of the invention to provide a tissue fastener that will not cause ischemia and that, if necessary, is relatively easily endoscopically removable from the stomach.

It is yet another feature of the invention to provide a fastener that can easily be identified in the stomach with an endoscope.

It is yet a further feature of the invention to provide measures for easily identifying with an endoscope a correct clip installation position of the effector while the effector is in the stomach.

It is still a further feature of the invention to provide a fastener that, if inadvertently released into the stomach, will not cause harm to the gastrointestinal tract.

It is yet an additional feature of the invention to provide a two-part fastener that minimizes the possibility of injury to the patient should any part of the fastener become separated inadvertently from the implantation device prior to coupling, become separated after coupling, become loose and fall away from the implantation site, and/or fall away from the implantation site after the fastener is removed therefrom. For example, a male part with relatively sharp posts can have a collapsible base that orients the sharp points of the post toward one another. Alternatively, or additionally, the posts can be collapsible.

It is yet again another feature of the invention to provide a retrieval device that unlocks an implanted and locked two-part fastener and securely grasps at least one of the fastener parts to prevent inadvertent release of the part into a patient. The two-part fastener has an unlocking device cooperating with the retrieval device such that a user can easily capture the unlocking device with the retrieval device and, when captured, easily actuate the unlocking device to unlock the fastener's two parts.

It is still again a further feature of the invention to provide a method for plicating substantially larger target tissue.

In accord with these features, which will be discussed in detail below, a two-part fastener and an instrument for aligning application of the fastener to the stomach wall in a manner that effectively treats Gastroesophageal Reflux Disease are provided.

The fastener includes male and female parts that can be adjustably coupled together to define various spaces therebetween such that, depending on the amount of tissue between the components, a desired amount of force can be applied to the tissue therebetween by the fastener, i.e., such that the tissue does not necrose. The male part includes a plurality of tissue-piercing posts that are spring-biased to collapse into a base of the male part to prevent injury to the patient should the male part inadvertently become separated from its respective jaw prior to coupling with the female part or separated from the female part after coupling therewith. Other tissue-piercing post configurations are provided as well to prevent any injury if the male part inadvertently enters the patient. In addition, the female part is provided with a cover that shields the piercing tips of the posts after the male and female parts are coupled together. Covering the pins with the female part also avoids potential hazards as the device is inserted into a patient's mouth. Covering the pins limits the pins' exposure to bacteria present in the mouth and substantially prevents the possibility of piercing a fastening location (i.e., stomach wall) with a contaminated fastener The fastener, when in a fastened configuration, may be unfastened by moving portions of the cover relative to each other. Unfastening can be performed, e.g., using a snare device to lasso the device and move portions of the female part relative to each other.

The instrument includes a relatively short distal end effector that may be coupled over a portion of the endoscope, a proximal actuation handle, and a relatively small diameter control shaft extending between the handle and the end effector. As only the control shaft extends from the handle of the instrument to the end effector, during use, the cross-sectional area of the system within the esophagus at all locations other than the distal end of the instrument, is substantially small (the sum of the areas of the endoscope and the control shaft); i.e., less than half that of other proposed systems. In addition, at the distal end of the instrument, the system cross-sectional area is also smaller than that of prior art systems.

More particularly, the distal end effector may be provided with a sleeve that can be slidably positioned over the end of the endoscope and, likewise, slidably removed therefrom. Alternatively, the end effector may be coupled at the distal end of the endoscope and inserted along with the endoscope. Preferably, the end effector is inserted into the patient separately from the endoscope by being guided over a pre-inserted guide-wire. The sleeve is, preferably, proximally and distally tapered to ease insertion into and removal from the esophagus. The distal end effector also includes a clevis about which a pair of rotatable jaws is coupled. The jaws are laterally displaced relative to the control shaft. The jaws are each adapted to each hold one part of the two-part fastener. When the jaws are in a closed position with the parts of the fastener located therebetween, the jaws extend substantially parallel to the longitudinal axis of the control shaft. That is, the jaw assembly is fixed in a retroflexed or "looking back" configuration, directed 180° from the distal end of the control shaft. In addition, the jaws and fastener parts together define posts adapted to grab the stomach tissue, pierce and damage the serosa of the stomach tissue, and plicate the stomach tissue when the jaws are moved from an open position to a closed position.

The distal end effector may be provided with alignment measures to indicate visually to a user that the jaws are in the proper aligned position substantially parallel to one another for fastener implantation.

The instrument includes a first control element that moves the jaws between open and closed positions and a second control element that couples the fastener parts together and releases the fastener parts from the jaws. In another embodiment, the instrument second control element is two separate control elements that couple each of the male and female fastener parts together and release the fastener parts from the jaws when coupled.

One embodiment of using the system includes sliding the sleeve of the instrument over the distal end of the endoscope and moving the sleeve to a central location on the scope. The endoscope is, next, inserted through the esophagus and into the stomach. The distal end of the instrument, with the jaws in a closed low profile configuration, is, then, slid over the endoscope, past the Cricopharyngeal Junction, through the esophagus, into the stomach, and off the distal end of the endoscope. The endoscope may be retroflexed during a portion of the insertion of the distal end of the instrument such that the instrument insertion is performed under view of the endoscope. The instrument can be inserted on or off the endoscope.

The jaws of the instrument are, then, opened by actuation of the handle, and the handle and/or control shaft are pulled back to cause the open jaws to forcibly contact the stomach tissue surrounding the lower esophageal sphincter, i.e., the target tissue 1 cm to 3 cm into the stomach. As the jaws contact the tissue, a post on the female jaw and the posts of the male part of the fastener pierce the mucosa, deep muscle, and/or serosa of the tissue. An endoscopic grasping instrument extending through the endoscope may be used in conjunction with the end effector to aid in pulling the target tissue between the jaws. The combination of the grasping instrument and a separate, independent end effector according to the present invention gives an endoscopist the ability to employ techniques that, to date, were only available to surgeons. To illustrate this point, a brief history of Endoscopy is set forth in the following text.

The tools of Endoscopy have evolved over the last three decades. The major change has been the natural transition from rigid scopes to flexible scopes. In some areas of Endoscopy such as Urology and Gynecology, rigid scopes are in use today and are considered to be ideal for observation and numerous treatments of ailments. In every instance, the endoscopist has been confined to working in a two dimensional field, which has been due to the limited depth of field that can be operated on using an endoscope. The depth-of-field limitation is due to limitations of lighting and set focal lengths. For this reason, the tools that have been developed for Endoscopy work in line with the endoscope and work primarily within a short distance in front of the endoscope's optics. The tools also required an operating channel within the endoscope to access the area of interest.

The advances of fiber optics primarily drove the change from rigid to flexible scopes. This allowed the rigid glass rods to be replaced by flexible fibers that could carry light down to the targeted area and transmit an image back to an external camera. The fiber bundles and the channels' cross-sectional area were sufficiently large to limit the possibilities of complex tools usable by endoscopists. As a result, the kinds of devices that an endoscopist could use were limited primarily to loops, snares, biopsy forceps, needles, baskets, laser fibers, and diathermy probes. Further advancements in the field have eliminated the fiber bundle used for the optics of an endoscope and replaced it with a CCD camera disposed at the distal end of the endoscope. Operating channels have increased in diameter even though the outer diameter of the endoscope has been decreased to improve passability into a patient.

Nonetheless, some limitations remain. Devices used in endoscopy were sent to the treatment site over a pre-installed guidewire or, in some instances, blind. Other measures for visualization have been used, such as fluoroscopy, to verify placement. But, in every instance, the devices have been used in line with the endoscope, such as the dilators that are used to open strictures. Other examples include the CURON® STRETTA® probe and the NDO Surgical plicator. The CURON® device is rotated and used in various positions with respect to the endoscope, while the NDO Surgical device has a corkscrew and plicator working inline.

Optical advancements will continue with the advent of super-bright LED's and, possibly, transmitted optical signals, which can further reduce the cross-section of components that are needed to transmit light and optics back and forth to the treatment area. What has been missing is the ability of the endoscopist to operate in the third dimension, a dimension typically present in the world of surgery.

For centuries, surgeons have used two separate and independent axes to functionally impart a change to the anatomy. These axes were defined by the physicians' hands but, more recently, are defined by the placement of trocars in current laparoscopic procedures. The treatment site is, then, typically held from one coordinate axis while it is probed, cut, or cauterized from another. This technique, which is common to surgery, is novel in Endoscopy, and is so novel that the physicians need to be reminded not to lose sight of the independent device. The procedure according to the present invention was created initially for GERD, but also serves as a stepping-stone giving the endoscopist freedom and control typically reserved only for surgeons. The procedure of the present invention allows the manipulation of tissue through a working channel of an endoscope (a first coordinate axis) while the end effector, independent from the endoscope, is imparting change to the tissue (a second coordinate axis). This two-handed approach allows the greatest reduction of compliance to the gastroesophageal junction, while giving the physician the ability to verify the work prior to committing to the change made to the tissue.

With this new freedom of movement will come the ability to impart larger anatomical changes endoscopically than seen to date. The new treatment method allows improvements to current treatments of ulcers, gastric cancer, obesity, etc. With this in mind, the present invention protects the use of an independent device working in conjunction with a device that passes through the endoscope's working channel. More specifically, after the end effector and the grasping instrument are employed to place the target tissue between the jaws, the handle is actuated to cause the jaws to move into a closed position, pulling into apposition two portions of the tissue to form a plication. As the jaws are closed and the fastener is clamped about the tissue, but not locked, with the posts of the male part of the fastener extending through both layers of tissue at the ends of the plication and entering into corresponding openings in the female part. If desired, the physician can open the jaws to apply a different clamping pressure to the tissue or to entirely relocate the implanted fastener. Once the fastener is in a desired location and with a desired pressure on the tissue, and the jaws are aligned in the implantation position, the handle is actuated to lock the fastener and release the fastener from the jaws. The instrument may, then, be recoupled to the endoscope, and the endoscope and the instrument may be withdrawn from the patient.

Other instruments and methodologies that provide other couplings between the instrument and the endoscope and that do not require any coupling of the instrument to the endoscope are also provided and are set forth in the appended claims.

Although the invention is illustrated and described herein as embodied in a surgical instrument with alignment indicators, particularly for the transoral plication and fastening together of portions of the stomach for the treatment of Gastroesophageal Reflux Disease, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

The patent or application file contains at least one drawing executed in color. Copies of this patent or patent application with color drawings will be provided by the Office upon request and payment of the necessary fee.

DETAILED DESCRIPTION OF THE PREFERRED EMBODIMENTS

Figure 1:
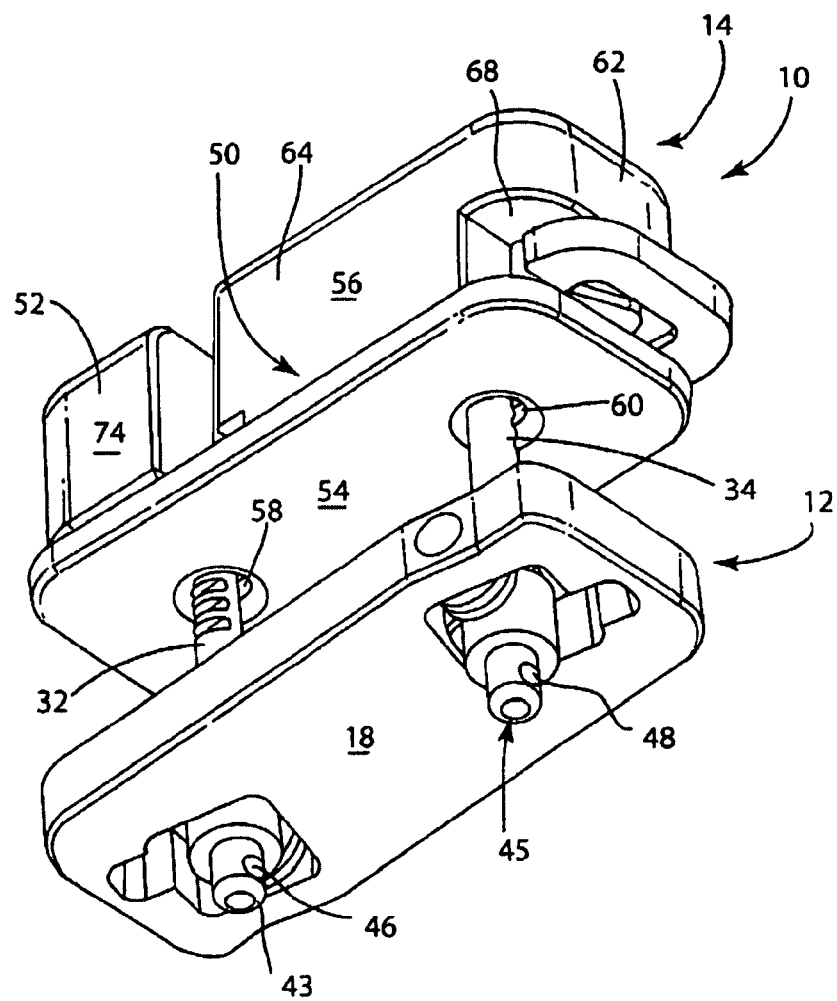
FIG. 1 is a bottom perspective view of a two-part tissue fastener according to the invention with male and female parts thereof mated but in an unlocked configuration.
Figure 2:
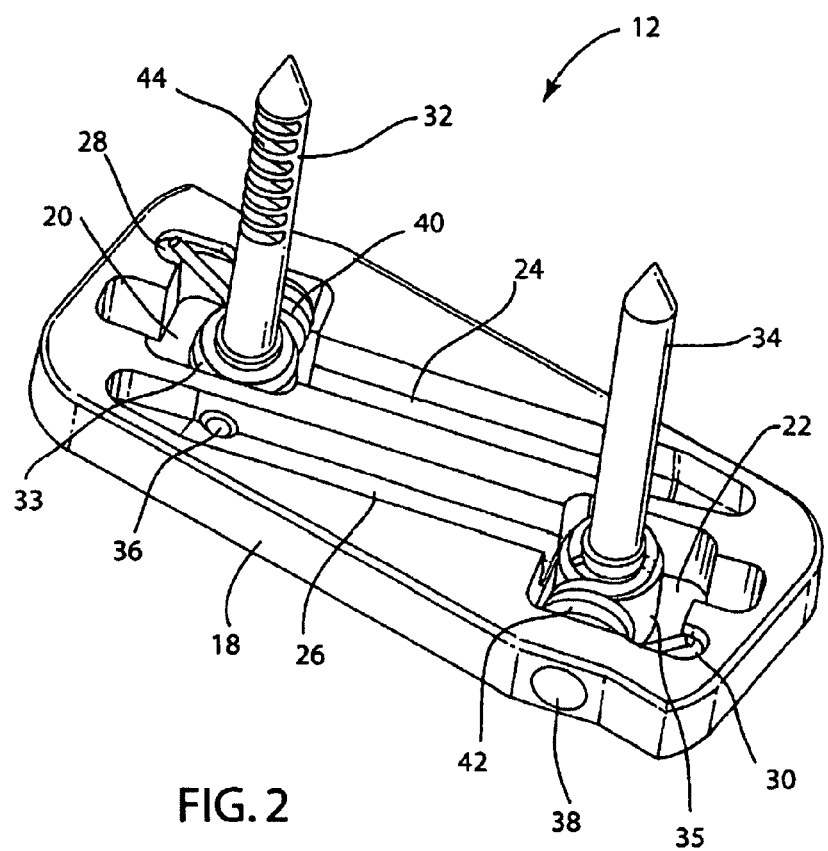
FIG. 2 is a perspective view of a male part of the fastener of FIG. 1 with posts of the male part in an upright configuration.
Figure 3:
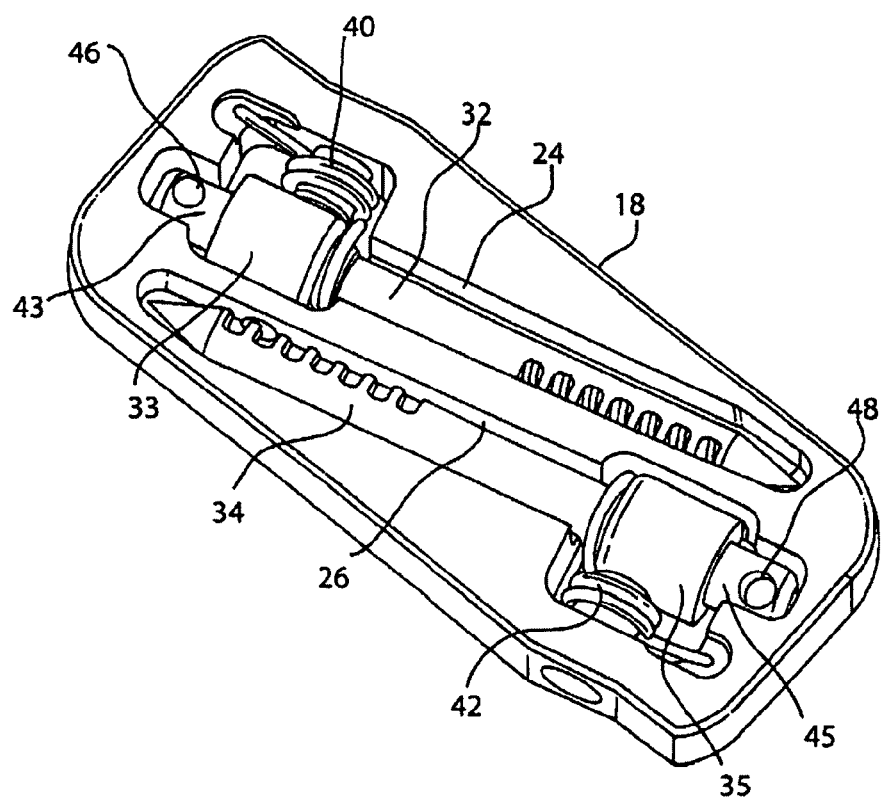
FIG. 3 is a perspective view of a male part of the fastener similar to FIG. 2 with posts of the male part in a collapsed configuration.
Figure 8:
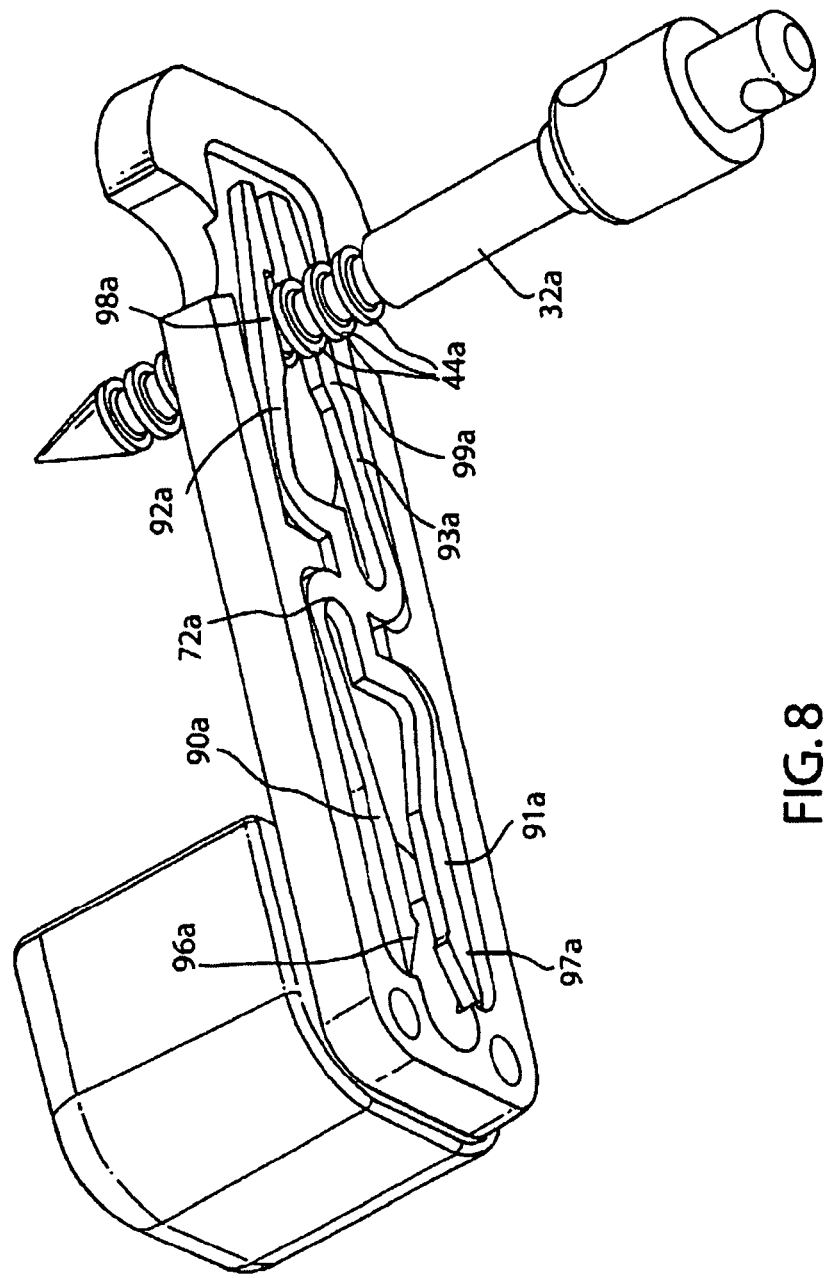
FIG. 8 is a bottom perspective view of an alternative embodiment of a post of a male part of the fastener and an alternative embodiment of the sliding assembly of the female part of FIG. 7.
Figure 9:
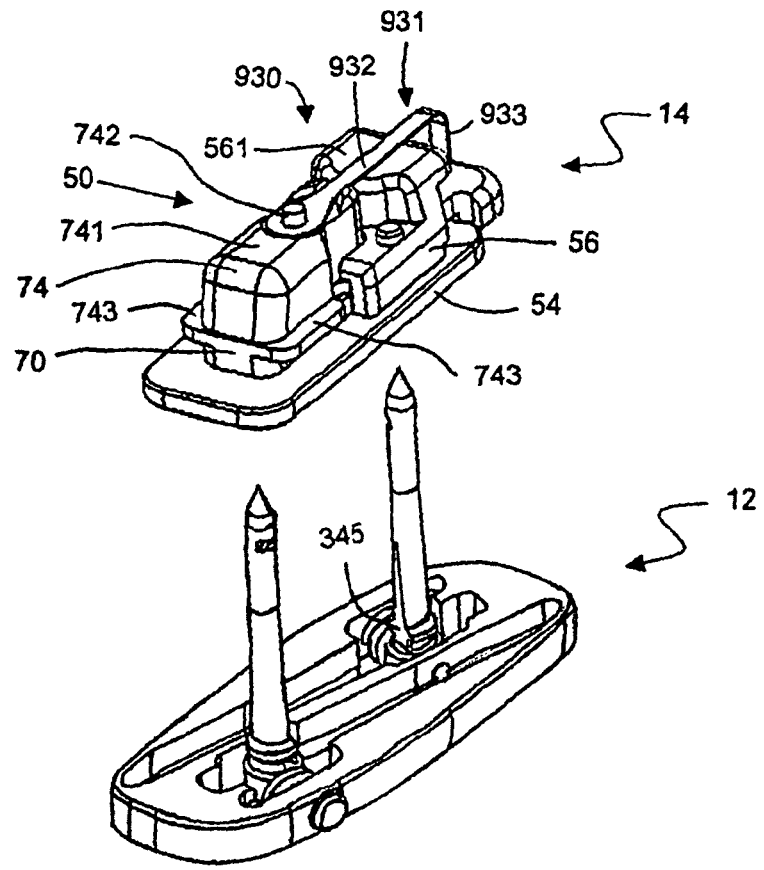
FIG. 9 is a top perspective and exploded view of an alternative embodiment of the fastener of FIG. 1 with the female part in a ready to fire position.

Referring now to the figures of the drawings in detail and first, particularly to FIG. 1 thereof, there is shown a two-part fastener 10 according to the invention. The fastener 10 includes male and female parts 12, 14. Referring to FIGS. 1 and 2, the male part 12 includes a base 18 defining two openings 20, 22 therethrough and, in one side, two elongate channels 24, 26 and two spring shelves 28, 30. Two tissue-piercing posts 32, 34 are rotatably coupled to the base 18 in alignment with the channels 24, 26. Each post includes an enlarged portion 33, 35 having a non-illustrated diametric bore. Axles 36, 38 extend across openings 20, 22, through the bores, and are press-fit into the base 18 such that the posts 32, 34 are rotatable thereabout. The posts 32, 34 have a length of, preferably, at least 15 mm such that they are adapted to penetrate the serosa of the stomach tissue, and a diameter of, preferably, no greater than 1.5 mm so that the holes made thereby in the stomach tissue are not prone to leakage. Furthermore, while the posts 32, 34 are adapted to pierce tissue, they are also slightly rounded at the tips so as to, preferably, only displace tissue rather than cut tissue. Torsion springs 40, 42 are coupled to the posts 32, 34 and are stopped against the base 18 at the shelves 28, 30. Referring to FIGS. 1 through 3, the torsion springs 40, 42 operate to bias the posts 32, 34 toward a collapsed configuration (shown, in particular, in FIG. 3) in which the posts lie within the channels 24, 26. The channels 24, 26 are oriented at an angle within the base 18 to accommodate posts 32, 34 of a maximized length for the size of the base 18. An upper portion of each post 32, 34 is provided with a plurality of slots (notches or grooves) 44 along a medial side thereof, and a lower end 43, 45 of each post is provided with a diametric bore 46, 48. In an alternative embodiment, the posts 32, 34 are tapered with a distal base thereof having a larger diameter than the tip 323, 343 and the taper ends somewhere in the middle of the post 32, 34. An example of the tapering embodiment is shown in FIGS. 8 and 9.

Figure 4:
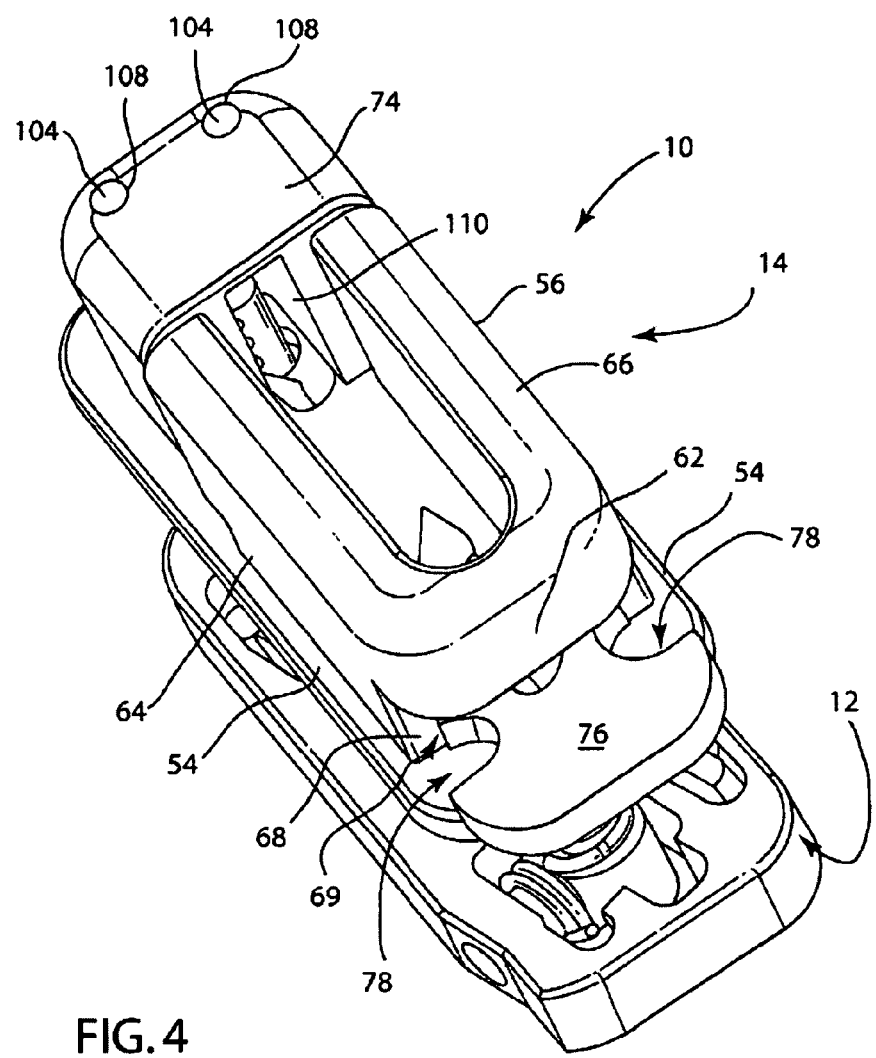
FIG. 4 is atop perspective view of the fastener of FIG. 1.
Figure 5:
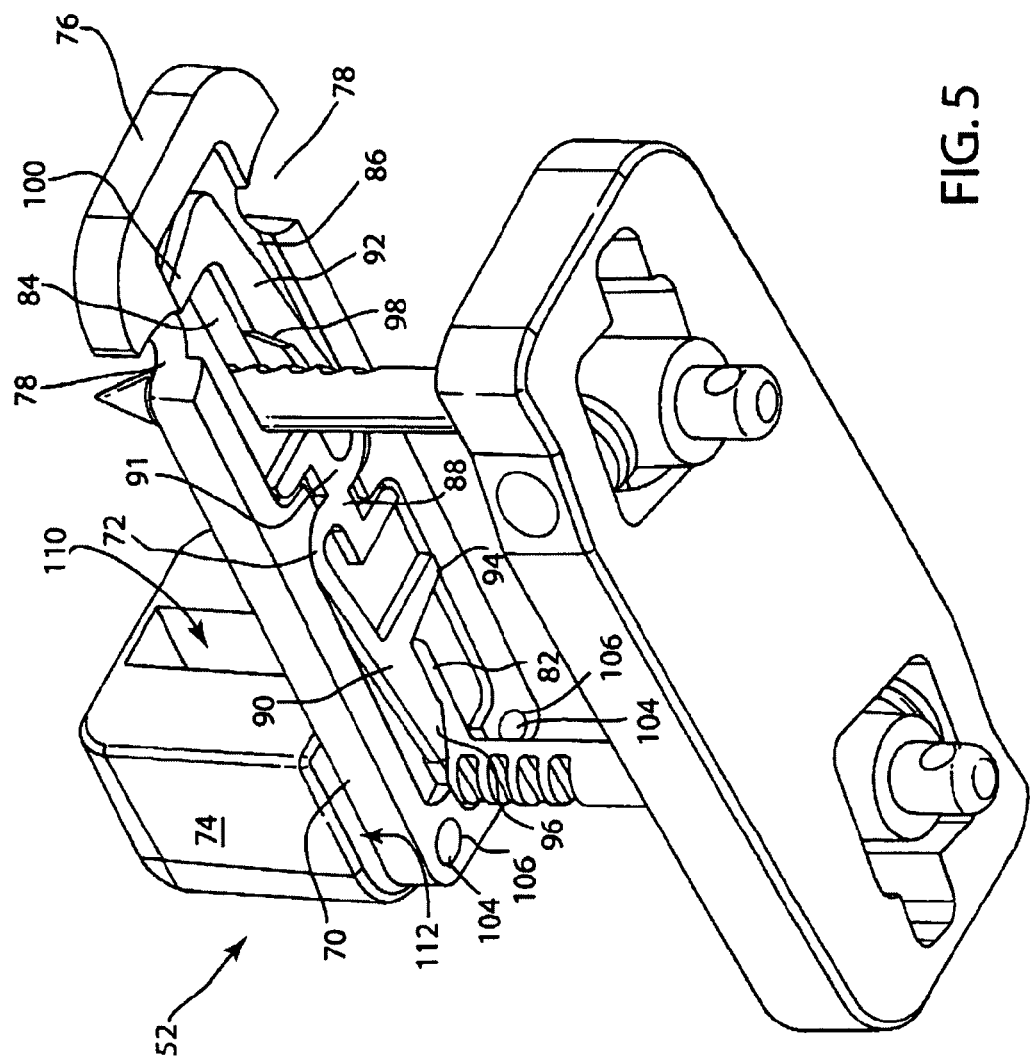
FIG. 5 is a bottom perspective view of the fastener of FIG. 1 with the latch body removed from the female part of the fastener to facilitate viewing of an interior structure of the female part.

Referring to FIGS. 1, 4, and 5, the female part 14 includes a latch body 50 and a sliding assembly 52 that is slidably movable relative to the latch body. Referring particularly to FIG. 1, the latch body 50 includes a base portion 54 and a cover (or shield) portion 56 that are manufactured as a single unit or a fixed assembly of separate elements. The base portion 54 includes two holes 58, 60, each sized to receive a post 32, 34 therethrough and, preferably, having chamfered openings. The cover portion 56 is, preferably, U-shaped, having an end portion 62 and two sides 64, 66 that extend around a portion of the periphery of the base portion 54. The end portion 62 of the cover portion 56 defines a lower recess 68 and opening 69 at the recess 68.

The sliding assembly 52 includes a latch slide 70, a latch Sock 72, and a slide cover (or shield) 74. Referring particularly to FIG. 5, the latch slide 70 defines two elongate slots 82, 84, a lower recess 86, a head portion 76 having a relatively larger width than the remainder of the slide, and cutouts 78 between the head portion 76 and the remainder of the slide. The latch lock 72 resides in recess 86 and the recess 86 is shaped to stably hold a central portion 88 of the lock 72 and to provide space for lateral displacement of elongate portions of the lock 72. More particularly, the lock 72 includes a generally Z-shaped central portion 88, and two arms 90, 92 extending from a central extension 91 of the central portion 88. Arm 90 includes a central laterally extending stop 94 and, at its terminus, a beveled catch 96. Arm 92 includes a central beveled catch 98, and at its terminus, a laterally extending stop 100. Each arm 90, 92 is biased in the direction of the extension of its stop 94, 100, with the bevel of its catch 96, 98 directed toward a respective slot 82, 84. The latch slide 70, with latch lock 72 positioned therein, is slidably inserted through the opening 69 of the cover portion 56 of the latch body 50, and the slide cover 74 is, then, fixed onto the latch slide 70 with pins 104 that are press fit into respective coupling holes 106, 108 (see FIGS. 4 and 5). It is appreciated that the latch lock 72 is retained in the recess 86 by the base portion 54 of the latch body 50. The slide cover 74 defines a central space 110. In addition, referring to FIG. 5, the latch slide 70 and slide cover 74 define a setback 112 at which the female part 14 can be engaged with an applicator instrument 200 as described in further detail below (see FIG. 26).

By way of example only, preferred dimensions for one exemplary fastener sized for being passed through the esophagus and coupling portions of the stomach tissue together are as follows. The male part 12 has a length of approximately 15 to 20 mm, a width of approximately 5 to 9 mm (in particular, 6.25 mm), and a height of approximately 1 to 3 mm (preferably, 2 mm) excluding the posts. The female part 14 has a length of approximately 12 to 18 mm (preferably, 15 mm), a width of approximately 5 to 9 mm (preferably, 6.25 mm), and a height of approximately 3 to 6 mm (preferably, 4 mm). A preferred configuration of the coupled fastener 10 has overall dimensions of a length of 18 mm, a width of 7.5 mm, and a height of 17 mm including the thickness of the tissue between the male and female parts.

The parts 12, 14 are, preferably, constructed of titanium or titanium alloy and, then, anodized according to processes known in the art of metallurgy. In an alternative process, the anodizing imparts a color distinct from the natural tissue of the stomach cavity, e.g., purple, blue, and black.

As discussed in more detail below, when the male and female parts 12, 14 of the fastener 10 are brought into apposition on opposite sides of tissue located therebetween by the below described instrument 200 (see FIG. 26) (with the posts 32, 34 of the male part 12 held upright against the bias of the torsion springs 40, 42, as detailed below), the posts 32, 34 of the male part 12 can pierce through tissue and extend into the holes 58, 60 of the base portion 54 of the female part 14 (FIG. 1).

Figure 28:
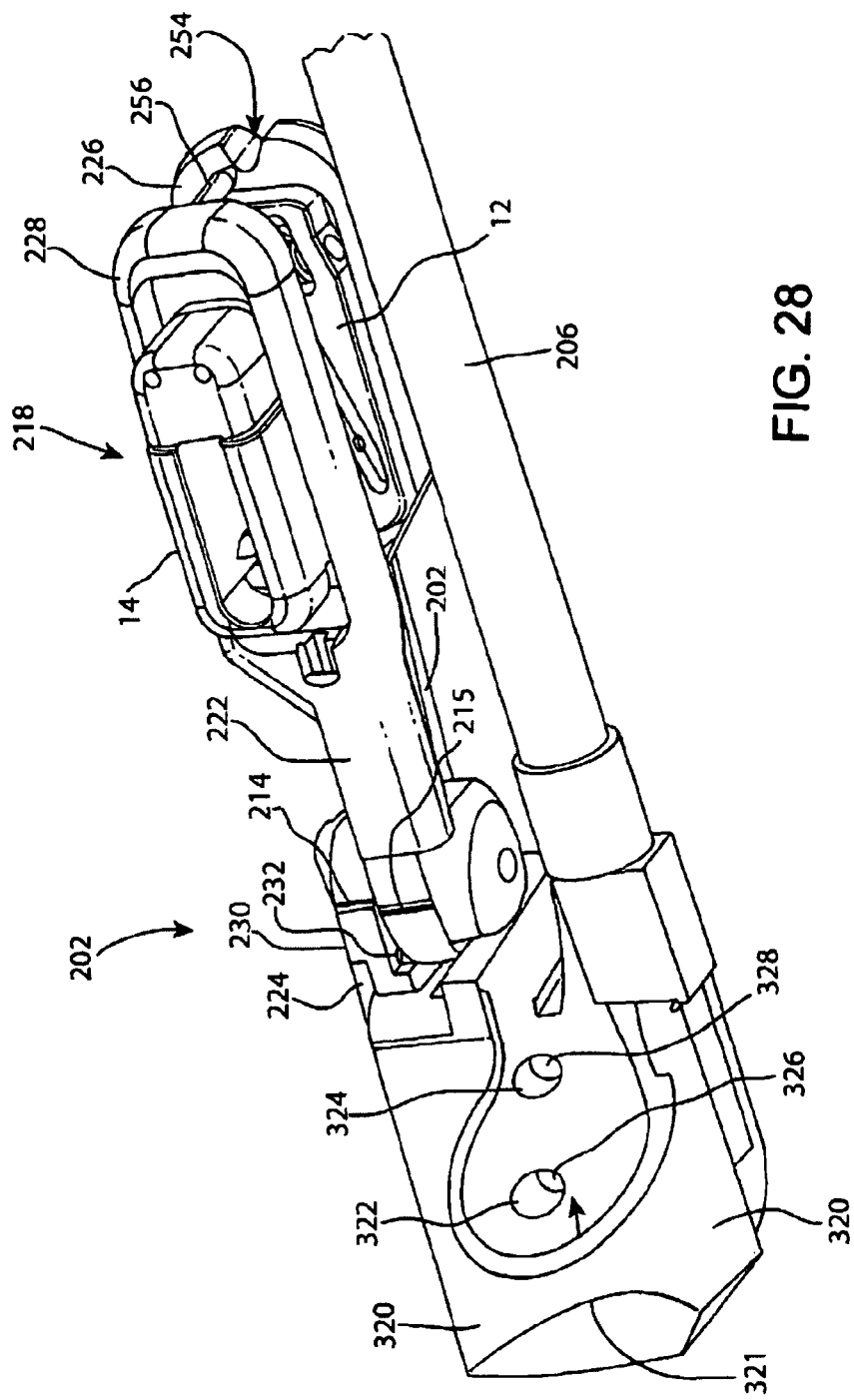
FIG. 28 is a perspective view of the distal end of the instrument of FIG. 26 from a female jaw side of the end effector.
Figure 35:
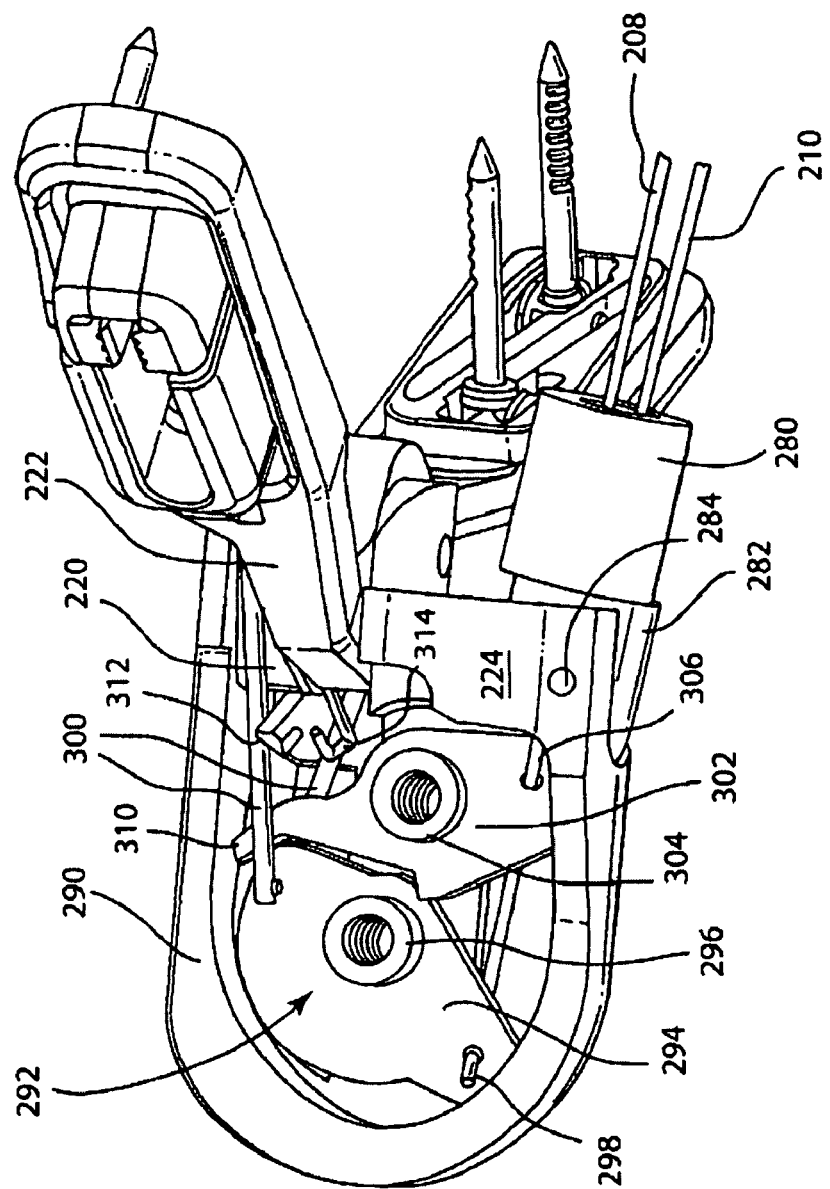
FIG. 35 is a fragmentary, perspective view of the distal end of the instrument of FIG. 30 from the female jaw side of the end effector with the mounting sleeve removed for clarity.

The chamfered openings of the holes 58, 60 (see FIG. 6) facilitate this mating by guiding the posts into the holes 58, 60 even if the parts 12, 14 are misaligned slightly. The male and female parts 12, 14 of the fastener 10 are, then, clamped about the tissue. The slide cover 74 and cover portion 56 shield the sharp portions of posts 32, 34, respectively, which extend through the base portion 54 of the female part 14. As shown in FIGS. 4, 28, and 35, a first embodiment of the cover portion 56 is open, thus, permitting access from above the female part 14 on a side opposite the male part 12. In an alternative embodiment that will be discussed below, the cover portion 56 is closed.

Figure 6:
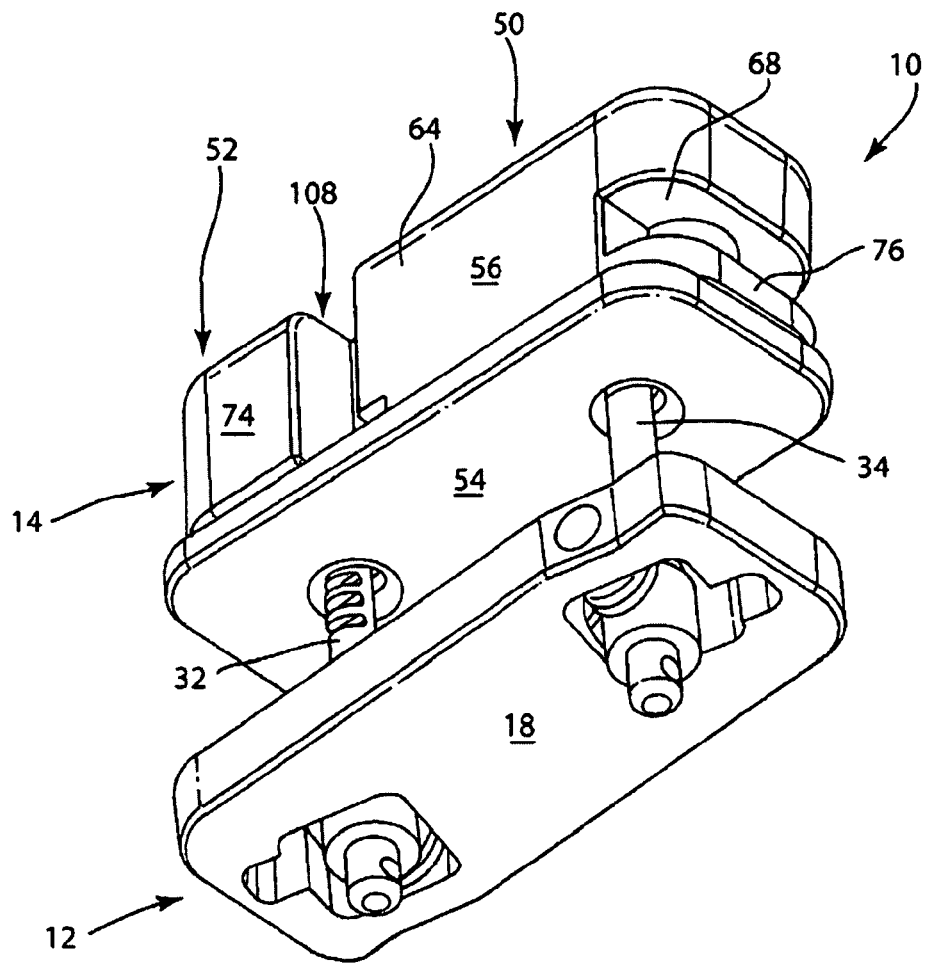
FIG. 6 is a bottom perspective view of the fastener of FIG. 1 with the male and female parts thereof mated and in a locked configuration.
Figure 7:
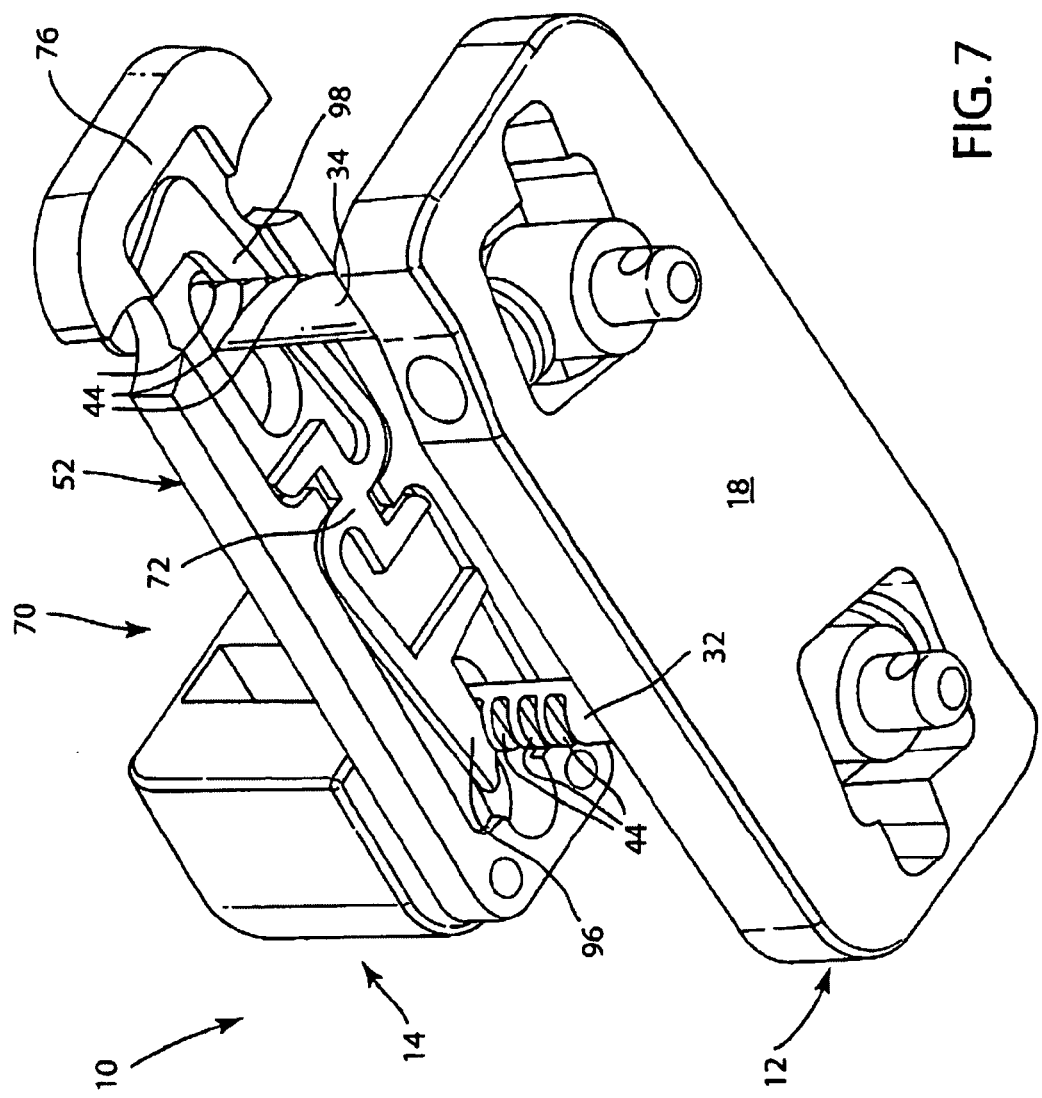
FIG. 7 is a bottom perspective view of the fastener of FIG. 6 with the latch body removed from the female part of the fastener to facilitate viewing of the interior structure of the female part.

Referring now to FIGS. 6 and 7, once the fastener 10 is clamped about tissue with a desired clamping force (or desired pressure), the sliding assembly 52 is slidable longitudinally relative to the latch body 50 until the head 76 of the latch slide 70 abuts the cover portion 56 within the recess 68 and until the catches 96, 98 on the latch lock 72 ride against their bias into respective slots 44 of the posts 32, 34, thereby locking the male and female parts 12, 14 together. In the embodiment of FIGS. 6 and 7, the plurality of slots 44 and the substantial length of the posts 32, 34 permits the base 18 of the male part 12 and base portion 54 of the female part 12, 14 to be coupled at several distances relative to each other. In addition, the base 18 and base portion 54 may even be skewed relative to each other to further accommodate various configurations of tissue therebetween, with the catches 96, 98 entering, for example, a third notch of post 32 and a fourth notch of post 34, respectively. As a result of such adjustability, a desired amount of force can be applied to tissue between the parts 12, 14, whether or not the tissue therebetween is of uniform thickness, and with such force, preferably, limited to prevent tissue necrosis. Furthermore, it is noted that when the sliding assembly 52 is moved relative to the latch body 50 but the catches 96, 98 have not engaged one of the slots 44, the catches 96, 98 will automatically find an appropriate slot 4, as the latch lock 72 is spring-loaded and compliant. That is, should a catch 96, 98 of the latch lock 72 initially contact a post 32, 34 at a non-slotted location, the compliance of the latch lock 72 will cause the catch 32, 34 to snap into an adjacent slot 44 when the male and female parts 12, 14 are subject to small relative movements.

An alternative embodiment of the posts 32, 34, as illustrated in FIG. 9, provides only one slot 44 on each post 32, 34. Such an embodiment is advantageous because, when the catches 96, 98 catch a respective slot on each of the posts 32, 34, the latched relationship guarantees a particular pre-defined spacing between the lower surface of the base portion 54 of the female part 14 and an upper surface of the base 18 of the male part 12. The defined spacing can be selected to substantially prevent the possibility of tissue necrosis therebetween. In theory, there exists a possibility for the posts 32, 34 to be inserted into the female part a distance that is insufficient to catch the single slot 44 with either of the catches 96, 98. If the male and female parts 12, 14 were allowed to be implanted with such an orientation, reliable fastening would not occur. Various features of the present invention (discussed below) eliminate the possibility of improper locking of the male and female parts 12, 14.

One such feature relates to the preferred configuration of the upper surface of the cover portion 56. The first embodiment of the cover portion 56 shown in FIG. 4 has an upper surface that is open to the environment. Such an opening creates a cavity in which any kind of foreign matter can enter (including bacteria picked up when passing through the patient's mouth). Accordingly, there exists the possibility of damage to or malfunction of the fastener 10 if foreign matter entered the cavity. In contrast to the open top surface of cover portion 56 shown in FIG. 4, a removal assembly 930 shown in FIGS. 9 to 12 provides the cover portion 56 with a closed top surface 561. Such a configuration eliminates the possibility of foreign matter entering the cover portion 56. More significantly, however, is the fact that the top surface of the cover portion 56, along with the top surface of the slide cover 74, respectively provide a stopping surface limiting the extent to which the posts 32, 34 are introduced into the interiors of the cover portion 56 and the slide cover 74. This stopping surface is defined to be a bottom-out of the posts 32, 34 and is selected such that when the distal-most tips of the posts 32, 34 contact the respective stopping surface, the single slot 44 is positioned further into the internal cavities of the cover portion 56 and the slide cover 74 than the catches 96, 98. In other words, the greatest force imparted upon the male and female parts 12, 14 to lock them together will only permit the posts 32, 34 to enter the internal cavities of the cover portion 56 and the slide cover 74 to such an extent that the two slots 44 of the posts 32, 34 move past the catches 96, 98. Thus, when the sliding assembly 52 is moved relative to the latch body 50 and one or both of the catches 96, 98 of the latch lock 72 initially contact a post 32, 34 at a non-slotted location below the slots 44, the spring load of the latch lock 72, along with the oppositely-directed pressure caused by expansion of the plicated tissue between the two parts 12, 14, for example, will cause each catch 96, 98 to snap into the respective slot 44 when the implanted fastener 10 is allowed to settle. Preferably, when the catches 96, 98 lock into the respective slot 44, a distance between a bottom surface of the base portion 54 of the female part and a top surface of the base 18 of the male part 12 is between approximately 2 mm and 20 mm.

It is recognized that various other configurations for locking the latch lock 72 of the female part 14 relative to the posts 32, 34 of the male part 12 can be used. For example, referring to FIG. 8, the posts 32a may be provided with circumferential grooves 44a. And, the latch lock 72a may have another configuration that effectively provides a catch that can be locked within the grooves 44a. In FIG. 8, the latch lock 72a includes, for post 32a, two resilient, spaced-apart, spring-biased arms 92a, 93a, each with a catch 98a, 99a adapted to engage within a groove on the post 32a and, for the second post (not shown), two resilient, spaced-apart, spring-biased arms 90a, 91a each with a catch 96a, 97a adapted to engage within a groove on the post.

It is also noted that the movement of the sliding assembly 52 relative to the latch body 50 causes the slide cover 74 to be spaced apart from the latch body cover 56. This opens a space 108 between the slide cover 74 and the latch body cover 56. (Compare FIG. 1 to FIG. 6 and FIG. 9 to FIG. 10.)

The male and female parts 12, 14 may be unlocked from each other even after the male and female parts 12, 14 have been locked together. Moving the sliding assembly 52 in an opposite direction relative to latch body 54, such that the slide cover 74 and cover portion 56 are moved relatively closer together, operates to unlock the male and female parts 12, 14 so that they may, then, be separated from each other. That is, such a mechanism facilitates decoupling of a fastener and, thereby, permits atraumatic retrieval of an implanted fastener.

One manner of effecting the decoupling can be performed with a standard endoscopic snare device found in any endoscopy suite. A loop of such a snare device (not illustrated herein) is provided over and about the cover portion 56 and the slide cover 74 and the two parts 56, 74 are pulled toward each other by decreasing the size of the snare loop. A portion of the snare loop may be positioned through recess 68 to prevent the loop from slipping off the fastener 10. It is noted that the unnatural color of the fastener 10 relative to the tissue of the stomach cavity facilitates endoscopically locating an implanted fastener for such retrieval. However, a standard snare device typically does not have the ability to generate the force necessary to reverse the sliding lock of the fastener 10 and ensure a reliable unlocking procedure.

In-vitro and in-vivo testing revealed that, although the fastener 10 could be removed using a snare system, the level of expertise required to lasso the fastener 10 was moderate to high. Further, while removal of the fastener with a snare device is possible, the time for such removal can be unacceptable. Moreover, reversing a plication formed endoscopically is not straightforward. For these reasons, along with the level of anxiety expected once a decision has been made to remove an implanted fastener 10, ease of removal becomes an advantageous and important feature. Also, the direction in which a standard loop snare applies force is not optimal. Specifically, force is applied at the proximal actuating device to withdraw the loop into the tube connecting the snare loop to the proximal actuating device. The force imparted is, however, substantially absorbed by the approx. 90° bend that the snare makes as it exits the tube and surrounds the two parts 56, 74. Accordingly, a substantial amount of force is required to close the snare, which force increases as the loop tightens.

Figure 10:
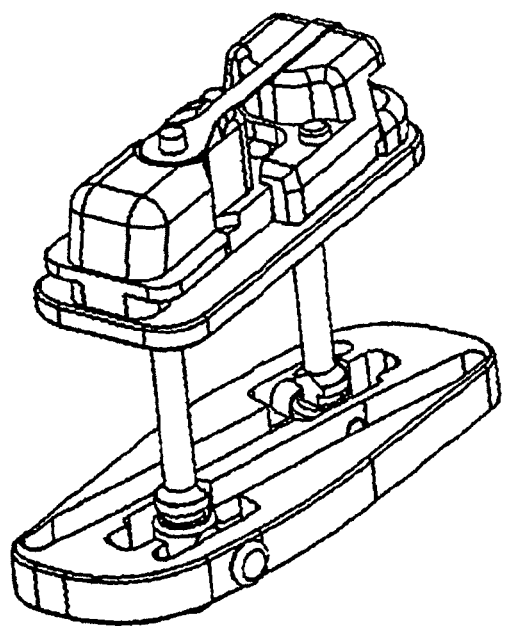
FIG. 10 is a top perspective view of the fastener of FIG. 9 with the male and female parts in a fired and locked position.
Figure 11:
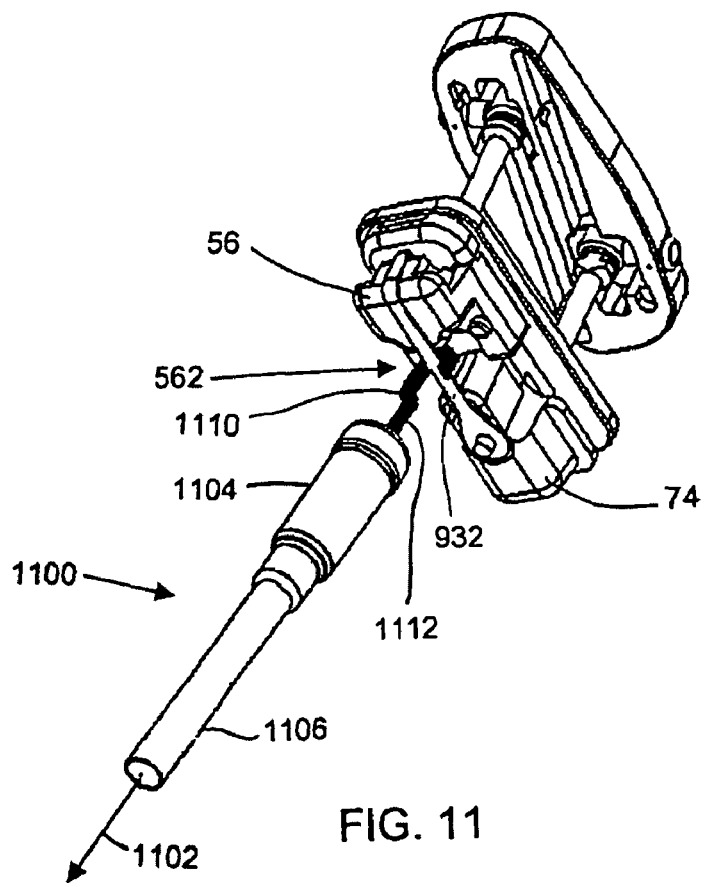
FIG. 11 is a top perspective view of the fastener of FIG. 10 with a hook of a retrieval device according to the invention in a first capture position of a releasing strap of the female part.
Figure 12:
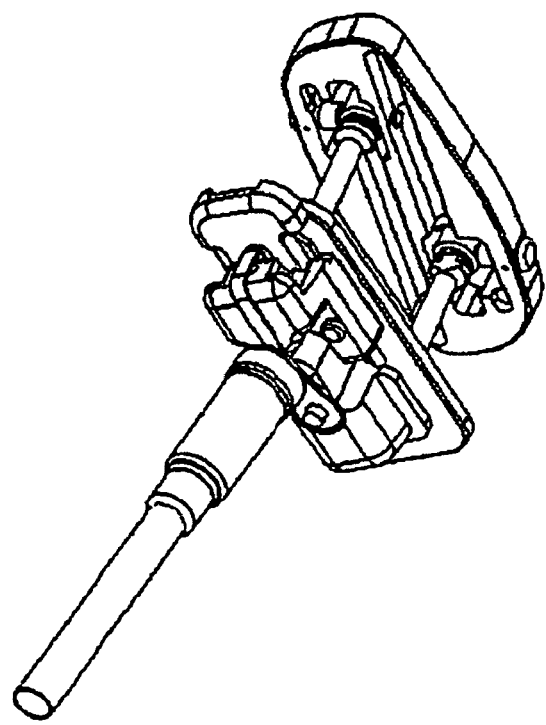
FIG. 12 is a top perspective view of the fastener of FIG. 11 with the hook of the retrieval device in a second unlocking position of the releasing strap.

The preferred way to effect a decoupling of the fastener 10 includes a removal assembly 930 on the female part 14 of the fastener 10, shown in FIGS. 9 to 12, and a separate retrieval device 1100, which is illustrated in FIGS. 11 and 12. The removal assembly 930 and the retrieval device 1100 produce the necessary force in the appropriate direction to cause the unlocking of the device, typically, in less than five minutes.

FIG. 11 illustrates the fastener 10 in a locked position with a grapple 1110 of the retrieval device 1100 just after it has engaged a release strap 931 of the female part 14 of the fastener 10. To grasp the strap 931 the grapple 1110 may be extended several inches (including some of an actuation wire 1112), for example, from a cowling 1104. The grapple 1110 is smoothly rotatable, allowing easy manipulation and placement. In FIG. 12, the grapple 1110 is in the cowling 1104 and, further retraction therein, in turn, shortens the release, strap 931 to unlock the fastener parts 12, 14.

As set forth above, the latch body 50 of the female part 14 has a base portion 54 and a cover portion 56 that are fixed to one another or are integral. The latch body 50 also includes a latch slide 70 and a slide cover 74 fixed to the latch slide 70. The latch slide 70 is mounted in a movable manner to slide upon the base portion 54 and next to the cover portion 56. The sliding relationship is illustrated, for example, in FIGS. 9 and 10, in which the slide 70 is closer to the cover portion 56 in FIG. 9 (the "ready-to-fire" position) and is further from the cover portion 56 in FIG. 10 (the "fired-and-locked" position). Even if the posts 32, 34 are properly positioned within the holes 58, 60 of the base portion 54 of the female part 14, only movement of the slide 70 away from the cover portion 56 effects a locking of the female part 14 to the posts 32, 34 of the male part 12.

The difference between removal with the preferred embodiment of the removal assembly 930 of FIGS. 9 to 13 and removal with a standard loop snare that can be used with the fastener of FIGS. 1 and 4 to 8 is the presence of a flexible member 931, such as a solid wire, a twisted cable, a suture (e.g., steel, monofilament, braided), a band, or other flexible component, particularly, in the form of a metal band or strap 931 that is a thin, flexible, and/or malleable piece of titanium.

The band 931 is fixedly attached to either side of locking mechanism, in particular, to either one or both of the base portion 54 and the cover portion 56 and to either one or both of the slide 70 and the slide cover 74.

Figure 13:
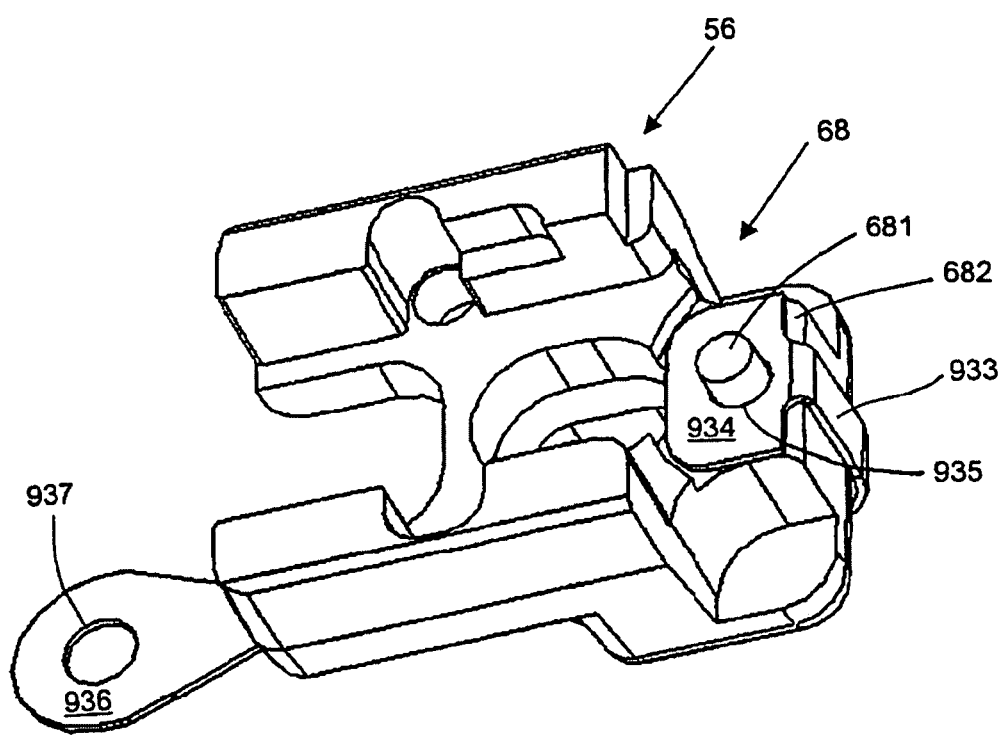
FIG. 13 is a bottom perspective view of a cover portion and an unfastening band of the female part of the fastener of FIG. 9.
Figure 14:
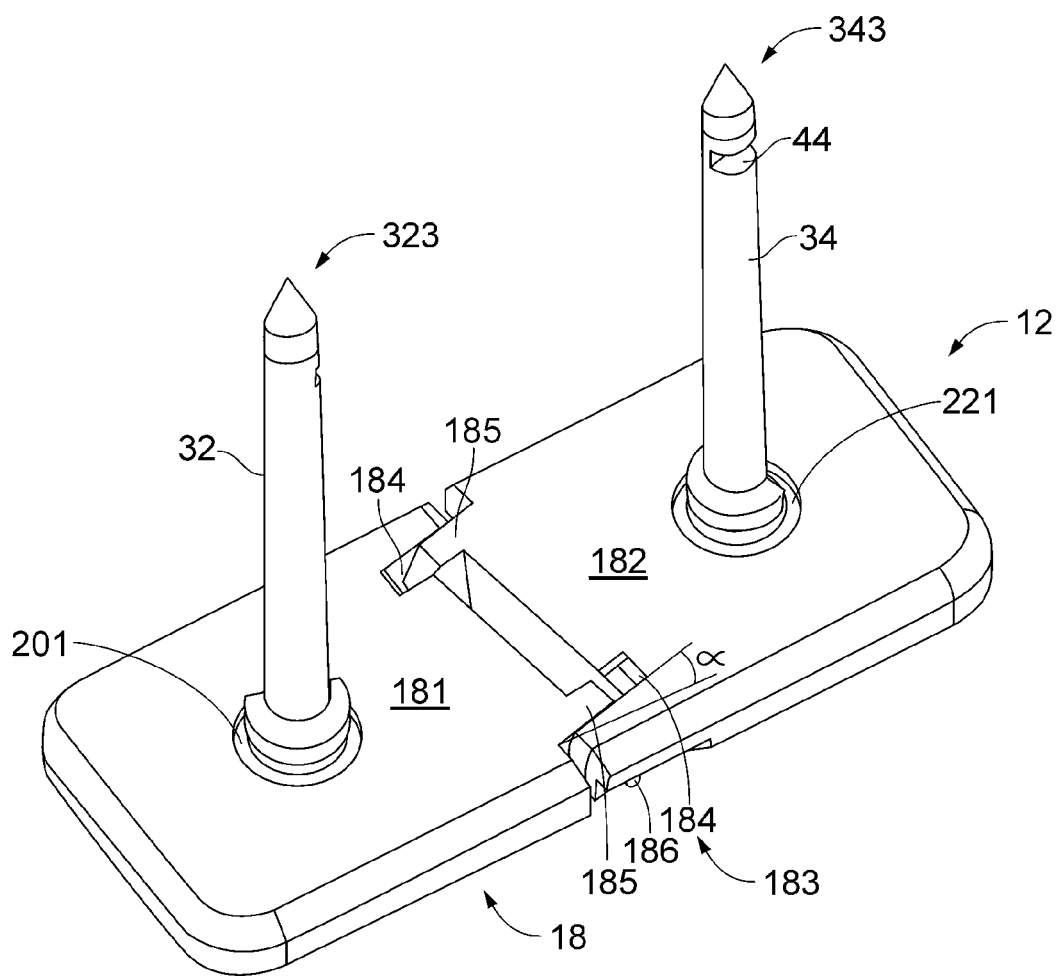
FIG. 14 is a top perspective view of an alternative embodiment of the male part of FIG. 2.
Figure 15:
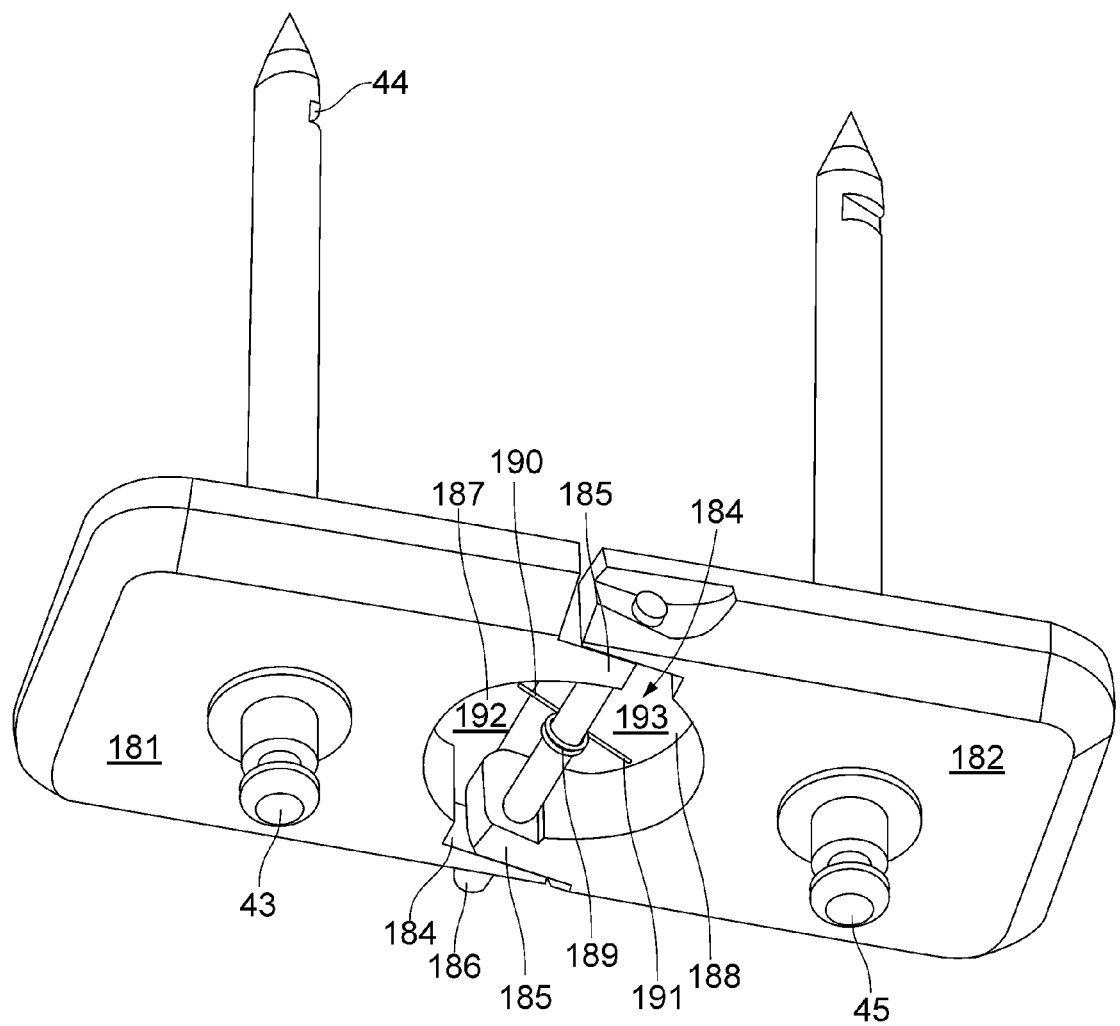
FIG. 15 is a bottom perspective view of the male part of FIG. 14.

In the preferred embodiment, the band 931 is J-shaped in cross-section, has an upper portion 932, a middle portion 933 (see FIG. 9), and a lower portion 934 (see FIG. 13), and is connected to the cover portion 56 and to the slide cover 74. With respect to the connection with the cover portion 56, the band 931 is attached inside the lower recess 68. Such a connection is best illustrated in FIG. 13, which shows an enlarged view of the cover portion 56 entirely removed from the female part 14 and turned upside-down. The lower recess 68 has a lower catch or boss 681 projecting away from the ceiling 682 of the lower recess 68. A lower bore 935, defined by the lower portion 934 of the band 931, has a shape substantially corresponding to an outer shape of the lower catch 681. The other end of the band 931 is attached to the top surface 741 of the slide cover 74. To effect such attachment, the top surface 741 has an upper catch or boss 742 and the upper portion 932 defines an upper bore 937 having a shape substantially corresponding to an outer shape of the upper catch 742.

One method for attaching the band 931 to the female part 14 includes first hooking the lower portion 934 onto the lower catch 681. Preferably, the connection of the lower portion 934 to the lower catch 681 is not permanent (but it can be). The upper portion 932 is, then, hooked to the upper catch 742. Preferably, the upper catch 742 is malleable and can be stamped or otherwise compressed, for example, in the manner of a rivet head, to deform out and over the upper end portion 936 of the upper portion 932 of the band 931 and fixedly (and, therefore, permanently) fasten the band 931 to the female part 14. Other connection possibilities for the upper and lower catches 742, 681 are also possible. One reason why the band 931 is configured to wrap around the cover portion 56 is to eliminate and/or reduce edge effects and stress concentrations and to carry most of the load imparted upon the band 931 along the length of the band 931 in its longitudinal direction, a feature discussed in greater detail below with respect to use of the retrieval device 1100.

The band 931 is shaped and sized to a length corresponding at least to the distance at which the slide 70, 74 is furthest away from the cover portion 56. Therefore, as shown in FIG. 9, when the slide 70, 74 is closest to the cover portion 56, a portion of the band 931 extends away from and does not contact the cover portion 56; the portion rests loosely with no tension on top of the female part 14. In comparison, when the slide 70, 74 is further away from the cover portion 56 as shown in FIG. 10, that portion of the band 931 previously extending away from the cover portion 56 now touches or is very close to the cover portion 56 and the band 931 rests with minimal slack on top of the female part 14. Thus, the band 931 is of a material flexible enough to move between these two configurations.

It is noted that the closed top surface 561 of the cover portion 56 provides a smooth and substantially non-frictional surface upon which the upper portion 932 of the band 931 may rest and be supported. Preferably, the band 931 rests loosely with no tension on top of the top surfaces 561, 741 of the cover portion 56 and slide cover 74.

The illustrated and described band removal device 930 and the illustrated and described embodiment for attaching the band 931 to the fixed and moving portions of the female part 14 are only exemplary. The band removal device 930 can take any form that moves the cover portion 56 and the slide portion 74 with respect to one another and the band 931 can be attached in any manner to the female part 14. For example, loop eyelets can be positioned entirely around a circumference of the cover portion 56 and the slide portion 74 in a plane that is parallel to a plane defined by the slide 70. A wire, which can be of any material similar to that described for the band 931, can be strung through all of the eyelets, thus forming a wire railing surrounding the cover portion 56 and the slide portion 74. When pulled, the loop defined by the wire will close, similar to a common snare, and move the cover portion 56 and the slide portion 74 closer to one another. In such a configuration, the grapple 1110 can grasp anywhere around the cover portion 56 and the slide portion 74.

When the lower bore 935 of the J-shaped band 931 is hooked upon the lower catch 681, longitudinal and/or vertical forces acting upon the upper portion 932 or the middle portion 933 do not remove the lower portion 934 from the catch 681. And, fastening of the upper portion 932 to the ceiling 741 of the slide cover 74, in particular, permanent fastening, substantially prevents any longitudinal, horizontal, and/or vertical force acting upon the upper portion 932 or the middle portion 933 from removing the lower portion 934 from the catch 681.

The removal assembly 930 is configured to unlock the female part 14 as the two components including the cover portion 56 and the slide cover 74 are moved towards one another. The illustrated and described embodiment can be expanded to include other embodiments that could be made to attach and unlock the fastener parts 12, 14 to one another. The flexible member 931 could be made to wrap around one component and be affixed to two points on the other component, for example. To easily unlock the female part 19, the unlocking mechanism should be easily accessible on the fastener 10 and easily actuatable.

To cause the flexible member 931 to impart a load sufficient to unlock the fastener requires the use of the retrieval device 1100.

The retrieval device 1100 is able to access the removal assembly 930 because the cover portion 56 and the slide cover 74 are separated to define a cavity 562 therebetween, into which the grapple 1110 of the retrieval device 1100 may be inserted. As shown, for example, in FIG. 11, the grapple 1110 is sufficiently small to easily access the cavity 562. Actuation is easy because the user needs only to pull upon the band 561 with the retrieval device 1100 in any direction orthogonal to a plane defined by the upper portion 932 of the band 931. A preferred pull direction is indicated by arrow 1102.

A preferred shape of the grapple 1110 is a J-shaped hook having a catch bottom (shown touching the bottom surface of the upper portion 932 of the band 931 in FIG. 11) with a portion of the catch bottom crossing the axis of an actuation wire 1112. In a preferred embodiment, the actuation wire 1112 is integral with the grapple 1110 and is of the same material as the grapple 1110 and extends proximally in the direction 1102 towards a non-illustrated, and, preferably, spring-loaded, actuation device that permits the actuation wire 1112 to extend distally out of the cowling 1104 when a force is directed distally upon the actuation device and, upon removal of the force, to automatically spring back in the proximal direction 1102. Therefore, when the user determines that the grapple 1110 has caught the upper portion 932 between the cover portion 56 and the slide cover 74, the user will "let go" of the actuation device and the cowling 1104 (which has a substantially larger diameter than the actuation wire 1112) will clamp upon the upper surface of the upper portion 932 and, thereby, lock the retrieval device 1100 to the band 931. Such locking, or "capture" as it is referred to herein, occurs because the hook portion of the grapple 1110 extends not only around and under the band 931, but also back again towards the retrieval device 1100. As such, when the grapple 1110 grasps the hand 931 and the actuating force is removed, the band 931 is entirely surrounded—by the grapple 1110 on three sides) and the cowling 1104 on the fourth side. The bias of the actuating device in the proximal direction 1102 is, preferably, sufficient to prevent slippage or removal from the band 931 after capture.

The actuation device can be in the form of a spool and thumb ring, for example. The actuation device is affixed to the actuation wire 1112 so that rotation of the actuation wire 1112 (and, therefore, the grapple 1110) is possible by rotating the actuation device or a portion thereof. A flexible shaft 1106 connects the distal and proximal ends of the retrieval device 1100. The shaft 1106 is configured to be inserted in an operating channel of an endoscope.

One feature of the device biasing the actuation wire 1112 in the proximal direction 1102 imparts a force that only captures the band 931. Alternatively, another feature of the biasing device imparts a force that not only captures the band 931, but also pulls or retracts the band 931 a distance into the hollow interior of the cowling 1104.

To allow the band 931 to be pulled into the hollow interior of the cowling 1104, the hollow has an inner diameter dimensioned to be larger than the greatest width of the grapple 1110 (radially away from an axis of the wire 1112). Thus, the grapple 1110 can enter the cowling 1104 entirely. The hollow of the cowling 1104 further has a depth (from a distal end thereof and extending proximally thereto) that is greater than the height of the grapple 1110 (in a longitudinal direction of the wire 1112). Thus, when the band 931 is to be pulled inside the cowling 1104, the catch bottom of the grapple 1110 travels in a proximal direction within the cowling 1104 to a given distance (defined below) from the distal-most end of the cowling 1104.

If the device biasing the actuation wire 1112 in the proximal direction 1102 only imparts a capturing force upon band 931, the actuation device also includes a secondary actuator that pulls the retrieval device 1100 further within the cowling 1104 such that the grapple 1110 enters the cowling 1104 to the given distance. A multi-force actuator gives the user more control over the unfastening procedure because the user has the opportunity to decide whether or not the band 931 will or will not be pulled and, thereby, unlock the locked fastener 10. Of course, the embodiment of the biasing device imparting both a capture force and an unlock force can exist in a single actuator that has, for example, a tooth, pawl, or catch preventing proximal movement of the actuation wire 1112 past the capture position. Such a feature can be moved out of the way of the actuation wire 1112, for example, by pressing an unlocking safety coupled thereto when removal is desired. Accordingly, the biasing device can be configured to always impart a force sufficient to unlock the fastener, but to not enable a full unlocking movement of the actuation wire 1112 unless and until the safety is actuated.

To impart the needed forces and assure the removal of the implant, the flexible shaft 1106 is, preferably, a longitudinally stiff sheath.

The relative positions of the cover portion 56 and the slide cover 74 define the distance along which the slide cover 74 needs to move in order to unlock the fastener 10. Accordingly, the band 931 needs to be shortened at least enough to move the slide cover 74 to the unlocking position. When the band 931 is pulled into the cowling 1104, it is folded upon itself. Such folding occurs because the catch bottom of the grapple 1110 is moved proximally in relation to the two opposing distal end portions of the cowling 1104 in contact with the band 931. Therefore, if the slide cover 74 needs to move, for example, 4 mm, to unlock the fastener 10, the catch bottom needs to enter at least approximately 2 mm into the hollow interior of the cowling 1104. Accordingly, the given distance that the catch bottom of the grapple 1110 enters the cowling 1104 is equal to approximately one-half the distance along which the slide cover 74 needs to move in order to unlock the fastener 10.

In contrast to a conventional snare, the direction in which the retrieval device 1100 of the present invention applies a force is optimal. Specifically, an actuating force is applied at the proximal actuating device to withdraw the grapple 1110 into the cowling 1104. Because the actuation wire 1112 is directly attached to the band 931, the force imparted on the band 931 is entirely transferred to the band 931. Simply put, the longitudinal force in the proximal direction 1102 of the retrieval device 1100 is directly translated into a force moving the slide 74 and the cover portion 56 towards one another in a direction orthogonal to the proximal direction 1102 and is directly proportional to the longitudinal force, with minor losses because of friction where the deforming band enters the cowling 1104.

The fastener 10 shown in FIGS. 9 and 10, for example, is purposefully slimmed to reduce its weight. When made substantially of titanium, for example, the fastener of the present invention weighs approximately 1 gram.

An important feature of the fastener 10 of the present invention is the ability to reverse the plications formed by implanting the fastener 10 in a patient according to the system of the present invention. The reversibility is advantageous because it mitigates risks associated with treatment, in particular, treatment of GERD. In addition, the reversibility gives the user the ability to remove and redo the implant if the original anatomical change (plication) is considered inadequate. Once the female side is unlocked, the removal device can be used to pull the female side off the tissue and the implant can be removed orally. Then, the male side can be removed as originally planned using a foreign body extractor or can be allowed to pass naturally through the digestive system of the patient.

As discussed above, the posts 32, 34 are spring-biased to collapse into a base of the male component when not retained against the bias. This operates to prevent injury to the patient should the male part 12 inadvertently become separated from the applicator instrument 200 or from the female part 14 after coupling therewith. Given the size of the parts and the protection of sharps from exposure to the body, the parts may be safely passed through the gastrointestinal system.

Folding the posts 32, 34 into the elongate channels 24, 26 as shown in FIG. 3 illustrates a first exemplary embodiment for placing the posts 32, 34 in a safety position should the male part 12 become dislodged and fall away from the implantation site into the patient. FIGS. 14 to 17 illustrate a second embodiment of the male part 12. Unlike the first embodiment, the posts 32, 34 are not rotatably coupled to the base 18. In the second embodiment, the posts 32, 34 are fixedly connected to a respective half 181, 182 of a two-part base 18. In one post embodiment, the posts 32, 34 can have a non-illustrated male thread that screws into a non-illustrated female thread within a respective opening 201, 221 of each base half 181, 182. Alternatively, the posts 32, 34 can be press fit into the openings 201, 221 or fixedly and/or removably connected into the openings 201, 221 in any other similar way.

Figure 16:
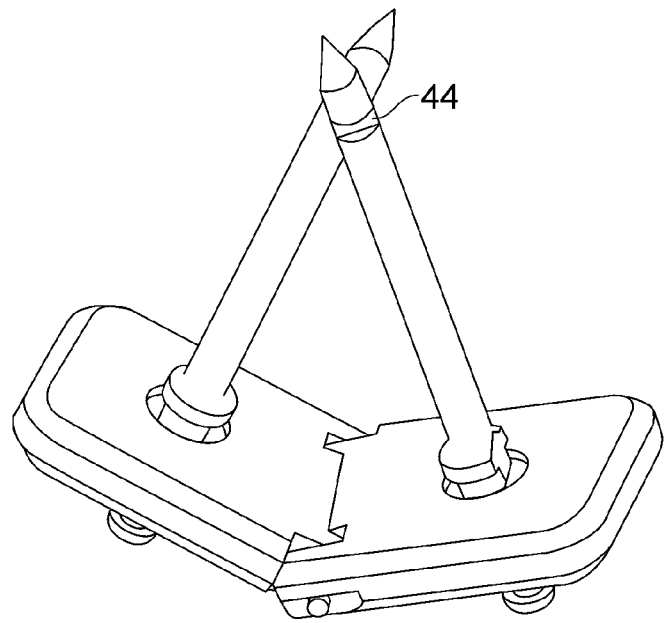
FIG. 16 is a top perspective view of the male part of FIG. 14 in a collapsed configuration.
Figure 17:
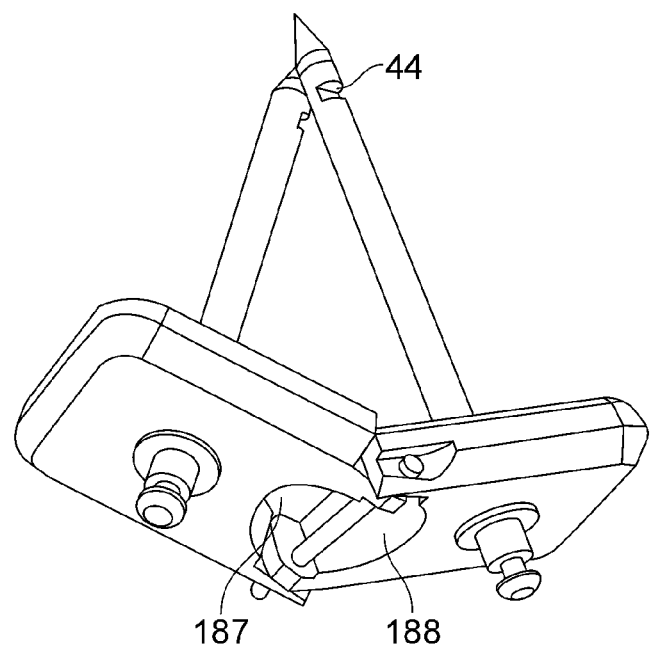
FIG. 17 is a bottom perspective view of the male part of FIG. 16.

The halves 181, 182 are connected to one another at a hinge 183. The hinge 183 has a hinge axis substantially orthogonal to a non-illustrated longitudinal line extending from a central axis of the first post 32 to a central axis the second post 34. The base halves 181, 182 of the second fastener embodiment are rotatably coupled to one another so that, when rotated, the tips or ends 323, 343 of the posts 32, 34 approach one another until they touch or are sufficiently close to one another to present a profile that is less likely to cause harm to a patient should the male part 12 become loose and inadvertently fall away inside a patient from a fastening location. An example of this safety orientation is shown in FIGS. 16 and 17.

The base halves 181, 182 can be configured to exactly touch the tips 323, 343 to one another. However, in the preferred configuration shown in FIGS. 14 to 17, the base halves 181, 182 have a configuration that rotates to place the tips 323, 343 next to one another. Such a configuration is advantageous over a configuration where the tips 323, 343 of the posts 32, 34 touch each other because exact touching of the two tips creates a single sharp. Therefore, force on a portion of the base opposing the sharp can cause a two-post puncture, which can migrate entirely through the gastric/intestinal wall. In contrast, crossing the tips decreases the possibility of a two-post puncture and, therefore, prevents migration through the gastric/intestinal wall because, if only one post pierces the wall, the other post, being in a different orientation, does not pierce the wall at the same location. The other non-piercing post, accordingly, prevents the fastener from continuing entirely through the pierced wall. Thus, potential perforations, if they were to occur, are minimized.

To offset the two tips 323, 343 in the preferred configuration, instead of providing a hinge 183 connecting the two halves 181, 182 with a hinge axis substantially parallel to the longitudinal line extending from a central axis of the first post 32 to a central axis the second post 34, the hinge 183 is skewed at an angle α to the longitudinal line. See FIG. 14. Accordingly, in a preferred embodiment, the two halves 181, 182 are shaped identically, with each half 181, 182 having a hinge recess 184 and two hinge flanges 185. Each hinge recess 184 and hinge flange 185 has a respective bore for receiving a hinge pin 186, best illustrated in FIGS. 15 and 17.

To bias each of the halves 181, 182 to a position where the ends 323, 343 are closer to one another, each half 181, 182 has a recess portion 187, 188 in which is disposed a respective portion of a bias device 189. A preferred embodiment for the bias device 189 is a torsion spring having two free ends 190, 191 respectively imparting a bias force against surfaces 192, 193 within the recesses 187, 188.

Like the second post groove embodiment of FIGS. 9 to 12, the posts 32, 34 are illustrated in FIGS. 14 to 17 with only one slot 44 or groove 44a per post. In both of the first and second slot embodiments, the user is substantially prevented from applying excessive compression to the plication between the male and female parts 12, 14 because the posts 32, 34 bottom out inside the slide cover 74 or inside both the cover portion 56 and the slide cover 74. (It is noted that the posts 32, 34 bottom out without damage to the tips.) The distance between the upper surface of each base half 181, 182 and the respective slot 44 will determine the compression that will be imparted to the plication between the male and female parts 12, 14—a shorter distance applies more compression than a longer distance.

Figure 18:
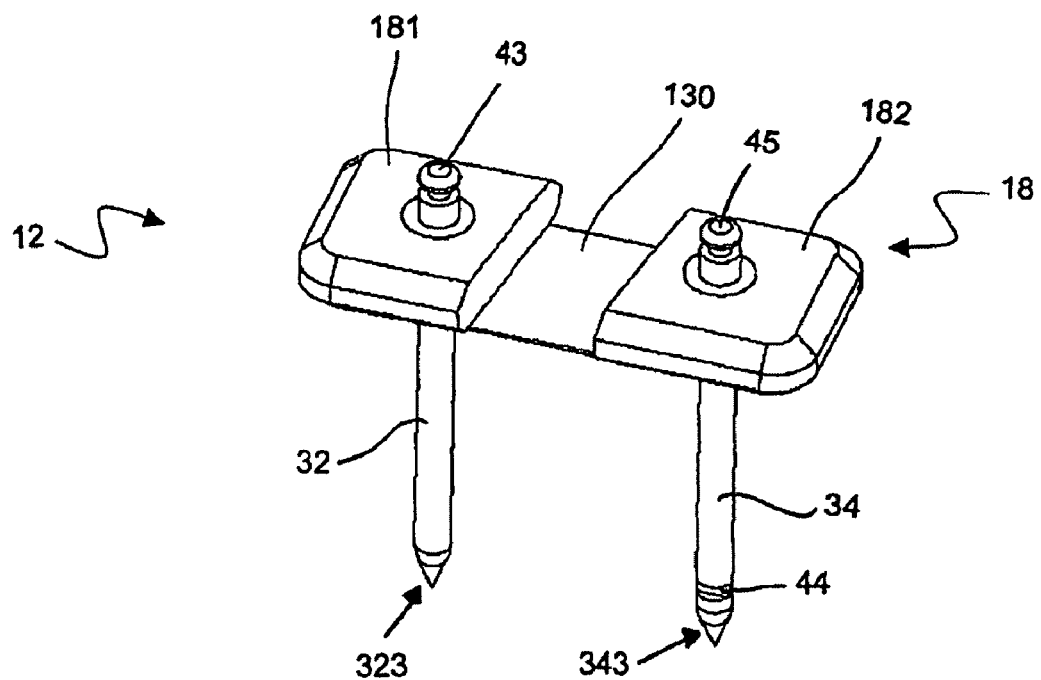
FIG. 18 is a bottom perspective view of a further alternative embodiment of the male part of FIG. 2.
Figure 19:
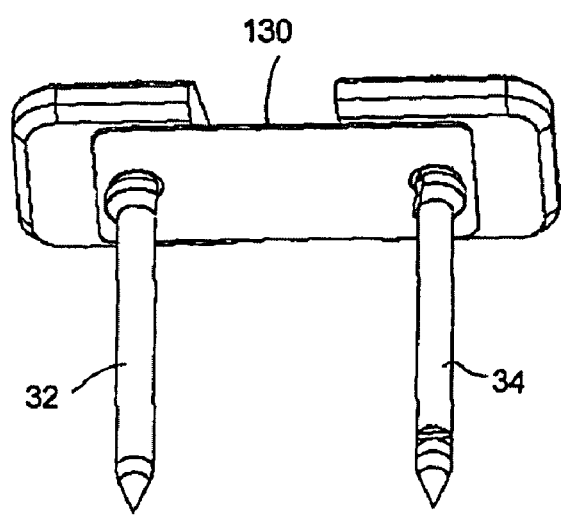
FIG. 19 is a top perspective view of the male part of FIG. 18.
Figure 20:
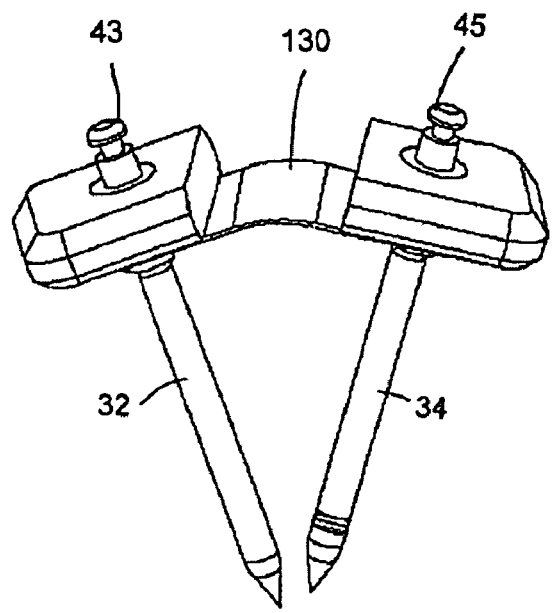
FIG. 20 is a bottom perspective view of the male part of FIG. 18 in a collapsed configuration.
Figure 21:
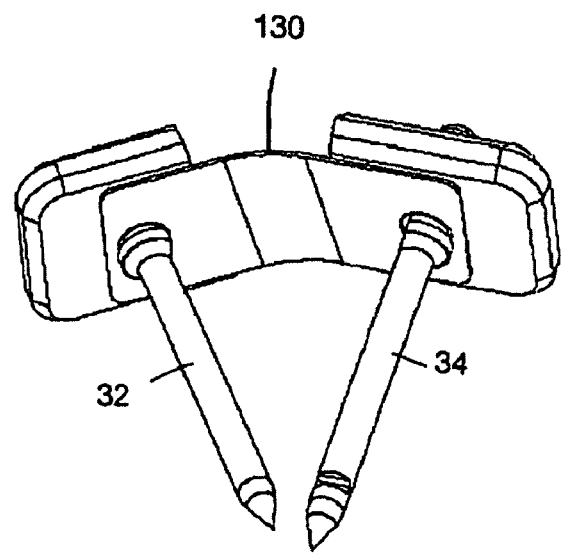
FIG. 21 is a top perspective view of the male part of FIG. 20.
Figure 22:
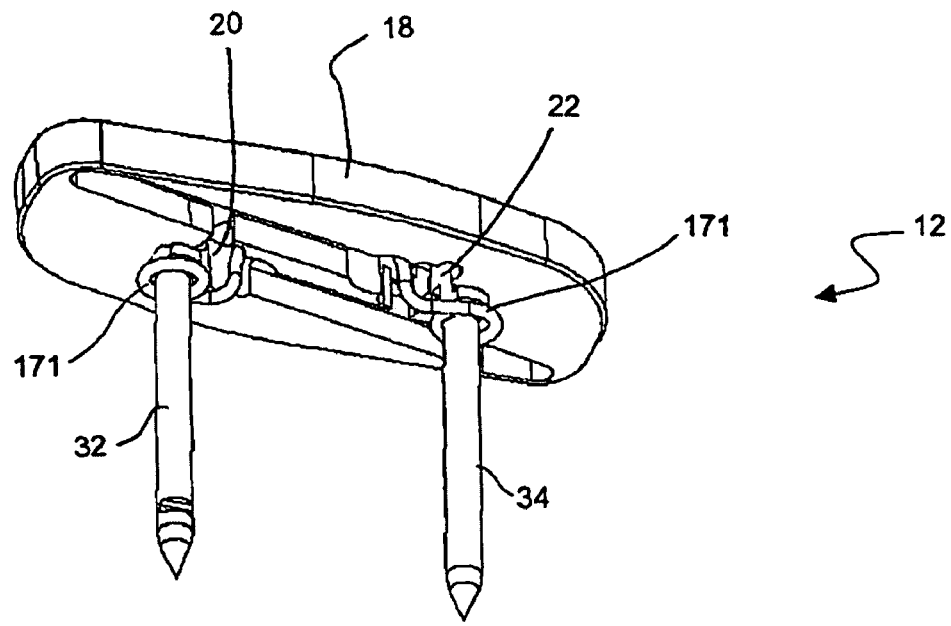
FIG. 22 is a top perspective view of another alternative embodiment of the male part of FIG. 2.

A third exemplary embodiment of the base 18 is shown in FIGS. 18 to 21. In the third base embodiment, a flexible plate 130 replaces the hinge 183. The plate 130 is fixedly connected to each half 181, 182 of the two part base 18. In its rest state, the plate 130 assumes the position illustrated in FIGS. 20 and 21, in which the tips 323, 343 are next to one another or exactly touch one another. Thus, the plate 130 has a natural curve. For installation into the distal end effector 202, the halves 181, 182 of the male part 12 are bent away from one another to substantially flatten the plate 130 and place the posts 32, 34 substantially parallel to one another, as shown in FIGS. 18 and 19. In such a flattened position, the male part 12 can be installed into the recess 240 of the arm 220 such that the lower portions 43, 45 of the posts 32, 34 enter the two stepped throughbores 242, 244 shown in FIGS. 29 and 30 and as will be explained in greater detail below. When the male part 12 is held within the recess 240 of the male jaw 226, the lower portions 43, 45 of the posts 32, 34 are retained in the stepped throughbores 242, 244 in an upright configuration and, consequently, rotation of the posts 32, 34 caused by the bias of the plate 130 into the collapsed configuration shown in FIGS. 20 and 21 is prevented.

A fourth exemplary embodiment of the base 18 is shown in FIGS. 22 to 25. In the fourth embodiment, the posts 32, 34 are naturally in the position shown in FIG. 22. The posts 32, 34 may be press fit into the respective openings 20, 22 or, alternatively, the posts 32, 34 may be integral with the base 18 and, when moved as set forth below, may be able to be torn away from the upright position into a nested position (see FIGS. 24 and 25).

Figure 23:
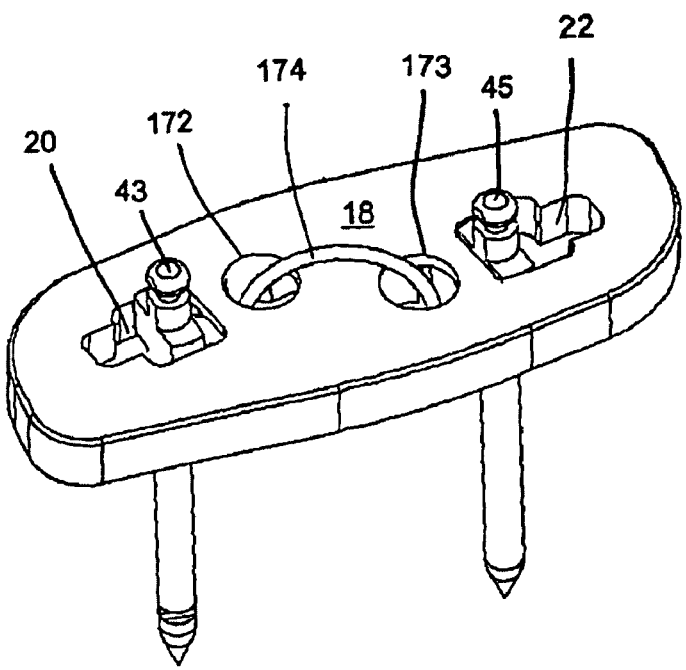
FIG. 23 is a bottom perspective view of the male part of FIG. 22.
Figure 24:
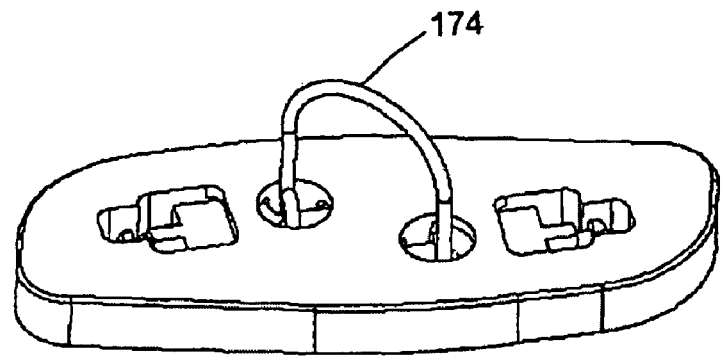
FIG. 24 is a bottom perspective view of the male part of FIG. 22 in a collapsed configuration.

A post release wire 171 is fastened to a portion of each post 32, 34 close to the base 18 (the wire 171 can be a band or a braided cable, for example). The wire 171 can be merely wrapped or tied around each post 32, 34 or can be welded, glued, or otherwise attached to each post 32, 34. The wire can be threaded through the two openings 20, 22 or, preferably, as shown in FIG. 23, the wire 171 is threaded through two wire openings 172, 173 formed in the base 18 to create a loop 174 on a bottom side of the base 18 opposite the ends 323, 343 of the posts 32, 34. At any time after being removed from the distal end effector 202, the posts 32, 34 can be moved from the extended position shown in FIGS. 22 and 23 to the nested or collapsed position shown in FIGS. 24 and 25 merely by pulling upon the loop 174, preferably, in a direction orthogonal to the plane defined by the bottom surface of the base 18 shown, in particular, in FIGS. 23 and 24. Therefore, when the loop 174 is pulled into the position shown in FIG. 24, the pulling force results in a torque upon the posts 32, 34 sufficient to move the posts 32, 34 out of the upright position and into the nested position shown, in particular, in FIG. 25. In the nested position, the patient in whom the fastener 10 has been implanted can safely pass the male part 12.

Figure 25:
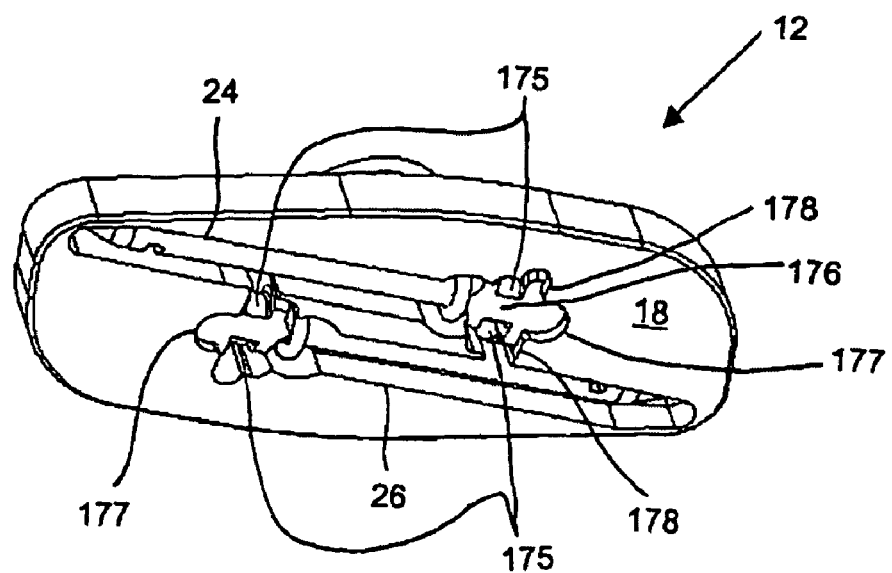
FIG. 25 is a top perspective view of the male part of FIG. 24.

An example of a removable connection of the posts 32, 34 to the base 18 is shown in FIG. 25. The posts 32, 34 each have opposing grooves 175 surrounding an approximately circular post portion 176. Each post 32, 34 is press fit onto a configuration having an approximately circular post holder slot 177 and two edges that fit into the opposing grooves 175 when the posts 32, 34 are in the position shown in FIGS. 22 and 23. Another way to describe the connection between the posts 32, 34 and the configuration 175, 177 is that the slot 177 forms a keyway for the tongue and groove connection of the two edges and the grooves 175 of the posts 32, 34. Even though the configuration securely holds the posts 32, 34 upright when the posts 32, 34 are press fit therein, a sufficiently strong torque removes the posts 32, 34 from the configuration and causes the posts 32, 34 to rest within the two channels 24, 26.

As further discussed below, and clearly shown in the figures relating thereto, the parts 12, 14 of the fastener 10 are delivered through the esophagus in a lengthwise orientation.

Figure 26:
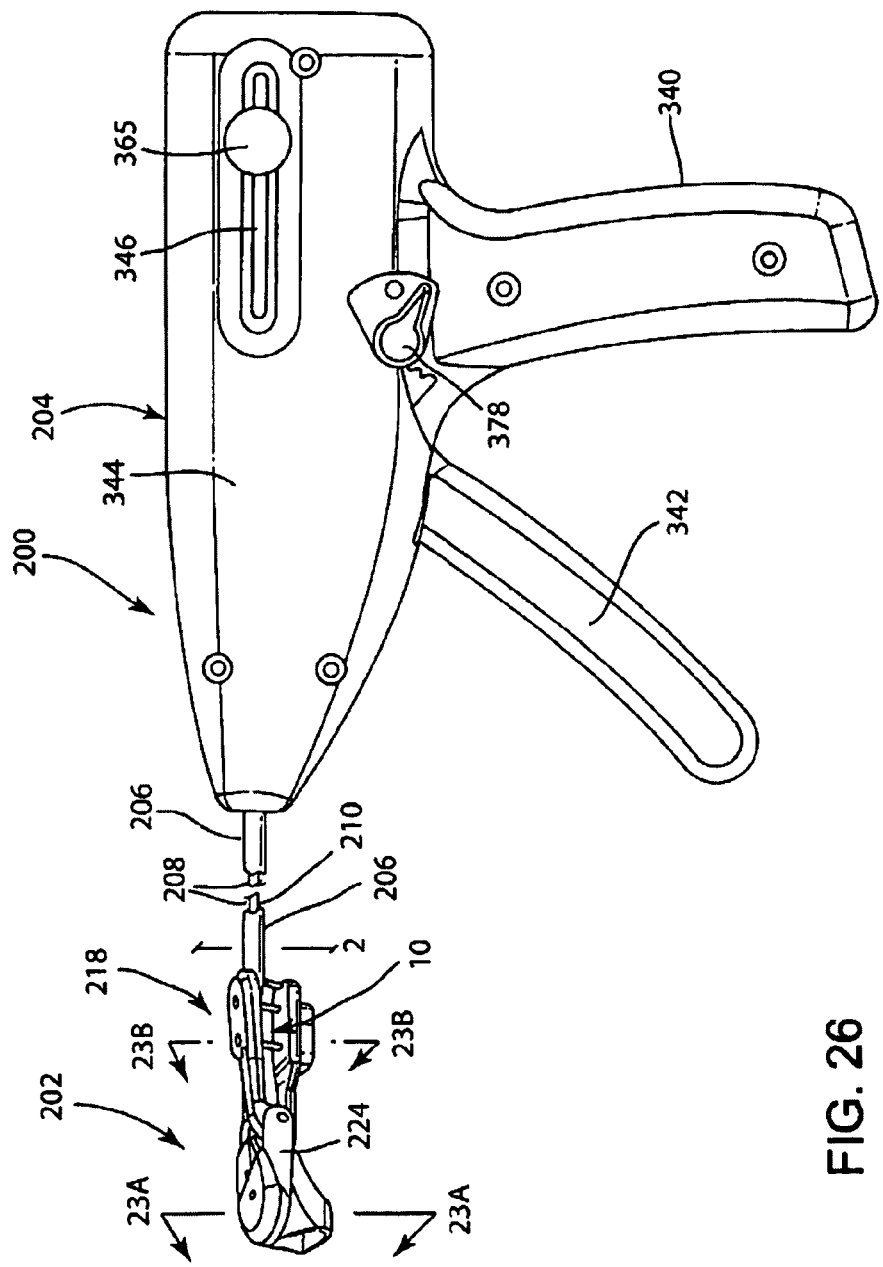
FIG. 26 is a fragmentary side view of an endoluminal tissue plication and fastener applicator instrument according to the invention with a fastener loaded in an end effector.

Turning now to FIG. 26, an endoluminal tissue plication and fastener applicator instrument 200 is shown. The instrument 200 generally includes a distal end effector 202, a proximal actuation handle 204, and a tubular control shaft 206 housing at least two control elements 208, 210 (wire, cables, coils, ribbons, etc.) extending between the handle 204 and the end effector 202.

In a preferred embodiment, the control shaft 206 is a stainless-steel flat-wire wound coil covered in a lubricious sheath and is substantially smaller in diameter than a conventional endoscope. The flat wire limits elongation of the control shaft 206 when the control shaft 206 is under tension due one or the other of the control elements 208, 210 being under compression. Another way to limit longitudinal extension is to attach a jacket, preferably, of TEFLON®, at either end of the shaft 206 The jacket may be fixedly attached at its proximal and distal ends to the actuating handle 204 and the distal end effector 202, respectively, by barb fittings on projections over which the jacket is stretched; the attachments of the jacket may be further strengthened by crimp bands or shrink bands of metal or shrink tubing over the area where the jacket engages the barb fittings. Alternatively, a rounded wire coil can be used, which allows the control shaft 206 to be bent into a tighter radius than the flat-wire wound coil. This ability to bend more sharply is important because when the end effector 202 is being inserted through the mouth towards the esophagus, it must pass the Cricopharyngeal Junction. The route through the Cricopharyngeal Junction includes an approximately ninety-degree turn. Thus, it is important for the end effector 202 to be able to bend at an angle to the substantial longitudinal extent of the control shaft 206, and the distal portion of the shaft 206 is required to be sufficiently flexible to facilitate easy passage of the effector 202. When guided along the guide wire 924, the stiffness of the guide wire 924 assists (along with user pressure) in bending the end effector orientation accordingly, but the control shaft 206 needs to bend as well.

In addition, the control shaft 206 has a relatively small diameter than the distal end effector 202, preferably not exceeding approximately 5 mm and, in particular, not exceeding approximately 4 mm.

The distal end effector 202 is adapted to plicate tissue and apply the two-part fastener 10 to opposed sections of the plicated tissue, and, according to several embodiments, is optionally adapted to be coupled to an endoscope or separate therefrom, as described in detail below. The actuation handle 204 operates the control elements 208, 210 to effect clamping and opening of the jaw assembly 218 and locking and release of the fastener 10, as also described in detail below.

Figure 27:
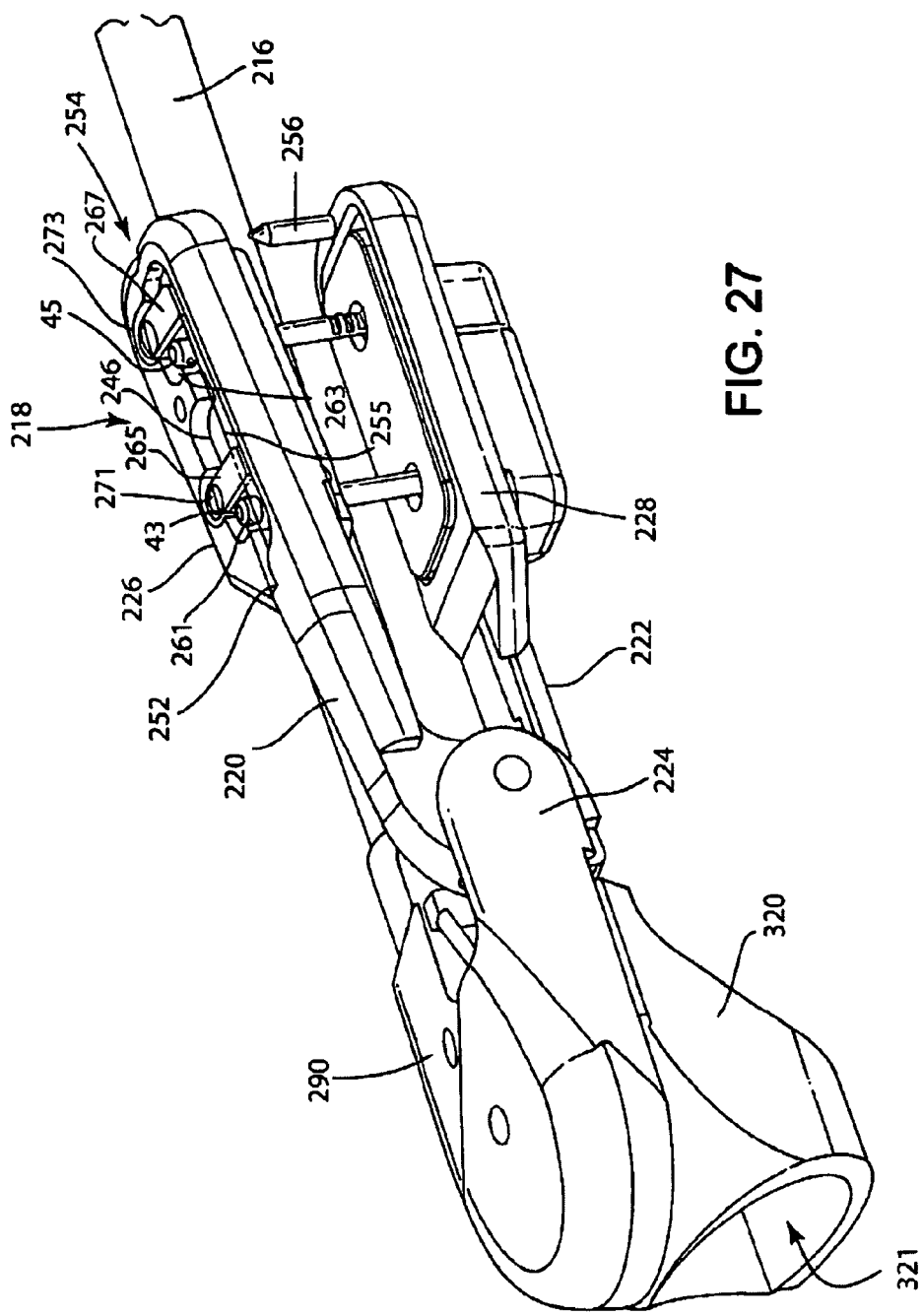
FIG. 27 is a fragmentary, side perspective view of the distal end of the instrument of FIG. 26.
Figure 29:
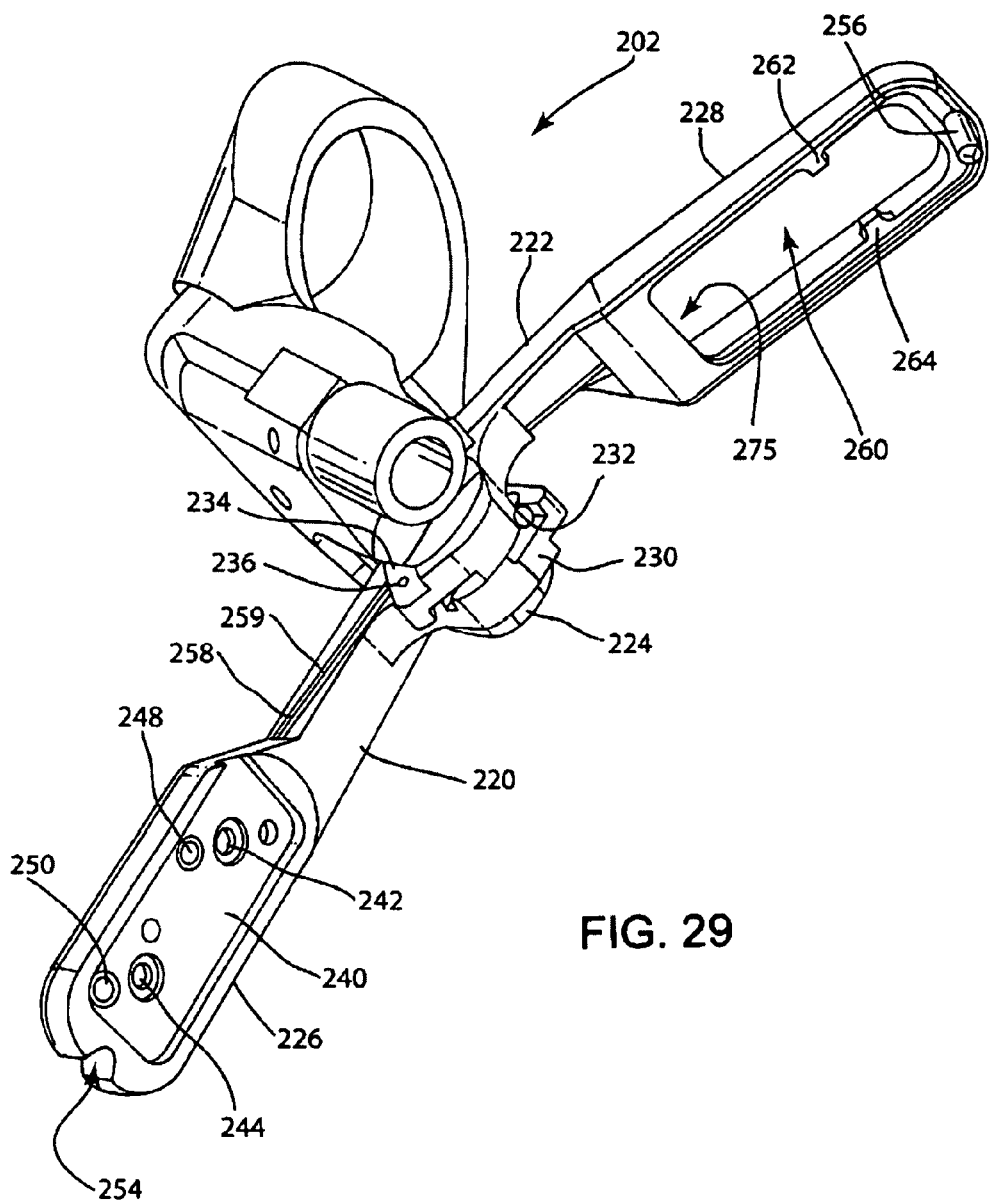
FIG. 29 is a perspective view of the distal end of the instrument from a proximal side thereof with the jaws in an open configuration without the fastener and with control shaft removed for clarity.

Referring now to FIGS. 27 through 29, the distal end effector 202 includes a jaw assembly 218 having a clevis 224, first and second arms 220, 222 mutually rotatable about the clevis 224, a housing 290, and a sleeve (continuous or slit cuff) 320 integral with the housing 290 and adapted to be slidably positioned about (or, if slit, snapped over) an end of an endoscope.

The first arm 220 of the jaw assembly 218 includes a male jaw 226 (adapted to receive the male part 12 of the fastener 10), and an opposite tang 230 having a coupling hole 232 adapted to receive a control element. The second arm 222 includes a female jaw 228 (adapted to receive the female part 14 of the fastener 10), and an opposite tang 234 having a coupling hole 236 adapted to receive a control element.

Figure 30:
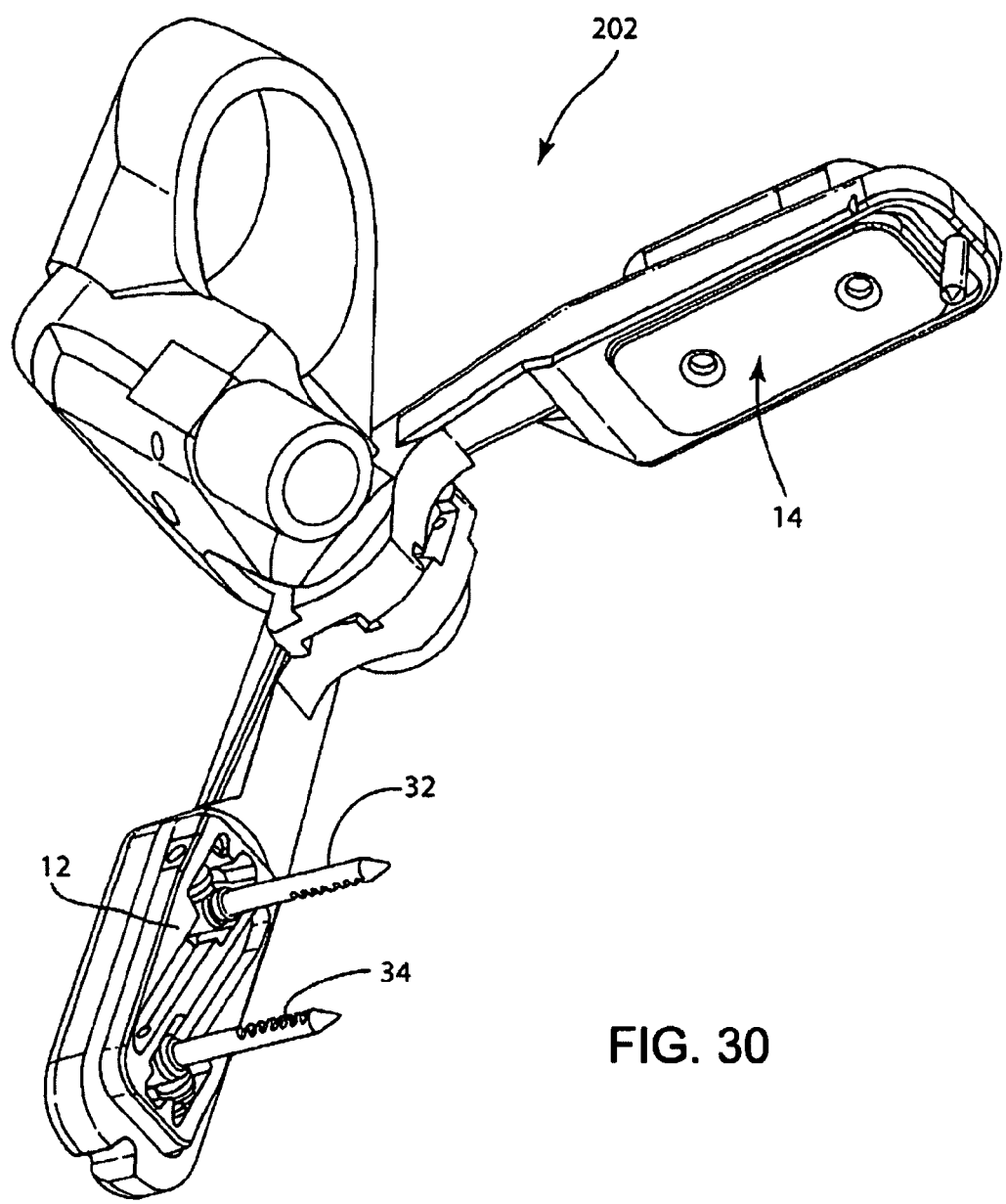
FIG. 30 is a perspective view of the distal end of the instrument of FIG. 29 with the fastener loaded in the end effector.

More particularly, the inside of the male jaw 226 includes a rectangular recess 240 adapted to receive the back of the male part 12 of the fastener 10, two stepped throughbores 242, 244, and two threaded holes 248, 250 (see FIG. 29). Referring to FIGS. 3 and 30, when the male part 12 is loaded into and held within the recess 240 of the male jaw 226, the lower portions 43, 45 as well as portions of the enlarged portions 33, 35 of the posts 32, 34 are received in the stepped throughbores 242, 244. Such a configuration retains the posts 32, 34 upright and, consequently, prevents their rotation into a collapsed configuration. Referring back FIGS. 27 and 29, a first embodiment of the male jaw 226 provides a recess 246 at the outside of the male jaw 226 through which the threaded holes 248, 250 are accessed, and an exit opening 252 in communication with a track 258 (which carries a release element, discussed below) through the first arm 220. The end of the male jaw 226 is also provided with a groove 254, the function of which is described below.

In the first embodiment, the first release element 259 extends within the track 258 of the first arm 220 from a housing 290 of the clevis 224 and through the exit opening 252. The first release element 259 includes an actuation end 255 that is split to define two U-shaped portions 261, 263 which are respectively inserted into the bores 46, 48 (FIG. 3) of the lower end 43, 45 of the posts 32, 34 of the male part of the fastener. Friction plates 265, 267 are held over the U-shaped portions 261, 263, with screws 271, 273 inserted into the threaded holes 248, 250, to provide frictional resistance from inadvertently dislodging the U-shaped portions from within the bores 46, 48.

Figure 31:
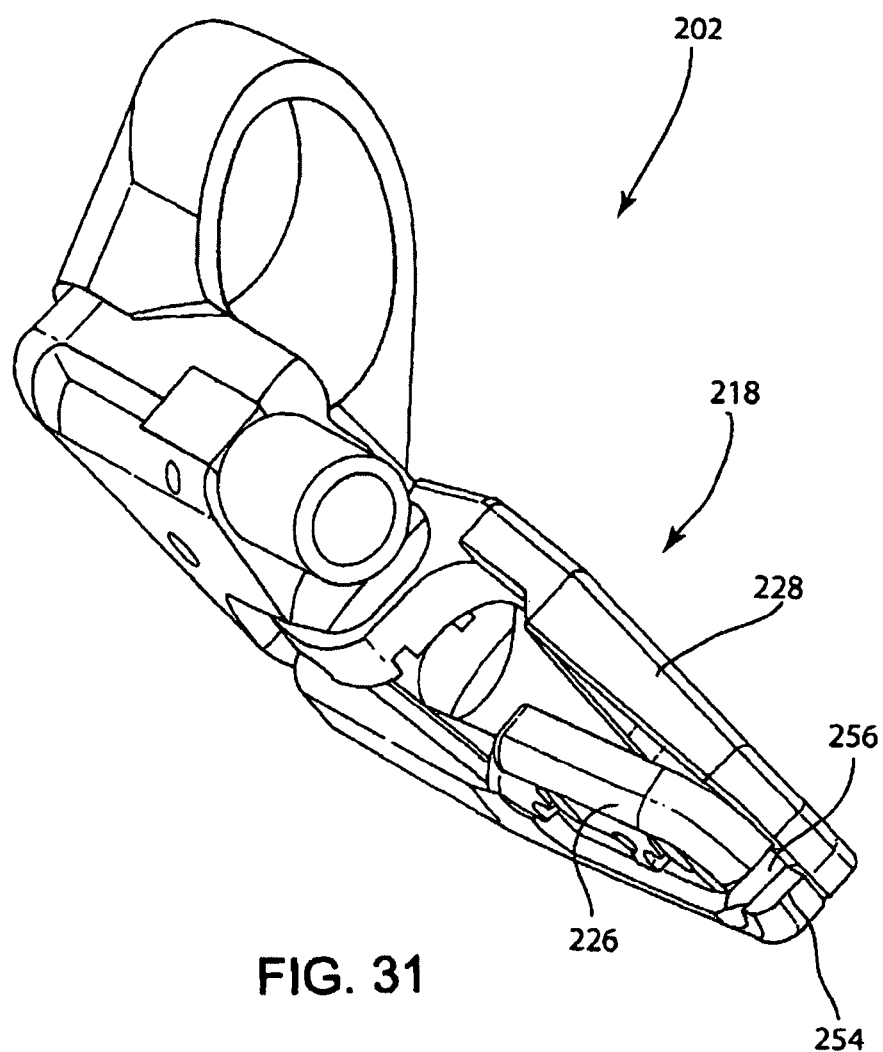
FIG. 31 is a perspective view of the distal end of the instrument of FIG. 29 with jaws in a closed configuration.
Figure 32:
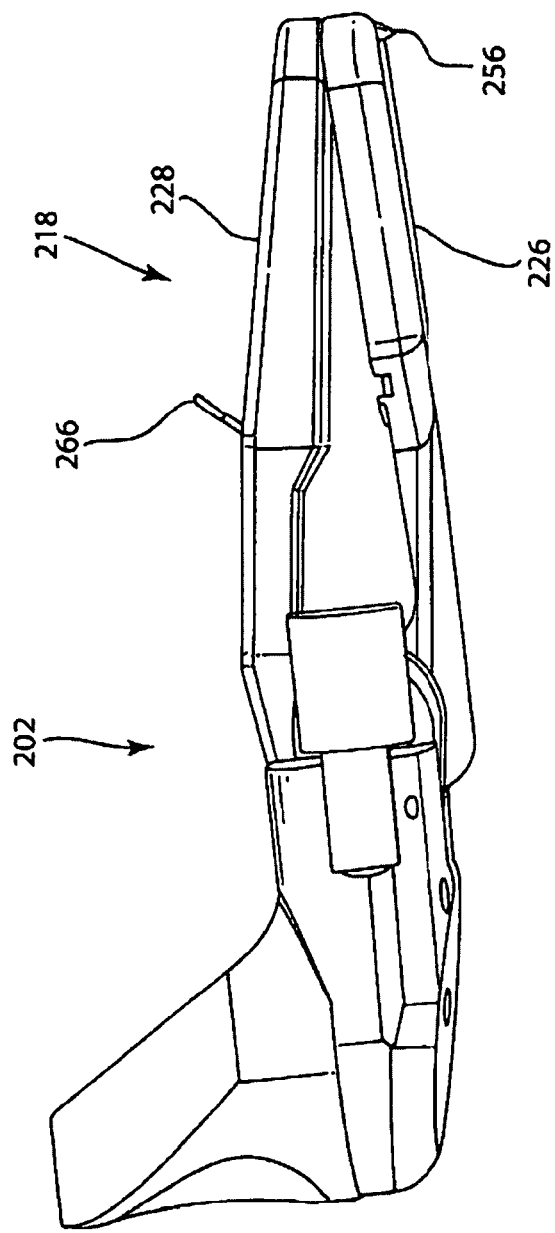
FIG. 32 is a side view of the distal end of the instrument of FIG. 31.

Referring to FIGS. 28 through 33, the female jaw 228 includes a relatively large generally rectangular opening 260 sized to receive the latch body cover 56 and latch slide cover 74 of the female part 14 of the fastener 10. The jaw 228 also defines a ledge 275 (FIGS. 29 and 33), and two catches 262, 264 that extend into the opening 260. The female part 14 is inserted into the jaw 228 in the locked position and, then, moved into the unlocked position such that the head 76 of the latch slide 70 (FIG. 5) lies over the ledge 275 and the catches 262, 264 extend within the setback 112 (FIG. 5) to lock the female part 14 in the jaw 228. A tissue piercing post 256 is provided at the terminus of the female jaw 228. Referring to FIGS. 31 and 32, when the female and male jaws 226, 228 are free of the fastener parts 12, 14 and closed together (e.g., after the fastener has been released and during retraction of the instrument), the post 256 resides in the groove 254 of the male jaw 226 to provide a more tapered configuration to aid in removal of the instrument from the patient. Also, the ends of each jaw 226, 228 have a tapered configuration to aid in removal of the instrument from the patient. See FIGS. 38 to 47. Instead of a taper, at least one fin, like a dorsal fin of a shark, can be placed at a distal end of at least one the jaws 226, 228.

Figure 33:
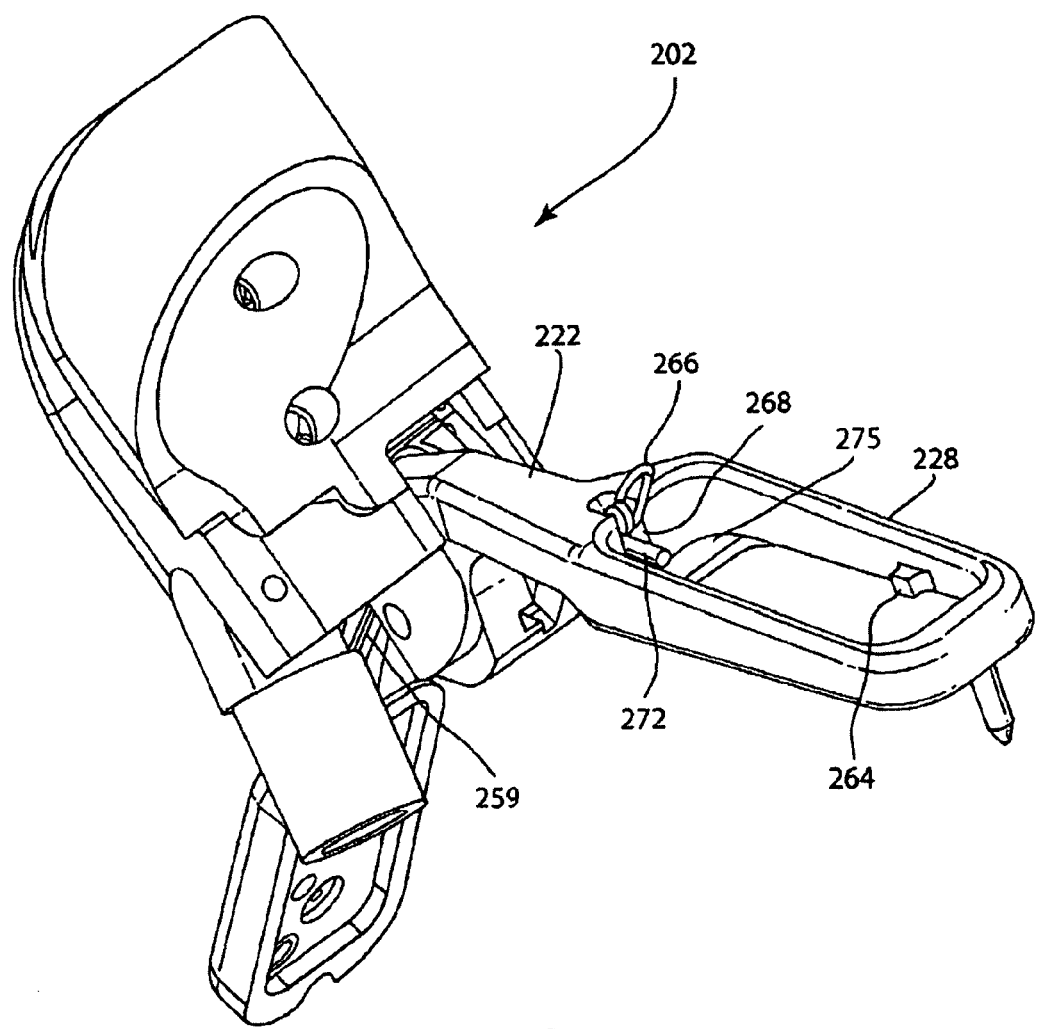
FIG. 33 is a side perspective view of the distal end of the instrument of FIG. 29.
Figure 34:
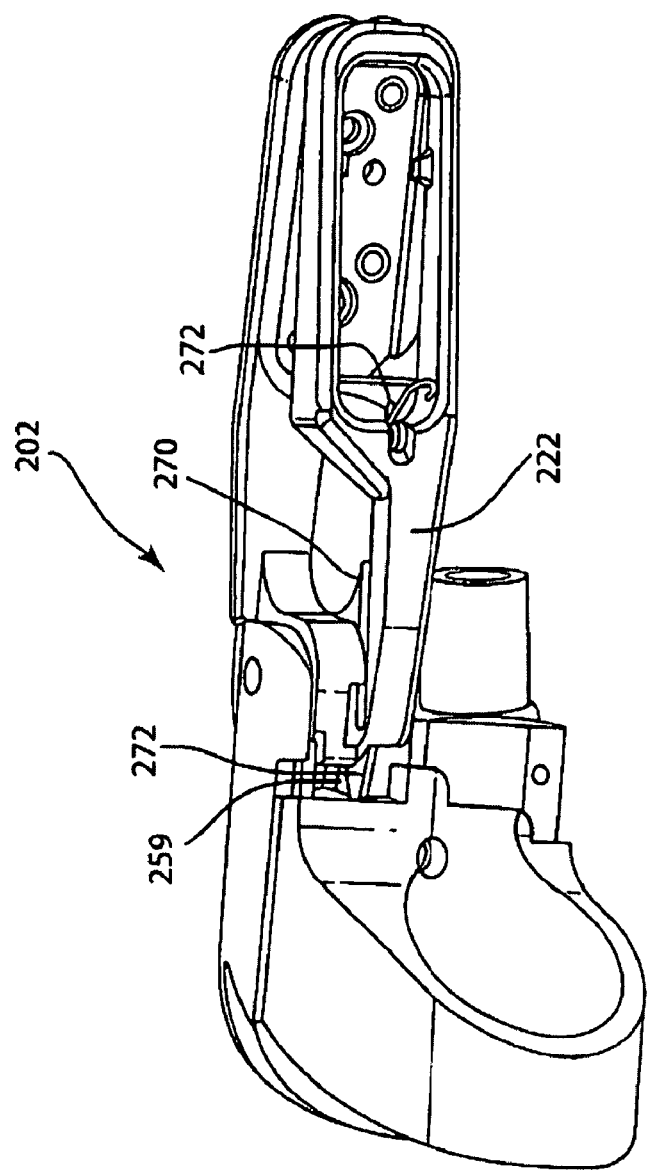
FIG. 34 is a perspective view of the distal end of the instrument of FIG. 32 from the female jaw side of the end effector.

Referring now to FIGS. 32 and 33, a torsion spring 266 is coupled to the female jaw 228 and adapted to force the female part 14 of the fastener 10 toward the terminus of the jaw, which operates to help align the male and female parts 12, 14 as the jaws 226, 228 are rotated toward each other through an arc. Moreover, the spring 266 permits movement of the female part 14 within the opening 260 to accommodate misalignment due to the amount of the tissue between the fastener parts. Referring to FIGS. 33 and 34, the female jaw 228 also includes an exit opening 268 for a wire track 270 extending along a side of arm 222. A second release element 272 extends within the track 270 from the housing 290 through the exit opening 268, as is described in further detail below.

Referring now to FIG. 35, the clevis 224 also includes a mount 280 at which the control shaft 206 (FIG. 26) is attached to the distal end effector 202 of the instrument 200. The mount 280 includes a bracket 282 that is coupled to the clevis 224 at pivot 284. The clevis 224 also defines a housing 290 for a mechanical assembly 292, which operates to transmit an input force on the control elements 208, 210 to the end effector 202 to effect movement of the jaw arms 220, 222 and locking and release of the fastener 10 therefrom.

In the first embodiment of the mechanical assembly 292, the assembly 292 includes a first bell crank 294 rotatably coupled about a pivot 296 that is, preferably, integrally formed with the housing 290. A distal end 298 of control element 208 is coupled to the first bell crank 294 at an input side of the bell crank 294, and a V-shaped wire 300 is attached to the bell crank 294 at an output side thereof. The V-shaped wire 300 extends to and is coupled within the coupling holes 232, 236 (FIG. 29) of the tangs 230, 234 of each of the two jaw arms 220, 222. Alternatively, two separate wires can be used to extend from the output side of the bell crank to the two tangs 230, 234. Starting from the open jaw position shown in FIG. 35, when the control element 208 is moved proximally relative to the control shaft (pull), the first bell crank 294 is rotated counter-clockwise, pulling the V-shaped wire 300 away from the jaws and, thereby, rotating the jaws 226, 228 into the closed position shown in FIG. 36. Still referring to FIGS. 35 and 36, it is also noted that when the jaws 226, 228 are forced into a completely closed position, additional force on control element 208 causes rotation of the mount 280 about the pivot 284 to cause the jaws to move even closer to the control shaft 206. Such movement reduces the profile of the end effector 202 to aid in removal of the instrument from the stomach, esophagus, and Cricopharyngeal Junction after the instrument 200 has implanted a fastener 10 according to the present invention. When the control element 208 is moved distally relative to the control shaft 206 (push), as shown in FIG. 35, the first bell, crank 294 is rotated clockwise to cause the Y-shaped wire 300 to forcibly rotate the jaws 226, 228 into an open position. In addition, when the jaws 226, 228 are in a fully opened position, additional force on control element 208 causes rotation of the mount 280 about the pivot 284, which rotation pushes the entire jaw assembly 218 away from the control shaft 206 because of the pivot 284. Such movement provides additional space between the jaw assembly 218 and the control shaft 206 to facilitate grabbing tissue between the jaws 226, 228.

Figure 36:
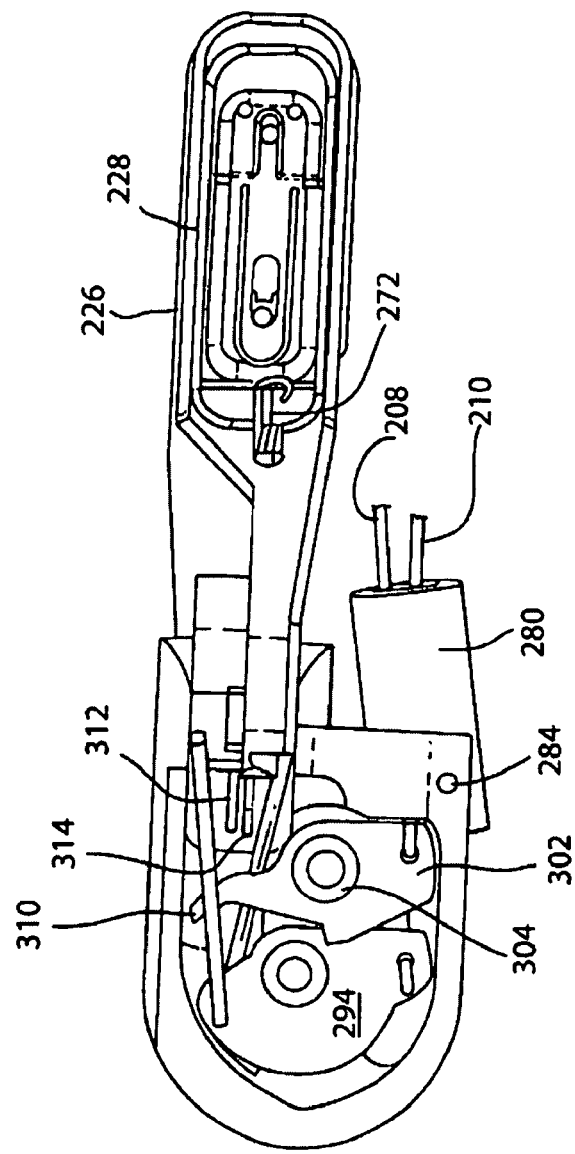
FIG. 36 is a fragmentary, plan view of the distal end of the instrument of FIG. 35 with the jaws in a closed configuration.

Referring still to FIGS. 35 and 36, the mechanical assembly 292 also includes a second bell crank 302 that is rotatably coupled about a pivot 304 that is also, preferably, integrally formed with housing 290. A distal end 306 of control element 210 is attached to one side of the second bell crank 302. Another side of the second bell crank 302 defines a push bar 310. The ends of release elements 259, 272 (see FIG. 34) terminating within the housing 290 are, preferably, bent or otherwise formed at an angle to define contact portions 312, 314 (FIGS. 35 and 36) that, when the jaw arms 220, 222 are in a closed position (FIG. 36), are oriented substantially perpendicular to the orientation of the push bar 310.

Figure 37:
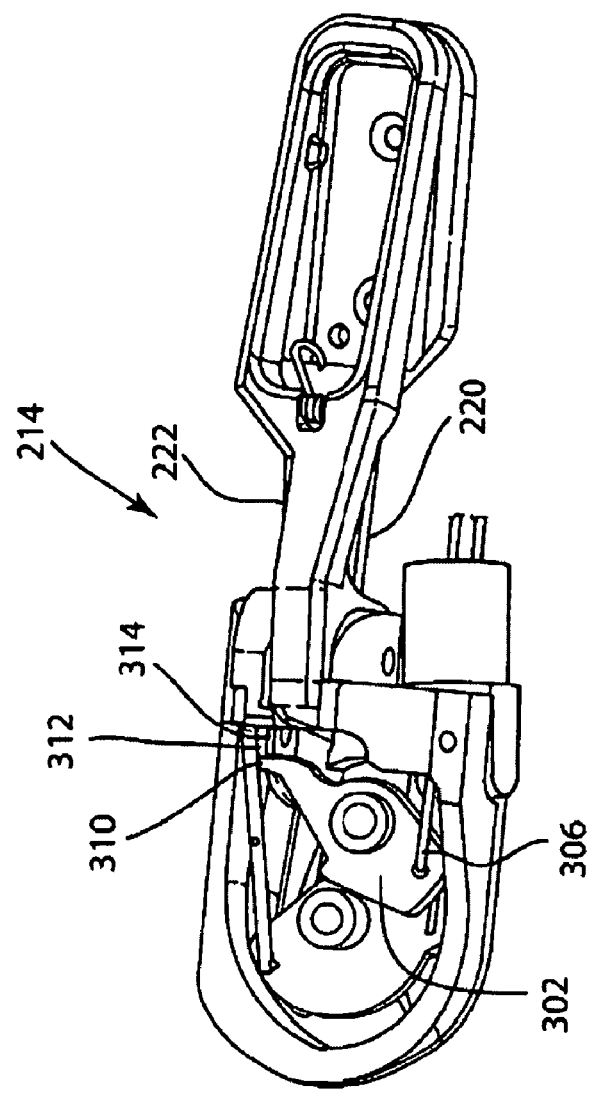
FIG. 37 is a fragmentary, perspective view of the distal end of the instrument of FIG. 36 with the jaws in a closed configuration without a fastener.

Referring now to FIGS. 36 and 37, in the first embodiment, when the jaws are in a closed position and control element 210 is pushed distally relative to the control shaft 206 to apply a pushing force to the second bell crank 302, the push bar 310 is forced against the contact portions 312, 314 and moves the release elements 259, 272 (see FIG. 33) into the respective jaws 226, 228. Such movement effects both a locking together of the male and female parts 12, 14 of the fastener 10 and a release of the fastener 10 from the jaws 226, 228 as set forth in the following text.

First, when the end of release element 272 is pushed against the sliding assembly 52, the sliding assembly 52 is forced to move relative to the latch body 50. This movement locks the catches 96, 98 of the latch lock 72 relative to the posts 32, 34 and, thereby, locks the male and female parts 12, 14 of the fastener together. Second, movement of the latch slide cover 74, opens a space 108 between the slide cover 74 and the latch body cover 56, frees the head 76 of the latch slide 70 from the ledge 275 and frees the catches 262, 264 of the female jaw 228 from the setback 112 (see the aligning space 108 in FIG. 6) to thereby release the female part 14 from the female jaw 228. Third, the U-shaped ends 261, 263 (FIG. 27) of the bifurcated release element 255 are moved out of the bores 46, 48 of the posts 32, 34 to release the male part 12 from the male jaw 226. It is noted that the force on release element 255 is sufficient to overcome the friction created by plates 265, 267.

The push bar 310 is decoupled from the release elements 259, 272 because the contact portions 312, 314 of the release elements 259, 272 will be differently located relative to the push bar 310 based upon whether large or small amounts of tissue are located between the closed jaws 226, 228 and to what degree the jaws 226, 228 are closed. This decoupled adjustable mechanism operates to effect the appropriate amount of movement to the release elements 259, 272 regardless of the exact closed jaw configuration.

Alternatively, rather than use a bell crank system in which control element 208 is placed under tension to close the jaws and control element 210 is placed under compression to operate the lock the fastener parts and release the fastener from the jaws, another system may be used to couple the control elements 208, 210 to the jaws 226, 228 and release elements 259, 272, respectively. For example, each of the control elements may include an end provided with a U-shape in which the end of the control element defines a return extending non-coaxial with but parallel to the remainder of the control element. For example, the U-shaped end of the control element 208 can be coupled to the jaws such that, when the control element 208 is placed under compression, the return portion of the U-shape pulls the jaws closed. Similarly, the U-shaped end of the control element 210 can be configured to act on release elements 259, 272 such that control element is placed under tension to the U-shaped portion pushed on the release elements 259, 272. Other mechanisms may, likewise, be used.

Figure 57:
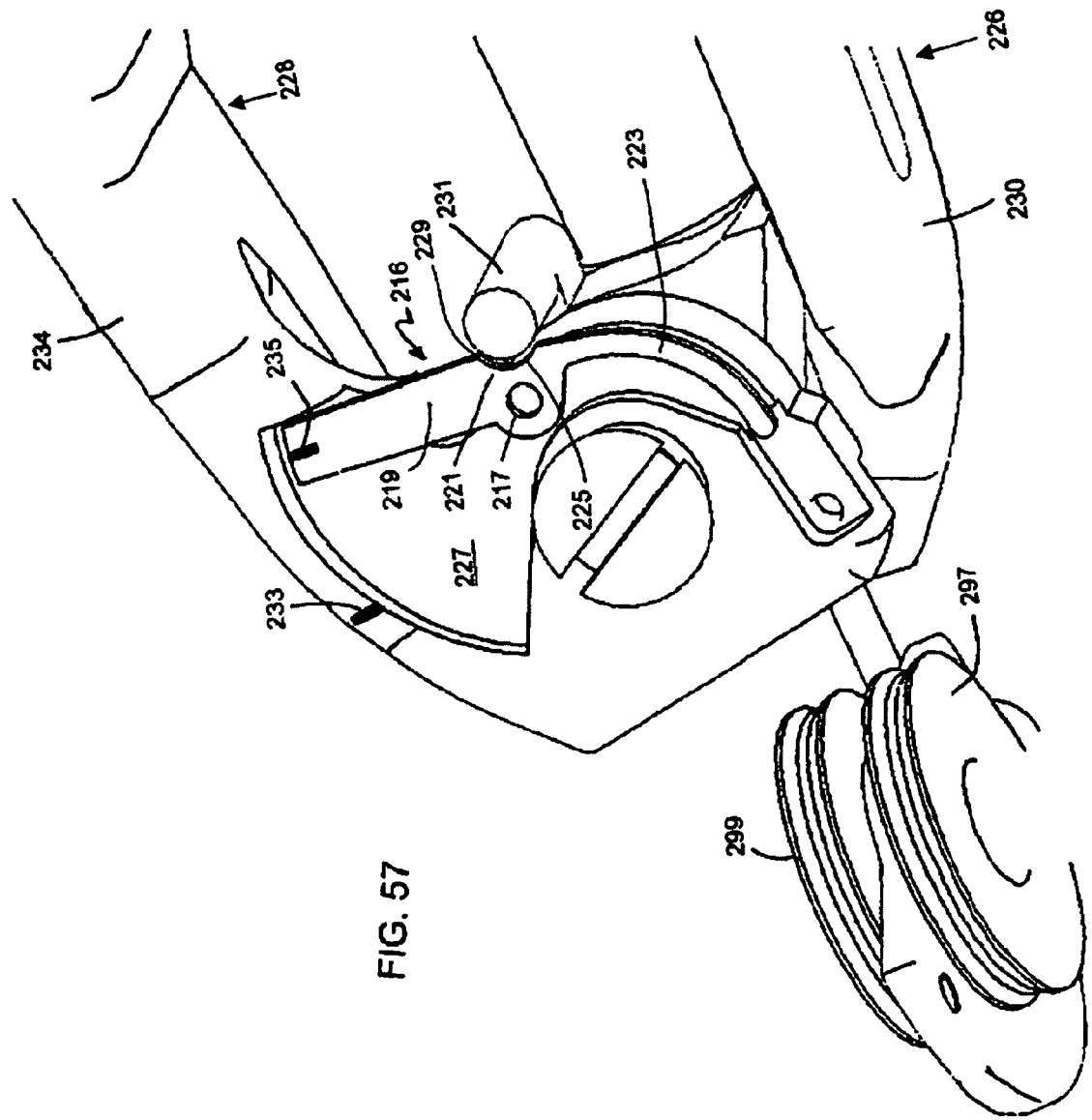
FIG. 57 is a fragmentary, perspective view of an enlarged portion of the distal end of another alternative embodiment of the instrument of FIG. 26 from the side thereof with the jaws in a substantially open, non-aligned implantation position and with portions thereof removed for clarity.
Figure 60:
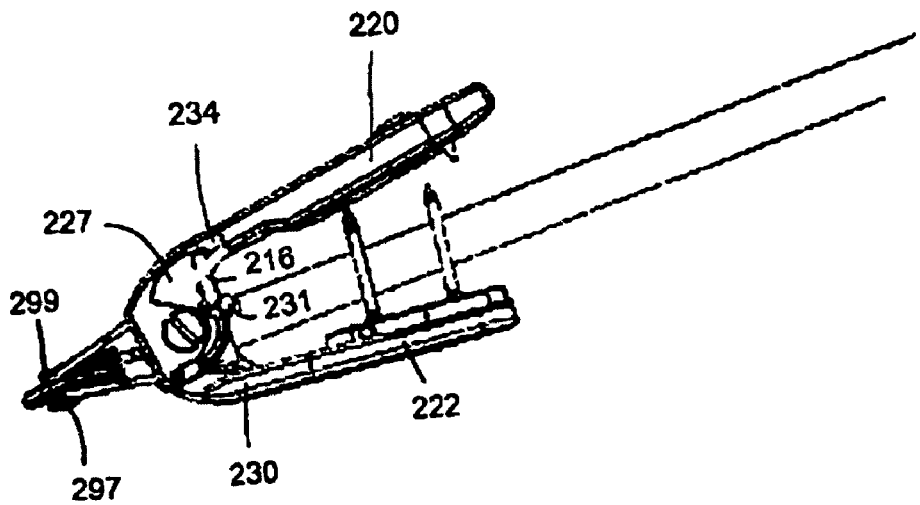
FIG. 60 is a fragmentary, perspective view of the distal end effector of FIG. 59 with the housing removed for clarity.
Figure 61:
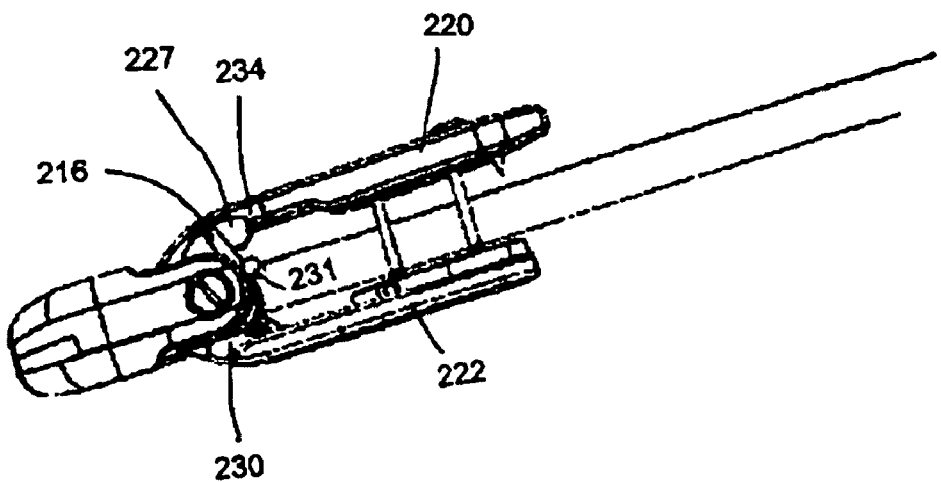
FIG. 61 is a fragmentary, perspective view of the distal end effector of FIG. 58 with the jaws in a closed, aligned implantation position.
Figure 62:
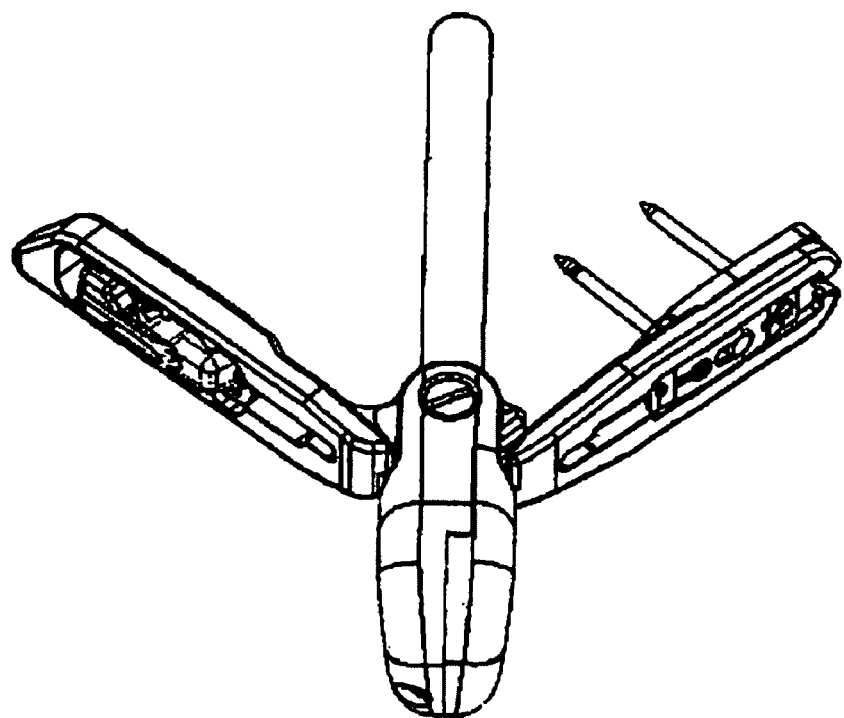
FIG. 62 is a fragmentary, perspective view from the distal end of the distal end effector of FIG. 58.
Figure 63:
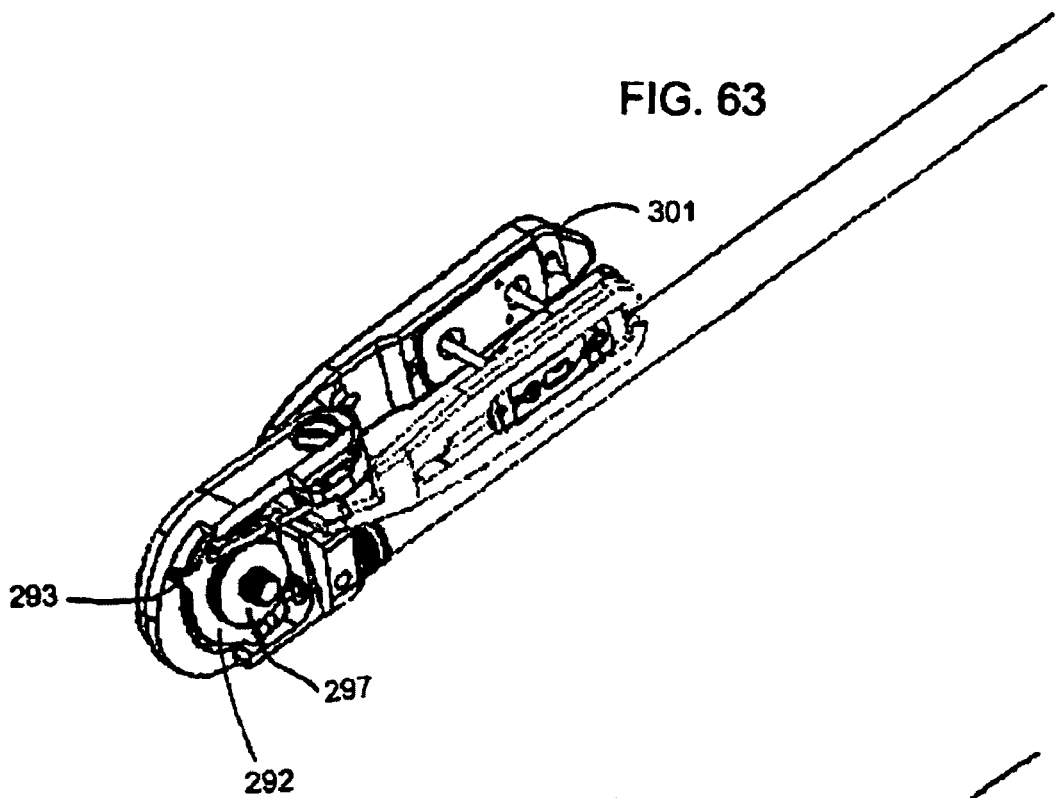
FIG. 63 is a fragmentary, perspective view from above a side of the distal end of a further alternative embodiment of the instrument of FIG. 26 with the jaws in a closed, aligned implantation position holding a fastener of FIGS. 9 and 10 and with a portion of the housing removed for clarity.

The first embodiment of the two bell crank system can also be replaced with a second, preferred, embodiment of a single bell crank and two-pulley system. Such a system is illustrated in FIGS. 57, 60, and 63 and uses a single cable 209' to release both the male and female parts 12, 14 of the fastener 10, with one end of the cable being fixedly connected to a male release assembly in the male jaw 226' (see FIGS. 43 to 45) and the other end of the cable being fixedly connected to a female release assembly in the female jaw 228' (see FIG. 40). A detailed explanation of the second embodiment begins in the following paragraph. The single bell crank in this second system is the same as the bell crank 292 in the first embodiment and can have (but is not required to have) a larger size because there is no need to make room in the housing 290 for a second bell crank. See FIGS. 60 and 63. Accordingly, no further explanation of the bell crank of the second embodiment is necessary. Alternatively, the presence of the single bell crank can allow the end effector housing 202 to be smaller in size.

To apply a single cable system for actuating both the male and female release assemblies, the male and female jaws 226, 228 are formed differently than in the first embodiment. The second embodiment of the female jaw 228' is illustrated in FIGS. 38 to 44.

Figure 38:
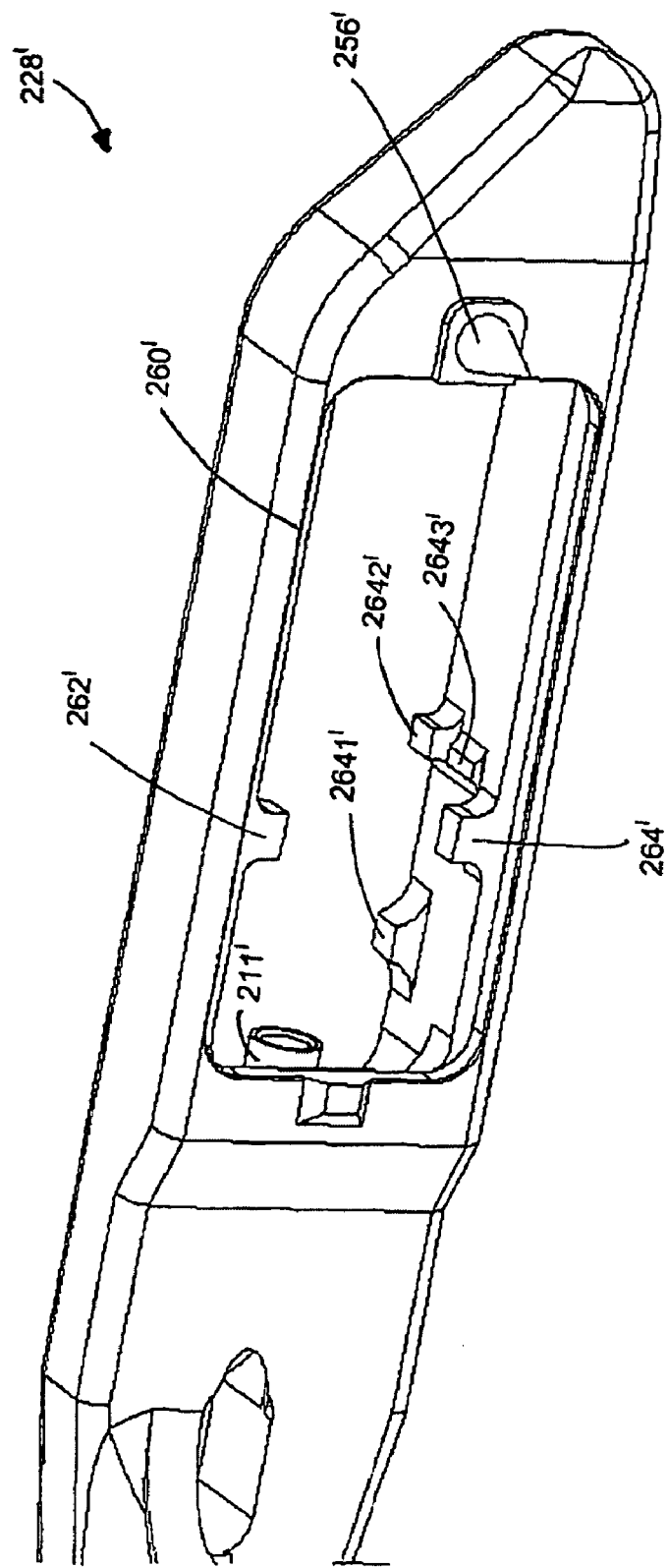
FIG. 38 is a fragmentary, perspective view of an alternative embodiment of the female jaw of FIGS. 27 to 35 from a direction between the jaws.
Figure 39:
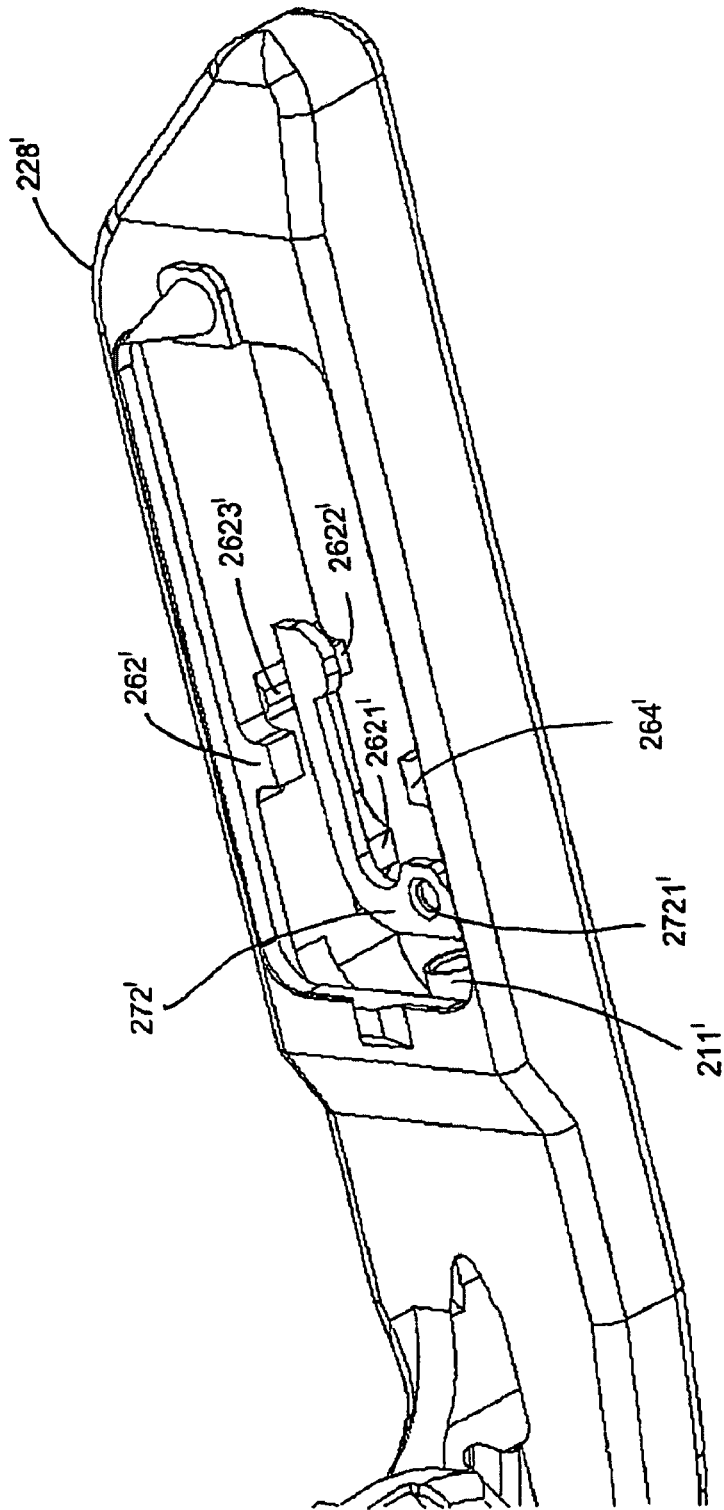
FIG. 39 is a fragmentary, perspective view of the female jaw of FIG. 38 with a portion of a female side control assembly.
Figure 40:
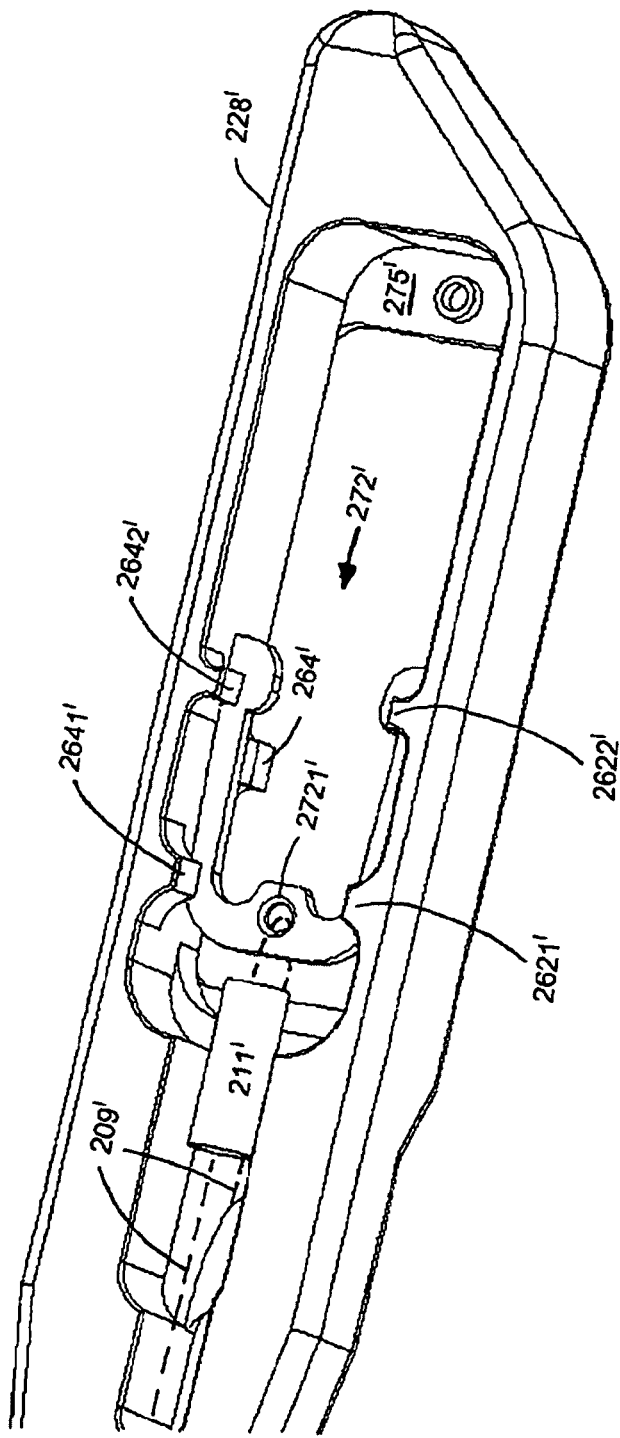
FIG. 40 is a fragmentary, perspective view of the female jaw of FIG. 39 from a direction outside the jaws.

The female jaw 228' includes a relatively large generally rectangular opening 260' sized to receive the latch body cover 56 and latch slide cover 74 of the female part 14 of the fastener 10. The jaw 228' also defines a ledge 275' (FIGS. 40 and 42) and two catches 262', 264' that extend into the opening 260. Also provided near each of the catches 262', 264' are three features similar to the catches. Only one set of these three features is illustrated in FIG. 38; the corresponding set of three features is illustrated in FIGS. 39 and 40. Specifically, two release guides 2621', 2622'; 2641', 2642' are provided on each side of the interior of the female jaw 228' to retain the stirrup 272' of the female release assembly in the jaw 228' as explained in further detail below. Also a single tension rise 2623', 2643' is provided between the respective sets of the catches 262', 264' and the pairs of release guides 2621', 2622'; 264.1', 2642'.

The female release assembly includes the stirrup 282', a cable 209' (mentioned above and illustrated only as dashed lines in FIG. 40), and a cable crimp 211'. The body of the stirrup 282' defines a bore 2721' for receiving therethrough the cable 209'. The cable crimp 211' is a hollow cylinder in the preferred embodiment, but can take any shape or be any device, system, or process that securely fastens the cable 209' to the stirrup 282'. To effect the fastening, the cable 209' is threaded through the crimp 211', then through the bore 2721', and, then, back through the crimp 211'. A crushing force on the exterior of the crimp 211' fixedly clamps the cable 209' to and in the crimp 211', thereby fastening the stirrup 282' to the cable 209'. Accordingly, a proximally directed movement of the cable 209' will pull the stirrup 282' proximally.

Figure 41:
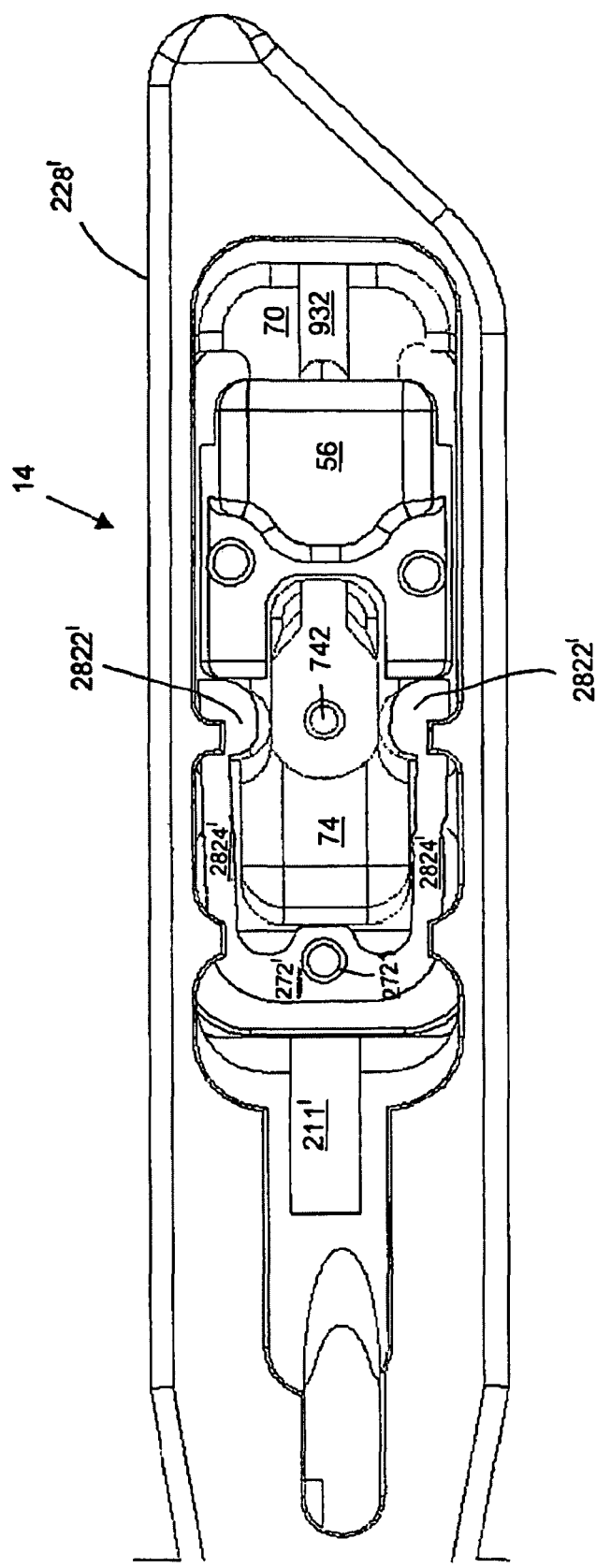
FIG. 41 is a fragmentary, side elevational view of the female jaw of FIG. 40 with a portion of the female part of the fastener disposed therein and with a latch slide of the female part in a first position.
Figure 42:
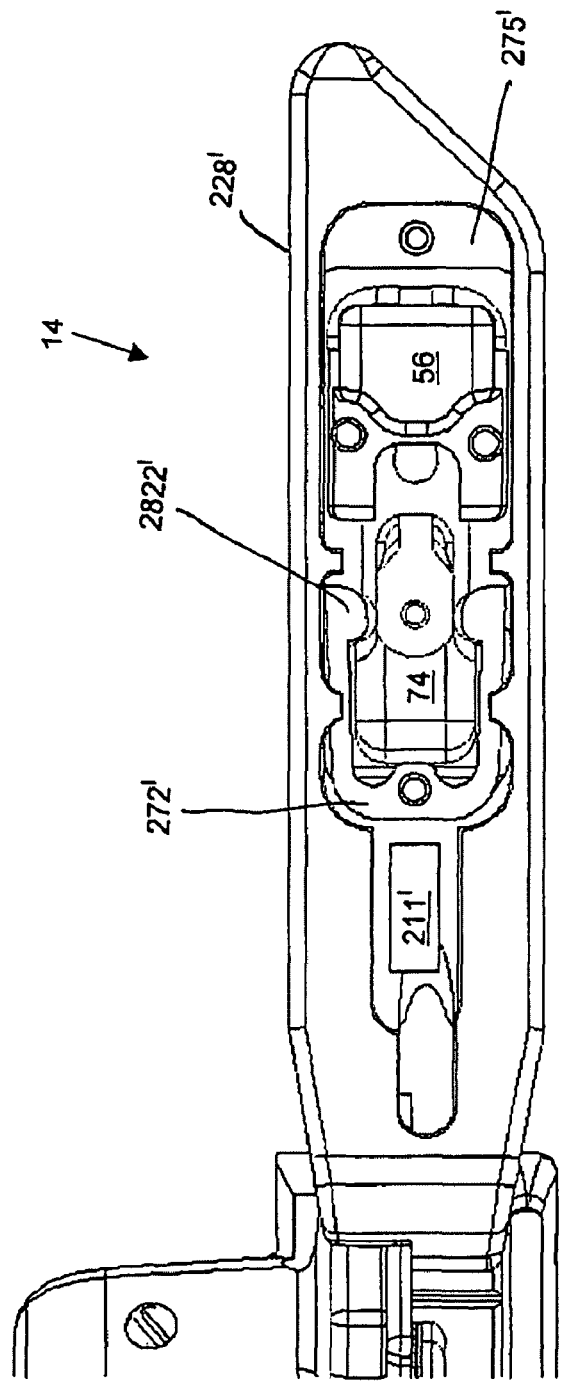
FIG. 42 is a fragmentary, side elevational view of the female jaw of FIG. 41 with the latch slide of the female part in a second position.

The stirrup 282' is shaped to correspond to an exterior of the slide cover 74, as shown in FIGS. 41 and 42. Two protrusions 2822' extend inward towards the slide cover 74 and are shaped to fit within a corresponding groove in the slide cover 74. Preferably, the protrusions 2822' and the grooves are hemispherical in shape. The protrusions 2822' are thicker (in a direction orthogonal to the plane of FIGS. 41 and 42) than the remainder of the stirrup 282'. The tension rise 2623', 2643' is provided to contact outer side surfaces of the stirrup 282' in any position of the stirrup 282'. The tension rise 2623', 2643' acts to force each of the arms 2824' slightly inwards. This force allows the stirrup 282' to grab the slide cover 74' better and holds the stirrup 282' in position within the female jaw 228'. After the fastener 10 is released from the jaws 226', 228', the tension rise 2623', 2643' prevents the stirrup 282' from falling out of the female jaw 228' and places no load upon the female part 14 after actuation of the male and female release assemblies.

A tissue piercing post 256' is provided approximately at the terminus of the female jaw 228 (which post has a preferred conical shape ending with a relatively sharp point).

The female part 14 is inserted into the jaw 228' in its locked position—the latch slide 70 is in the position shown in FIG. 42 with the stirrup 272' surrounding the slide cover and the bottom surface of the base portion 54 being approximately flush with the inner surface of the female jaw on which the tissue piercing post 256' is disposed. Then, while the female part 14 rests inside the female jaw 228', the slide cover 74 is moved distally, into its unlocked position, taking with it the latch slide 70 so that the head 76 of the latch slide 70 (FIG. 5) lies over the ledge 275' (as shown in FIG. 41). As referred to herein with respect to the male and female jaws 226', 228', the inside of each jaw 226', 228' is the side facing towards the opposite other jaw 228', 226' and the outside of each jaw 226', 228' is the side facing away from the opposite other jaw 228', 226'.

Figure 43:
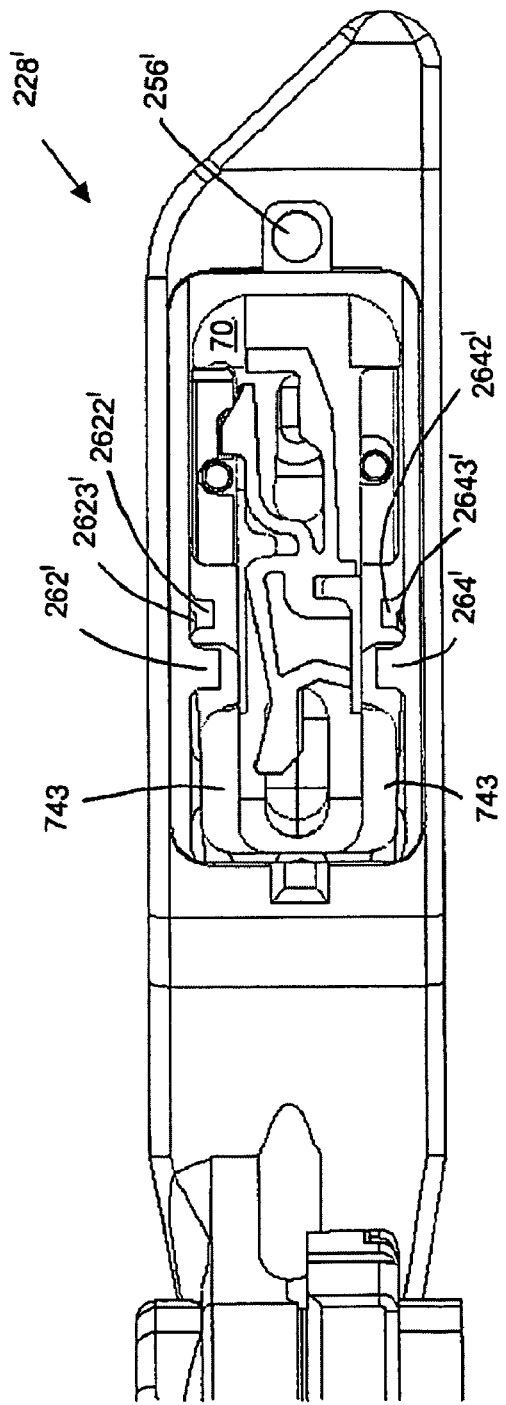
FIG. 43 is a fragmentary, side elevational view of the female jaw of FIG. 39 from a direction between the jaws with the latch slide of the female part in the second position.
Figure 44:
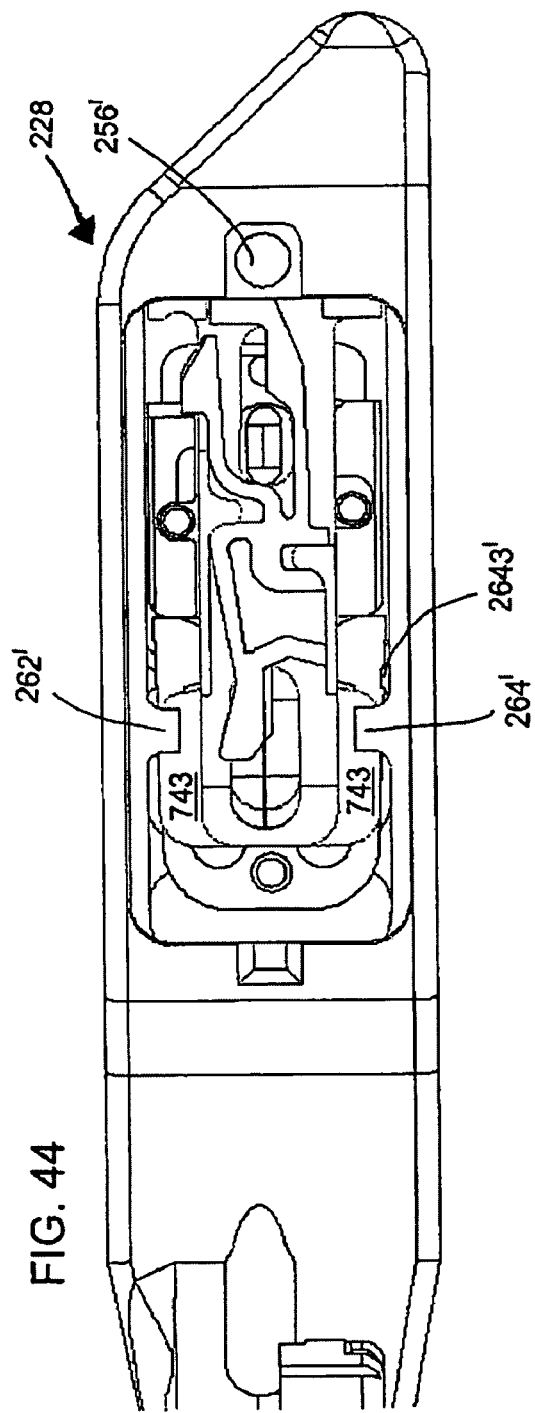
FIG. 44 is a fragmentary, side elevational view of the female jaw of FIG. 43 with the latch slide of the female part in the first position.
Figure 45:
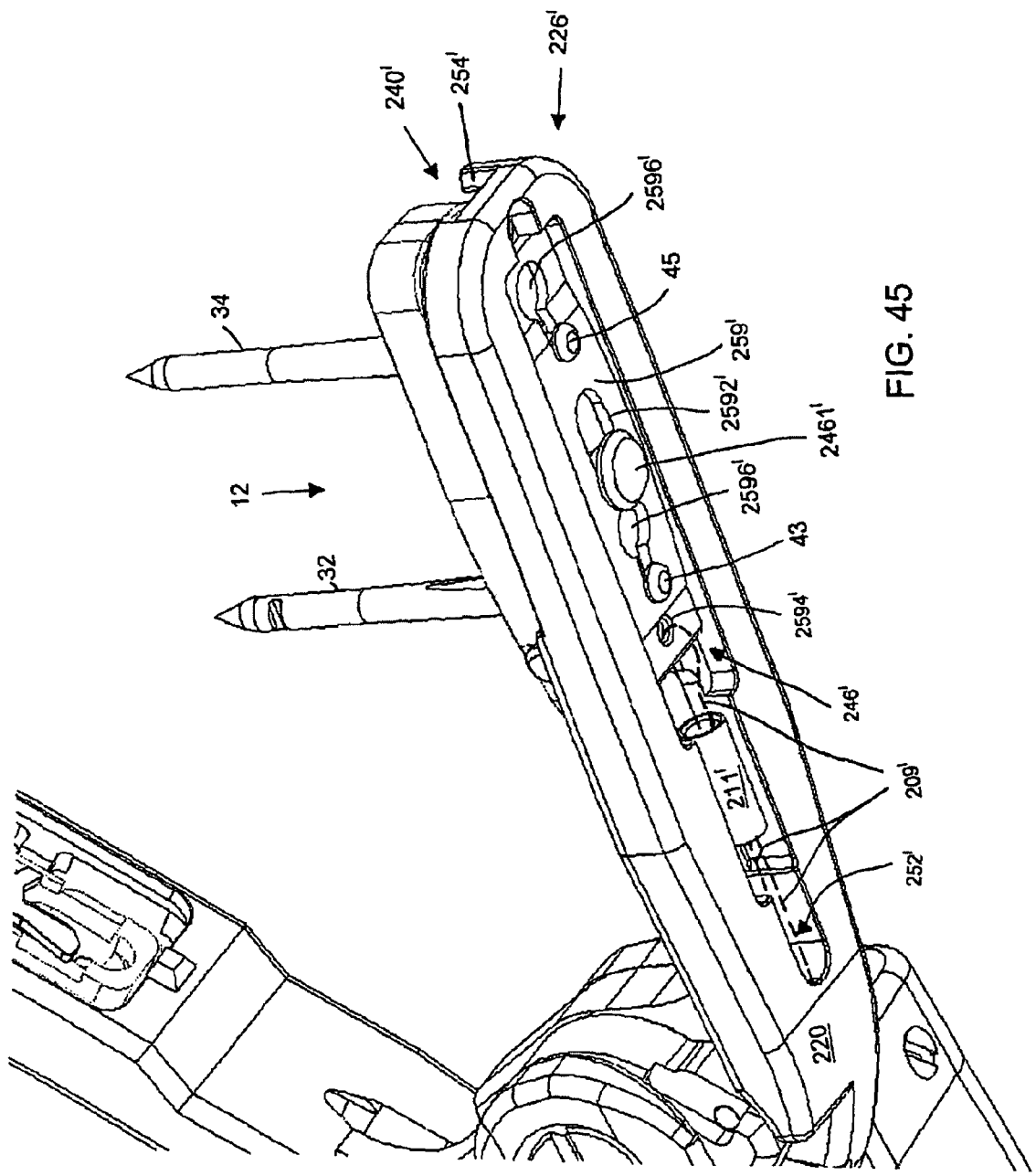
FIG. 45 is a fragmentary, perspective view of an alternative embodiment of the male jaw of FIGS. 27 to 35 from a direction outside the jaws with a release slide in a first position.
Figure 46:
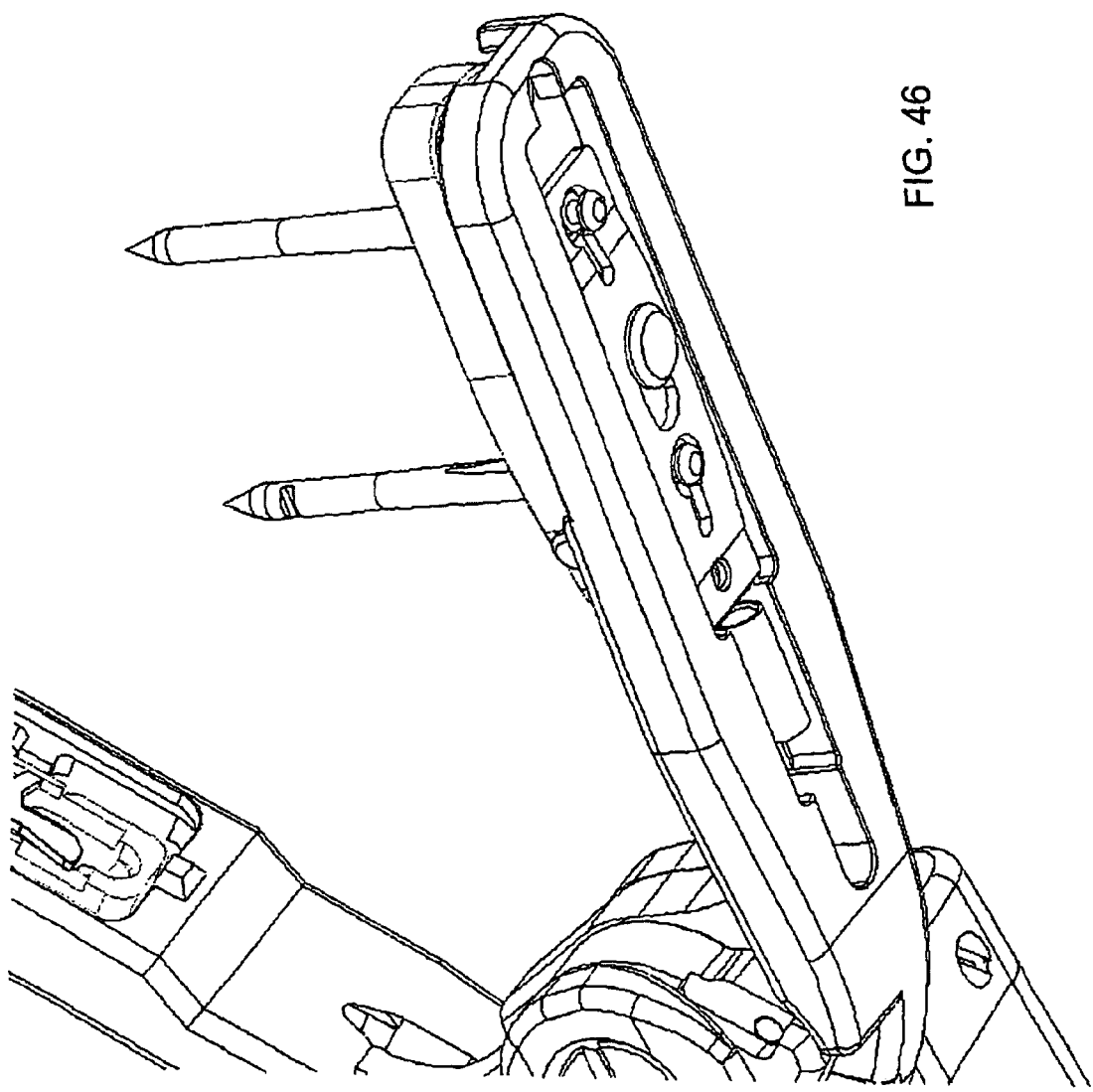
FIG. 46 is a fragmentary, perspective view of the male jaw of FIG. 45 with the release slide in a second position.

Such movement causes the female part 14 to be locked in the female jaw 228' in two ways. First the extension of the latch slide 70 over the ledge 275' creates a connection that prevents the female part 14 from moving in a direction towards the male jaw 226' (in a direction from the inside of the female jaw 228' along the protruding extent of the tissue piercing post 256', as shown in FIG. 41). The slide cover 74 has two wings 743 projecting away from respective opposite sides thereof. See FIG. 9. The wings 743 and the base portion 54 together form a groove (see setback 112 in FIG. 5) into which the catches 262', 624' rest when the slide cover 74 is moved to place the latch slide 70 over the ledge 275'. In such a position, the wings 743 and the base portion 54 substantially prevent any lateral or longitudinal movement of the female part 14. Therefore, the groove-catch connection forms the second locking measure for the female part 14. FIGS. 43 and 44 are provided to better illustrate the connection between the wings 743 and the catches 262', 264'. These figures, however, show the female part 14 with the base portion 54/top parts of the slide cover 74 and the cover portion 56 removed.

As shown in FIG. 43, the female part 14 is inserted in the female jaw 228' in its locked position. FIG. 43 clearly shows that the wings 743 do not overlap the catches 262', 264'. Therefore, the female part 14 is free to be removed from the opening 260' in a direction towards the viewer of FIGS. 43 and 44. Extending the latch slide 70 over the ledge 275' (to the right of FIGS. 43 and 44) correspondingly moves the wings 743 distally (also to the right of FIGS. 43 and 44). After such movement, as shown in FIG. 44, the wings 743 overlap the catches 262', 264' and, therefore, entirely prevent removal of the female part 14 from the female jaw 228'.

Like the first embodiment, the inside surface of the male jaw 226' includes a recess 240' adapted to receive the rear or back of the male part 12 of the fastener 10. The recess 240' also includes two throughbores 242', 244' that pass entirely through to the outside surface of the male jaw 226'. See FIG. 29. Referring to FIGS. 29 and 45 to 47, when the male part 12 is loaded into and held within the recess 240' of the male jaw 226', at least the lower portions 43, 45 of the posts 32, 34 are received in the throughbores 242', 244'. Such a configuration retains the posts 32, 34 upright and, consequently, prevents their rotation into a collapsed configuration. The second embodiment of the male jaw 226' also provides a recess 246' at the outside of the male jaw 226' through which the lower portions 43, 45 of the posts 32, 34 protrude when received in the throughbores 242', 244'. The recess 246' also is in communication with an exit opening 252' passing through the first arm 220 and through which is supplied an end of the cable 209' opposite the end terminating in the female jaw 228' for actuating the release assembly in the male jaw 226'.

The terminal end of the male jaw 226 also defines a groove 254'. Referring to FIGS. 38, 39, and 45 to 47, when the female and male jaws 226', 228' are free of the fastener parts 12, 14 and are closed past parallel (e.g., after the fastener 10 has been released and during retraction of the instrument from the stomach), the post 256' resides in the groove 254' of the male jaw 226' to provide a more tapered configuration and aid in removal of the instrument from the patient. Also, the ends of each jaw 226', 228' have a tapered configuration to enhance easy removal of the instrument from the patient. This is true, in particular, for the distal end of the female jaw 228' shown in FIGS. 38 to 44.

Figure 47:
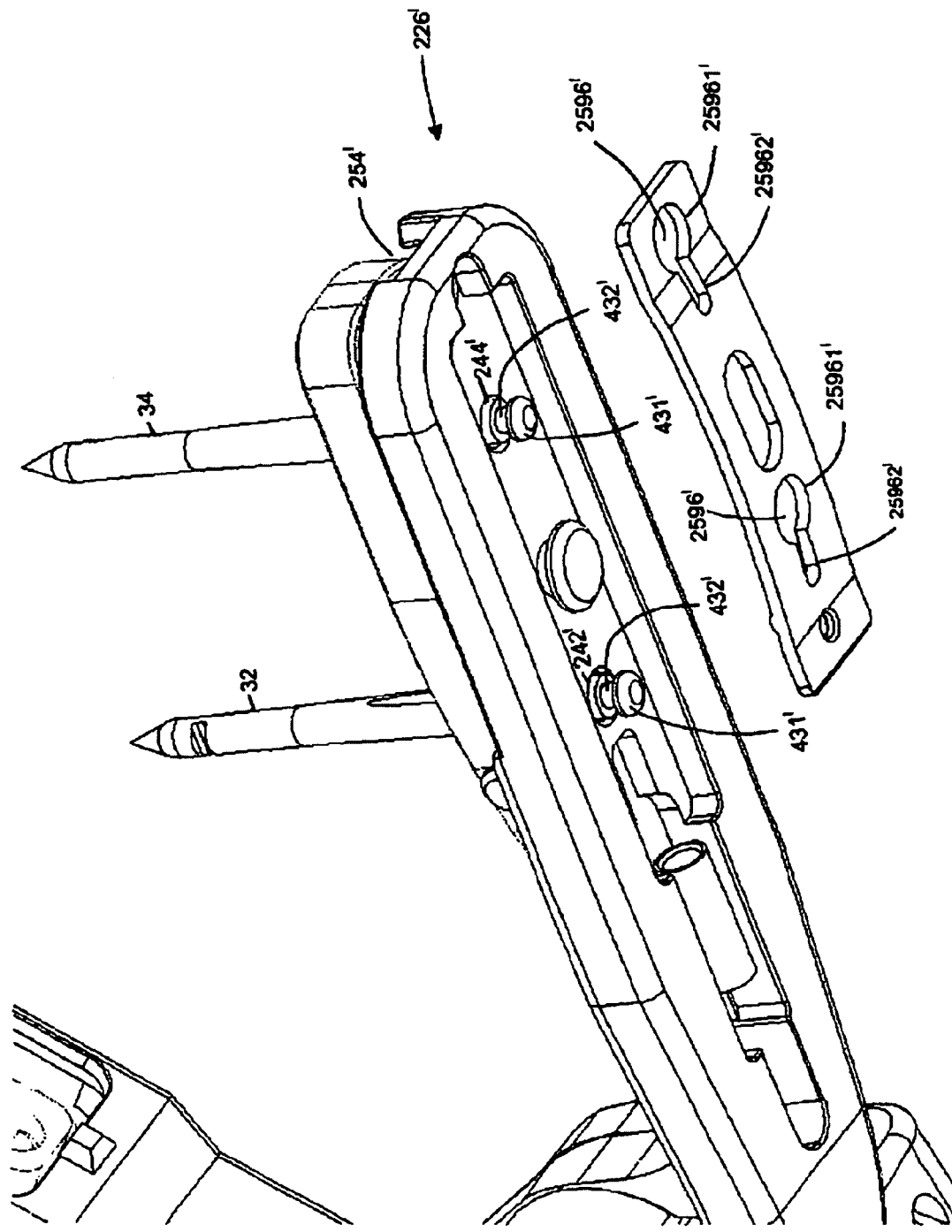
FIG. 47 is a fragmentary, perspective view of the male jaw of FIG. 46 with the release slide in an exploded view.
Figure 48:
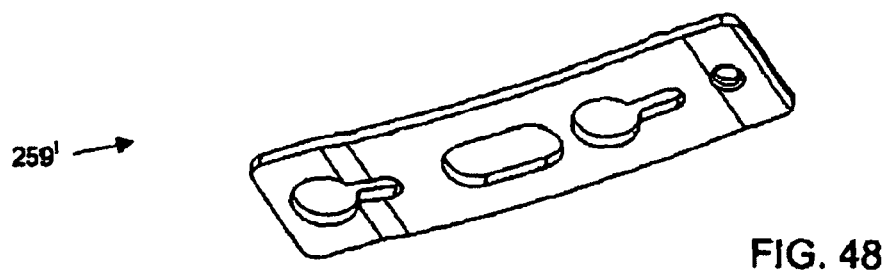
FIG. 48 is a perspective view of the release slide of FIGS. 46 and 47 from above.
Figure 49:
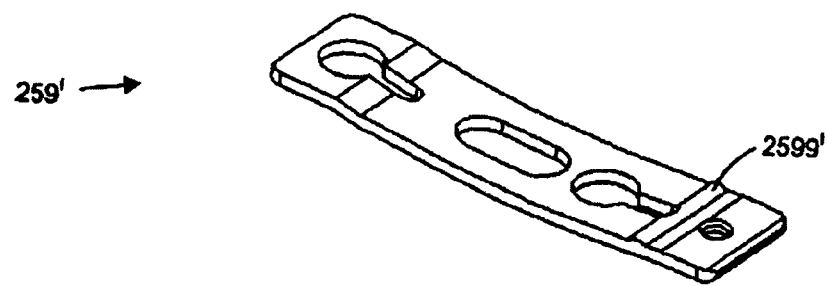
FIG. 49 is a perspective view of the release slide of FIG. 48 from below.
Figure 50:
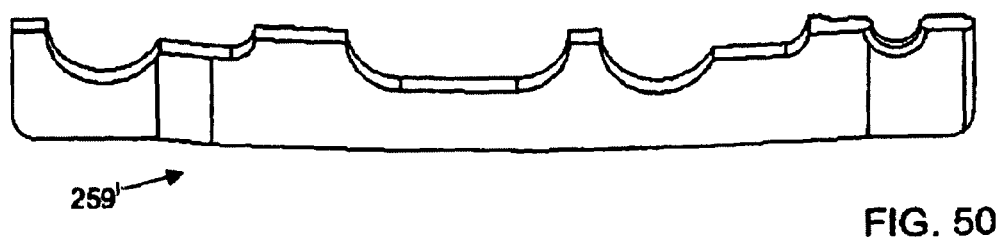
FIG. 50 is a fragmentary, perspective view of a cross-section of the release slide of FIG. 48.
Figure 51:
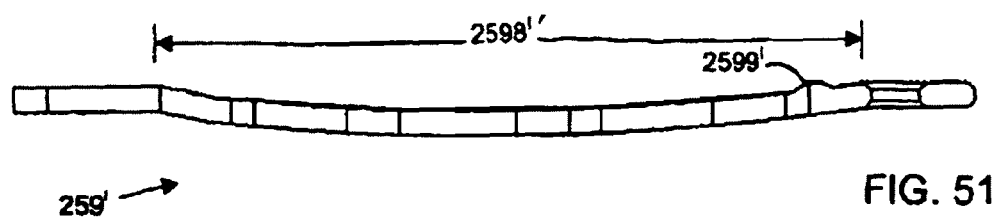
FIG. 51 is a side elevational view of the cross-section of the release slide of FIG. 50.

While placement of the lower portions 43, 45 of the posts 32, 34 into the throughbores 242', 244' holds the male part 12 in the male jaw 226', it does not securely attach the male part 12 in the male jaw 226' such that the male part 12 is locked to the male jaw 226'. The second embodiment of the male jaw 226', therefore, includes a post release slide 259' for releasably locking the male part 12 in the male jaw 226'. The recess 246' in the outside of the male jaw 226' has a fastening post 2461', which is best shown in FIG. 47, for securing the slide 259' within the recess 246'. The fastening post 2461' has a mushroom shape and is secured to the recess 246' somewhere between the throughbores 242', 244'. This, however, is only one exemplary location for securing the post 2461'.

In the preferred configuration, a third non-illustrated throughbore halfway between the throughbores 242', 244' extends from the inside recess 240' to the outside recess 246' and is used to receive the post 2461' in the manner of a rivet. In other words, a non-illustrated shaft of the post 2461' passes through the post release slide 259' without substantial friction and a portion of the post 2461' protruding into the recess 240' (which portion is somewhat malleable) is deformed to capture permanently the post 2461' in place. Alternatively, the third throughbore can have a female thread and the shaft of the post 2461' can have a corresponding male thread to allow the post 2461' to screw tightly in place.

To fasten the slide 259' to the male jaw 226', the shaft of the post 2461' is inserted through a bore 2592' in the slide 259' and is, then, secured to the male jaw 226', preferably, in the third throughbore. Such a connection does not clamp the central portion of the slide 259' to the surface of the recess 246'. Instead, there is a substantial amount of play between the top and bottom surfaces of the slide 259' surrounding the bore 2592' and the corresponding holding surfaces formed by the bottom surface of the recess 246' and the underside of the mushroom shaped formed by the head of the post 2461'. This loose connection allows the slide 259' to travel parallel to the longitudinal axis of the male jaw 226' between a distal-most position shown in FIG. 45 and a proximal-most position shown in FIG. 46.

Sliding of the post release slide 259' between the distal-most and proximal-most positions occurs by attaching the cable 209' to a bore 2594' formed in the proximal end of the slide 259'. The cable connection to the slide 259' is similar to the cable connection to the stirrup 272'. The cable 209' is threaded through the crimp 211', then through the bore 2594', and, then, back through the crimp 211'. A crushing force on the exterior of the crimp 211' fixedly clamps the cable 209' to and in the crimp 211', thereby fastening the slide 259' to the cable 209'. Accordingly, a proximally directed movement of the cable 209' will pull the slide 259' proximally. Such movement will effect the unlocking of the male part 12 of the fastener 10.

As set forth above, placement of the lower portions 43, 45 of the posts 32, 34 into the throughbores 242', 244' merely holds the male part 12 in the male jaw 226', it does not securely attach the male part 12 in the male jaw 226'. Locking of the male part 12 is performed by providing two keyholes 2596' in the slide 259'. These keyholes 2596' are placed such that a larger opening 25961' of each keyhole 2596' has a central axis that is aligned substantially with a central axis of the throughbores 242', 244' when the slide 259' is in a proximal-most position (shown in FIG. 46) and such that the smaller opening 25962' of each keyhole 2596' has a centerline that intersects a central axis of the throughbores 242', 244' when the slide 259' is in a distal-most position (shown in FIG. 45).

The diameter of the larger opening 25961' is at least as large as the greatest diameter of the head 431' of the end portion 43, 45 of the posts 32, 34 so that the lower portions 43, 45 are not restricted in movement in the throughbores 242', 244' when the slide 259' is in a proximal-most position. In contrast, the diameter of the smaller opening 25962' is smaller than the smallest diameter of the head 431' of the end portion 43, 45 of the posts 32, 34 and is at least as large (no smaller than) as the greatest diameter of the shaft 432' connecting the head 431' of the end portion 43, 45 to the post 32, 34 so that the end portions 43, 45 are captured by the slide 259' when the slide 259' is in any position that is distal of the proximal-most position.

Simply put, when the slide 259' is in the proximal-most position (FIG. 46), lower portions 43, 45 of the posts 32, 34 are free to move within the throughbores 242', 244' (male part 12 is unlocked), and, when the slide 259' is in a position more distal than the proximal-most position, the smaller opening 25962' of the keyhole 2596' engages both lower portions 43, 45 of the posts 32, 34 to lock the male part 12 in the male jaw 226'. FIG. 47 illustrates the operative connection between the slide 259' and the posts 32, 34 with the slide 259' separate from the male jaw 226'. FIGS. 48 to 52 show various aspects of the slide 259'. It is apparent in these figures that the slide 259' is not flat. A middle portion 2598' is bowed to form a plate spring that imparts a bias against the lower portions 43, 45 of the posts 32, 34 when the head 431' is engaged in the smaller opening 25962' of the keyhole 2596'. Also provided on a side of the slide 259' facing the male jaw 226' is a protrusion 2599', which serves as a frictional detent to help secure the slide 259' in the latched condition.

Based upon the above-described second embodiment of the male and female jaws 226', 228', to actuate an unlocking of the fastener 10 therefrom, the cable 209' only needs to be pulled slightly in a proximal direction with respect to each of the male and female jaws 226', 228', which pulling effects a corresponding proximal (unlocking) movement of both the stirrup 272' and the slide 259'.

To understand how a single cable 209' can effect a simultaneous movement of both the stirrup 272' and the slide 259', the control elements 208, 210, 294, 302, 300, 312 are modified in the second embodiment. In comparison with the two bell crank system having two control elements 208, 210 through the control shaft 206, the second embodiment has three control elements running through the control shaft 206: a single control rod 208 and two extents of the looped cable 209'. The route of the single male and female release cable 209' is as follows: the cable 209' has one end attached to the post release slide 259' in the male jaw 226' and extends into the end effector housing. The cable 209' travels around a first pulley 297 in a counter-clockwise manner with respect to FIGS. 57 and 63, passes entirely through the longitudinal extent of the control shaft 206 in a proximal direction, and exits the proximal end of the control shaft 206 for a predefined distance. The cable 209' is formed into a loop to enter the proximal end of the control shaft 206 and travel entirely through the longitudinal extent of the control shaft 206 in a distal direction. The cable 209', then, wraps around a second pulley 299 in a clockwise manner with respect to FIGS. 57 and 63, extends through the end effector housing 202 towards the female jaw 228', and is fixedly connected to the stirrup 272' in the female jaw 228'.

As set forth above, to actuate an unlocking of the fastener 10 from the jaws 226', 228', the cable 209' only needs to be pulled slightly in a proximal direction with respect to the jaws 226', 228'. A proximally directed force upon the loop of the cable 209', therefore, effects the needed proximal (unlocking) movement of both the stirrup 272' and the slide 259'.

Because there is a loop of cable 209' at the proximal end of the control shaft 206, the proximal actuation handle 204 can be provided with a fastener actuator (e.g., slide lever 364, 365 in FIGS. 26 and 67) incorporating a third pulley 3428 (see FIG. 74) similar to pulleys 297, 299. When the loop of the cable 209' is wrapped around the third pulley 3428 with relatively little slack, a small proximal movement of the fastener actuator 364, 365 pulls each portion of the cable 209' extending through the control shaft 206 equally and in a self-balancing manner. Therefore, both the post release slide 259' in the male jaw 226 and the stirrup 272' in the female jaw 228 are actuated simultaneously. A detailed embodiment for pulling the loop will be described below with respect to a preferred alternative embodiment of the proximal actuation handle.

In contrast to the fastener-actuating push system of FIGS. 35 and 36, the two pulley fastener-actuating system of FIGS. 57, 60, and 63 is a pull system.

Throughout the detailed description, the jaw assembly 218 is referred to as being in a "closed" position, as shown, for example, in FIG. 36, indicating that the male 12 and female 14 portions of the fastener 10 are in an optimal position for connecting together. When the end effector 202 is in vivo, however, it is difficult, even with a clear endoscopic picture, for the user to determine that the first and second arms 220, 222 are in the best position for fastener 10 implantation. It is, therefore, desirable to give the user a better measure of such alignment than merely the feel from reaching a perceived final closing position of the arms 220, 222, which, possibly, could be in an under-rotated position such that the male 12 and female 14 portions of the fastener 10 are not best aligned.

Figure 53:
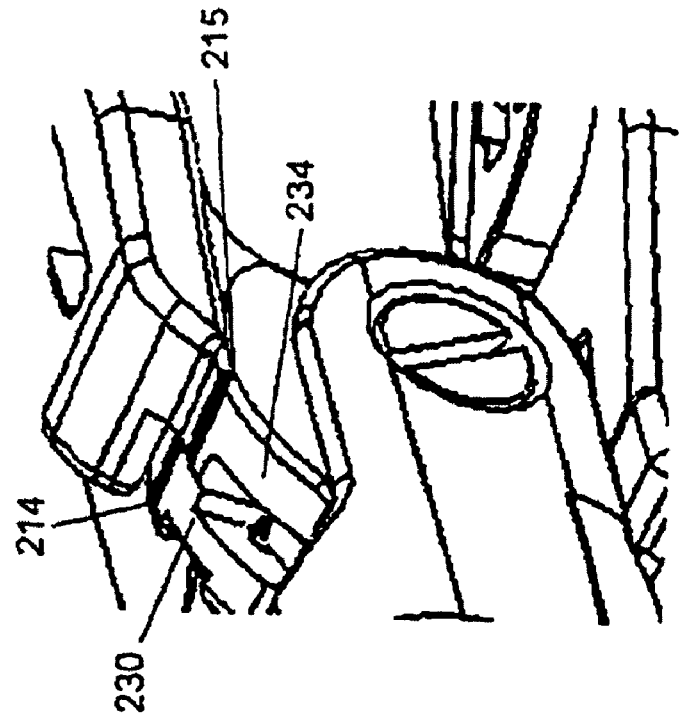
FIG. 53 is a fragmentary, perspective view of an enlarged portion of the distal end effector of FIG. 52.
Figure 52:
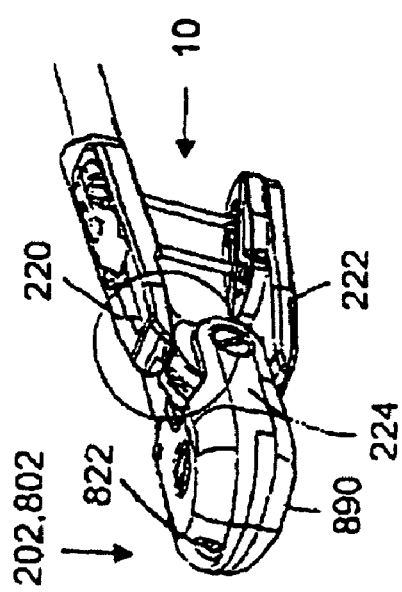
FIG. 52 is a fragmentary, perspective view from above a side of an alternative embodiment of the distal end effector of FIG. 26 in a non-aligned implantation position.
Figure 55:
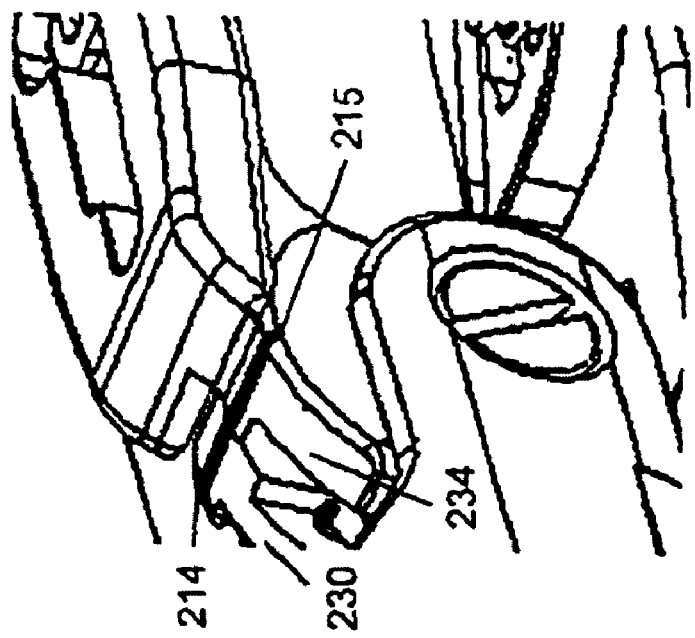
FIG. 55 is a fragmentary, perspective view of an enlarged portion of the distal end effector of FIG. 54.
Figure 54:
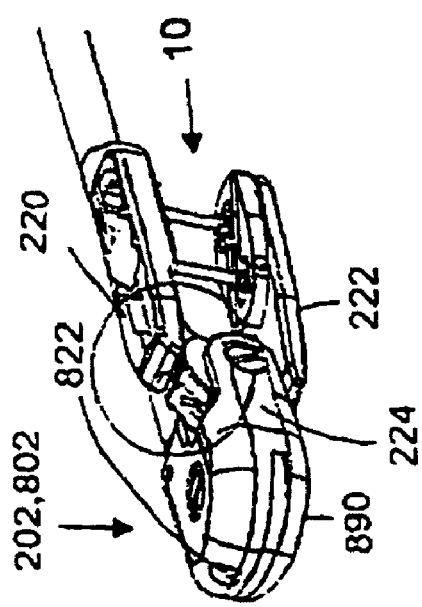
FIG. 54 is a fragmentary, perspective view from above the side of the distal end effector of FIG. 52 in an aligned implantation position.

To provide the user with such a measure of confidence, a first embodiment of markers is illustrated in FIGS. 52 to 55 where each tang 230, 234 is provided with an alignment marker 214, 215. FIGS. 52 to 66 illustrate a preferred embodiment of the end effector 202, described in more detail below, where FIG. 52 shows the effector 202 having the jaws 226, 228 in an unaligned position (where the male 12 and female 14 portions are not in a position in which it is desirable to be connected to one another). In the first marker embodiment, each tang 230, 234 has a respective alignment marker 214, 215. See also FIG. 28. The markers 214, 215 can be disposed on the top side of the tangs 230, 234, as viewed in FIGS. 28 and 52, or on a bottom side thereof (a view that is not illustrated in the drawings), or on both the top and bottom sides thereof. FIG. 53 is an enlarged view of a portion of the tangs 230, 234 and similarly illustrates the markers 214, 215 in the unaligned position. Accordingly, the user knows that the fastener 10 should not be locked at the present position of the arms 220, 222. As can be clearly seen in FIGS. 52 and 53, the alignment markers 214, 215 help determine visually if the arms 220, 222 are aligned with one another for assisting the user in determining when to lock the fastener 10.

Figure 56:
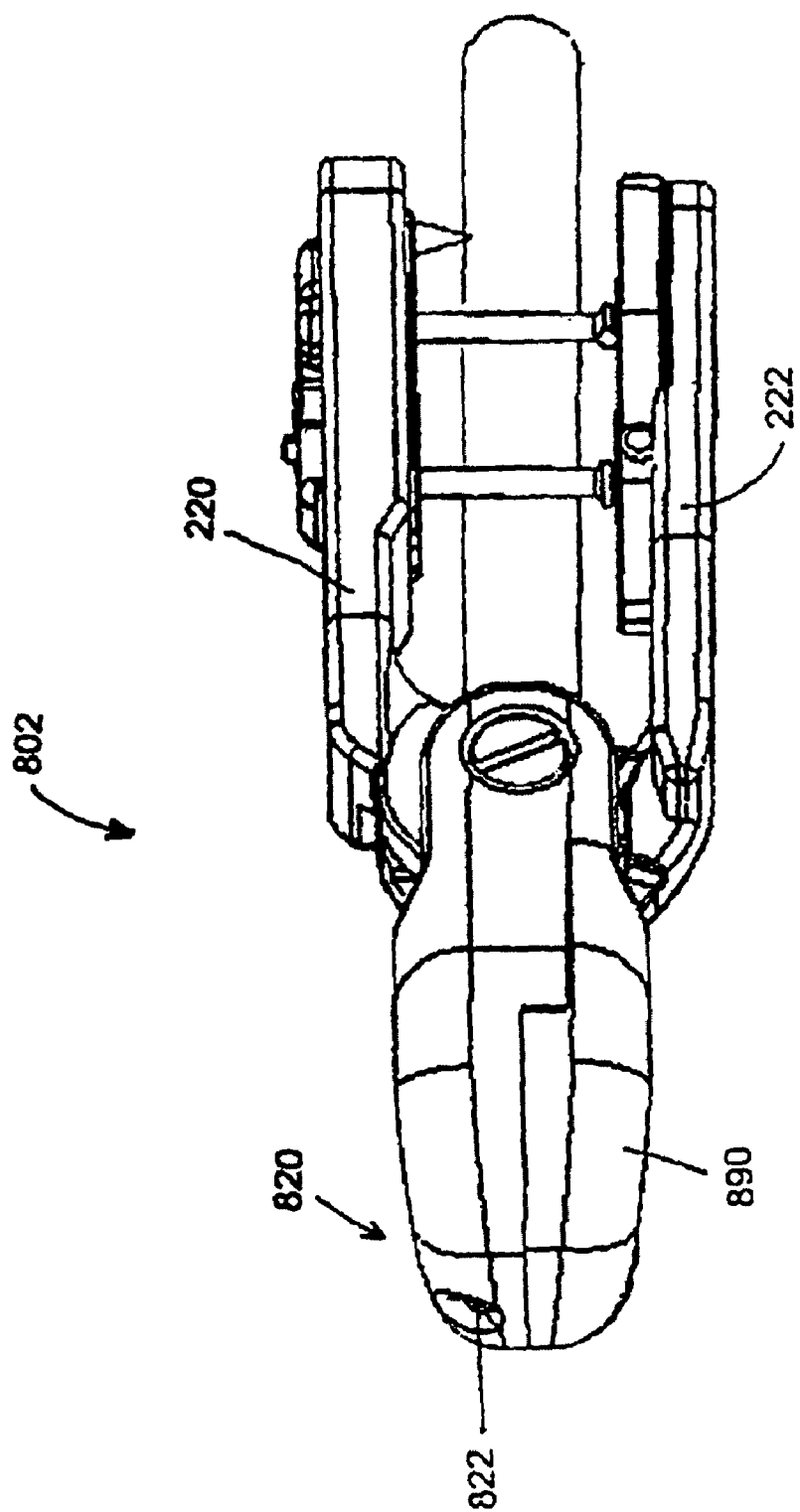
FIG. 56 is a fragmentary, perspective view from a side of the distal end effector of FIG. 54.

In comparison with FIGS. 52 and 53, FIGS. 54 to 56 show the arms 220, 222 in a position in which the alignment markers 214, 215 are aligned with one another, a condition indicating to the user that the jaws 226, 228 are in a position in which fastener 10 can be locked. FIG. 56 clearly illustrates the two jaws 226, 228 substantially parallel to one another. The alignment markers 214, 215, provide the user with a visual cue that the fastener 10 is in the position to be locked. The alignment markers 214, 215 are visible clearly to the user through the endoscope 400 and provide the user, during movement of the jaw assembly 218, with continuous visual feedback as to the position of the arms 220, 222 while they are being closed and/or opened. The use of the alignment markers 214, 215, therefore, ensures the accuracy of the positioning and locking of the fastener 10. In other words, the alignment markers 214, 215 reduce the probability of implanting an improperly positioned fastener, increase the success rate of the related endoscopic procedure, and decrease the rate of repetitive procedures for repositioning or removing the fastener 10. In FIGS. 52 to 55, the alignment markers 214, 215 are shown as horizontal lines. The horizontal lines, however, are merely one example of the many possible configurations for the alignment markers 214, 215. For example the lines do not have to extend fully across the arms 220, 222, and/or they can be two arrows (see FIG. 36), triangles, or other asymmetric indicator pointing towards one another, and/or they can be made to illuminate when in exact alignment. The alignment markers 214, 215 can be colored, for example, printed or painted by dyes, pigments, stains, paints, and/or any other adhesive material, on the arms and, in particular, printed or painted with a fluorescent or highly reflective material. Yellow and orange are preferred colors for the markers. Alternatively, and/or additionally, the alignment markers 214, 215 can be machined, etched, and/or lasered into or onto the arms 220, 222 in the form of recesses or scribe marks.

In the first marker embodiment described above, the alignment markers 214, 215 are disposed on the tangs 230, 234 of the arms 220, 222. During an endoscopic procedure, however, it is possible for the endoscope to be positioned such that the portions of the arms 220, 222 on which the markers 214, 215 are placed are not visible or are not clearly visible to the user. Accordingly, second and third marker embodiments are proposed and are illustrated, respectively, in FIGS. 57 to 61 and FIGS. 63 to 66.

In the second marker embodiment, most clearly shown in FIG. 57, a pivot post 231 is connected fixedly to the male jaw 226. The post 231 can be machined with the male jaw 226, can be attached to the jaw 226 by welding or other fastening measures, or can be pressed into the jaw 226 through a non-illustrated press-lit bore, for example. A marker flag 216 is pivotally connected to the female jaw 228 at a pivot point, which, in a preferred embodiment, is a post or pin integral with the female jaw 228 and adapted to project through a bore 217 in the flag 216 when the flag 216 is connected to the female jaw 228. The flag 216 has an indicator section 219, a pivot section 221, and a follower section 223, which, together, form a guide surface for the post 231. The pivot section 221 includes the bore 217 and has a rotation multiplier 225, preferably, in the form of a notch.

Figure 58:
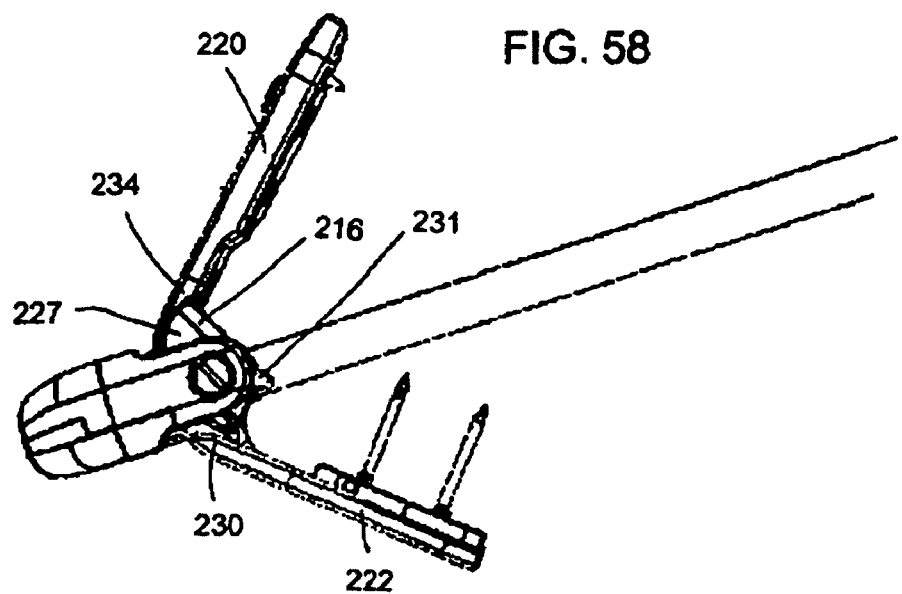
FIG. 58 is a fragmentary, perspective view from the side of the distal end effector of FIGS. 52 to 57 with the jaws in a substantially open, non-aligned implantation position holding therein a fastener of FIGS. 9 and 10.
Figure 59:
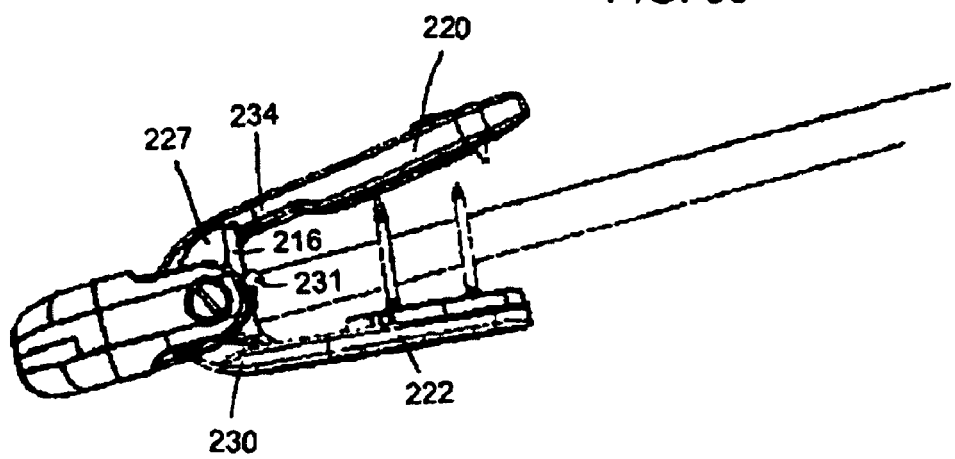
FIG. 59 is a fragmentary, perspective view of the distal end effector of FIG. 58 with the jaws in a partially open, non-aligned implantation position.

In the configuration shown in FIG. 57, when the jaws 226, 228 are opened to a large extent (as shown in FIG. 58), the post 231 is approximately positioned near an end of the follower section 223 furthest from the pivot point. As the jaws 226, 228 are closed (see FIG. 59), the exterior curve of the follower section 223 slightly contacts the post 231 (with or without a bias therebetween). Because the post-touching surface of the follower section 223 is curved coaxially about the pivot point of the female jaw 228, the post 231 imparts no force onto the flag 216 that would tend to pivot the flag 216 counter-clockwise (with respect to FIGS. 57 to 61). Continued closing of the jaws 226, 228 also does not effect movement of the indicator section 219 at least until the rotation multiplier 225 aligns with the post 231 as shown in FIG. 57. As illustrated in FIGS. 57 and 60, the post 231 can enter the rotation multiplier (notch) 225 without causing any movement of the indicator section 219.

The tang 234 of the female jaw 228 is formed with a dial 227 to allow a user to see clearly any displacement of the flag 216, which displacement indicates that the jaws 226, 228 moved from a non-aligned orientation to an aligned orientation in which the fastener can be implanted safely. Preferably, the flag 216 and the dial 227 have visual contrast, i.e., one is dark and one is light or they have different, easy-to-see and differentiate colors. To effect a clearly visible movement of the indicator section 219 along the dial 227, it is, therefore, desirable to have the flag 216 move along the dial 227 as quickly as possible when the jaw alignment position has been reached. In other words, as the post 231 travels along the post guide surface formed by (1) the follower section 223, (2) the pivot section 221, and (3) the indicator section 219, respectively, it is preferred to have the flag 216 move over a substantial distance on the dial exactly when the jaws 226, 228 move from the non-aligned orientation (see FIGS. 52, 53, 57 to 60) to the aligned orientation (see FIGS. 55, 56, 61). To cause such relative movement, the pivot section 221 incorporates the rotation multiplier 225. In a preferred embodiment, the rotation multiplier 225 is formed by a portion of the post guide surface abruptly increasing in radial distance from the pivot point. In particular, the rotation multiplier 225 can be a notch or, simply, a sharp (and, preferably, curved) increase in radial distance of the post guide surface from the pivot point defining a step 229. Thus, after the post 231 has entered the notch 225 and the jaws 226, 228 move to rotate the flag 216 such that the post 231 is forced against the step 229 on its way towards contacting the end of the indicator section 219 furthest away from the pivot point (from FIG. 58 to FIG. 59 to FIG. 60), the post 231 imparts a force against the flag 216 to pivot the indicator portion 219 counter-clockwise (with respect to FIGS. 57 to 61) over a circumferential distance that is substantially greater than the distance traveled by the post 231 along the post guide surface. In a configuration where the distance is a multiple of ten times greater, after the rotation multiplier 225 acts against the post 231, a slight closing of the jaws 226, 228, i.e., one millimeter of travel by the post 231 along the post guide surface, effects a ten millimeter travel movement of the end of the indicator section 219 furthest away from the pivot point. See FIG. 61. It is noted that the flag 216 need not travel all the way to the end of the dial 227 to indicate the aligned orientation of the jaws 226, 228. Alternatively, a hash mark 233 can be provided at the dial 227 that will line up with a corresponding hash mark 235 disposed at the distal end of the flag 216 as shown, for example, in FIG. 57. Alternatively, or additionally, one area of the dial 227 can have a first indicator (e.g., a first color) and a second area of the dial 227 can have a second indicator (e.g., a second color) and complete travel of the flag 216 into the area of the second indicator can be associated with indicating the aligned orientation of the jaws 226,228. These marking embodiments should only be considered as illustrative.

Figure 64:
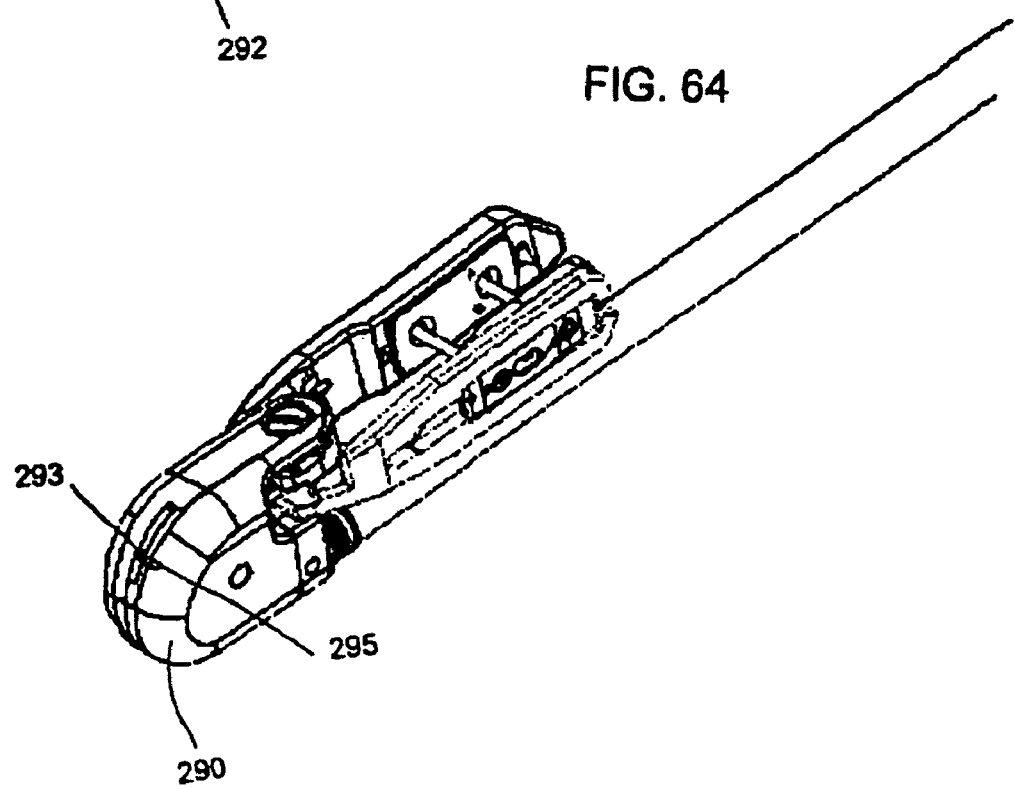
FIG. 64 is a fragmentary, perspective view of the distal end effector of FIG. 63.
Figure 65:
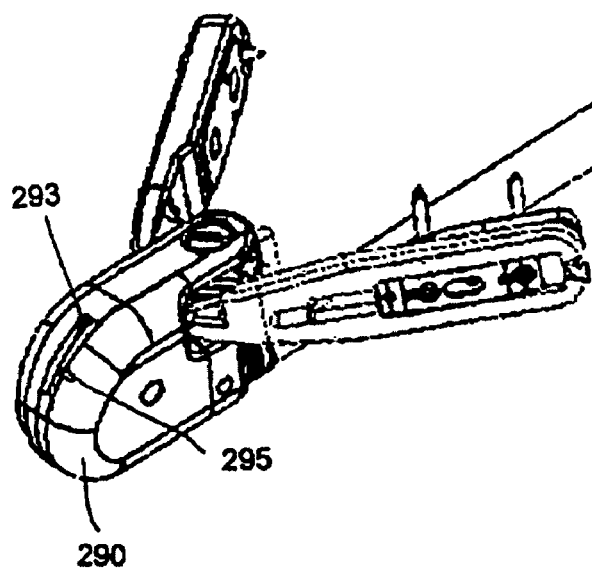
FIG. 65 is a fragmentary, perspective view of the distal end effector of FIG. 63 with the jaws in a substantially open, non-aligned implantation position.

In the third embodiment, most clearly shown in FIG. 63, the bell crank 292 has an extension 293 forming one part of a two-part alignment marker system. As set forth above, the bell crank 292 is fixedly connected to both arms 220, 222 through the V-shaped wire 300 (or two wires/rods). Because the V-shaped wire 300 is, preferably, connected to the arms 220, 222 without any play, each position of the bell crank 292 can be associated with a particular position of the arras 220, 222. Thus, the aligned position of the jaws 226, 228 corresponds to a single unique position of the bell crank 292, which position is illustrated clearly in FIGS. 63 and 64. An appropriate marking 295 of the housing 290, as shown in FIG. 64, forms the second part of the two-part indicator used for signaling when the jaws 226, 228 are aligned and, thereby, indicating that the fastener can be implanted safely. Like the alignment marks 214, 215, the marking 295 can be made by any visually perceptible structure or process.

Figure 66:
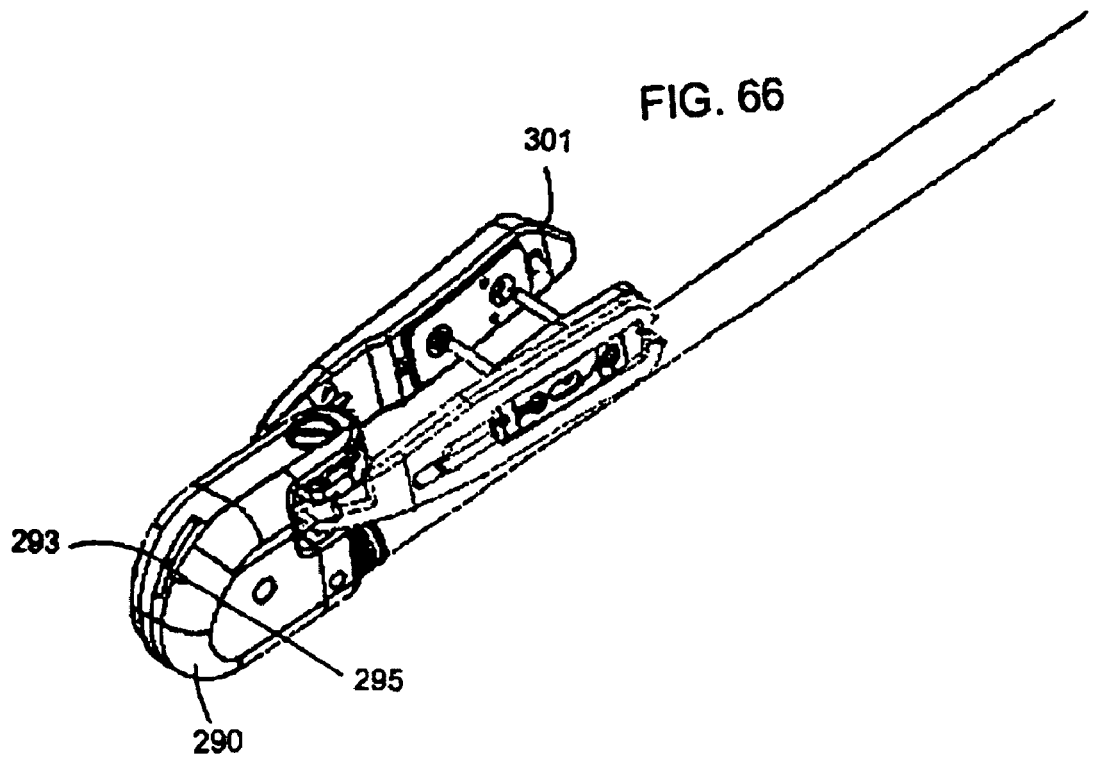
FIG. 66 is a fragmentary, perspective view of the distal end effector of FIG. 63 with the jaws in a partially open, non-aligned implantation position.

FIG. 64 shows the extension 293 in a position where the jaws are in the non-aligned orientation and, therefore, far away from the marking 295. FIG. 66 illustrates the extension 293 moving closer to the marking 295 as the jaws 226, 228 move closer towards one another. Finally, FIG. 63 illustrates the extension 293 and the marking aligned with one another, thereby indicating the implantation position of the end effector 202.

Some of the alignment marking features have been indicated as being connected to one of the male or female jaws 226, 228. Such orientations, however, can be reversed. However, the orientation described provides advantages with respect to applying torque to tissue that are not found in the prior art. Also, all three embodiments of the markers can be combined in any configuration, as shown, for example, in the combination of the second and third embodiments in FIGS. 62 to 66.

Further, a marker system can be incorporated at the proximal actuation handle 204 if there is little play between the marker at the proximal actuation handle 204 and the actual position of the two jaws 226, 228. (See the description below with respect to FIGS. 68 to 78.)

Referring back to FIGS. 27 and 28, the sleeve 320 of the distal end effector 202 preferably has an opening 321 with a diameter of approximately 9 mm, corresponding to the outer diameter of a relatively small endoscope. The exterior dimensions of the sleeve 320 are minimized to provide as low a profile as possible to facilitate passage of the distal end effector 202 out of the patient, in particular, past the Cricopharyngeal Junction. The sleeve 320 may also be provided with a slant nose or other tapered or otherwise streamlined shape that further facilitates introduction and withdrawal of the distal end effector 202 past the Cricopharyngeal Junction. See also FIGS. 93 and 94.

Because the proximal-most end of the end effector 202 presents a surface that will contact the Cricopharyngeal Junction when the end effector 202 is being removed from a patient, if is important, for that surface to smoothly open the Cricopharyngeal Junction and not snag therein. Accordingly, the preferred end effector embodiment shown in FIGS. 52 to 66 tapers at least one surface 301 of the proximal end of the end effector 202. When the fastener 10 is no longer disposed in the end effector 202, and the jaws 226, 228 are allowed to approach one another until they touch (referred to herein as an "overtouch position"), the tapered surface 301, along with the taper of the two jaws 226, 228 in the overtouch position (as shown in FIGS. 38 to 47) forms a frusto-conical shape that naturally opens the Cricopharyngeal Junction on the way out of the esophagus and does not snag therein.

In addition, the sleeve 320 and other portions of the housing 290 are constructed of a preferably soft, low friction, lubricious material such as polytetrafluoroethylene (PTFE), nylon, or silicone to aid in movement over the endoscope and prevent injury to the human body. The sleeve 320 is coupled over or is integral with the housing 290 to enclose the mechanical assembly 292 (FIG. 35). To facilitate the coupling of the sleeve 320 to the end effector 202, it is preferable that the sleeve 320 be provided with two holes 322, 324 and that pivots 296 and 304 (FIG. 35) for the first and second bell cranks 294, 302 be provided with an internal thread (FIG. 35). Screws 326, 328 are inserted in holes 322, 324 and thread into the pivots 296, 304 to lock the sleeve over the housing 290.

Figure 67:
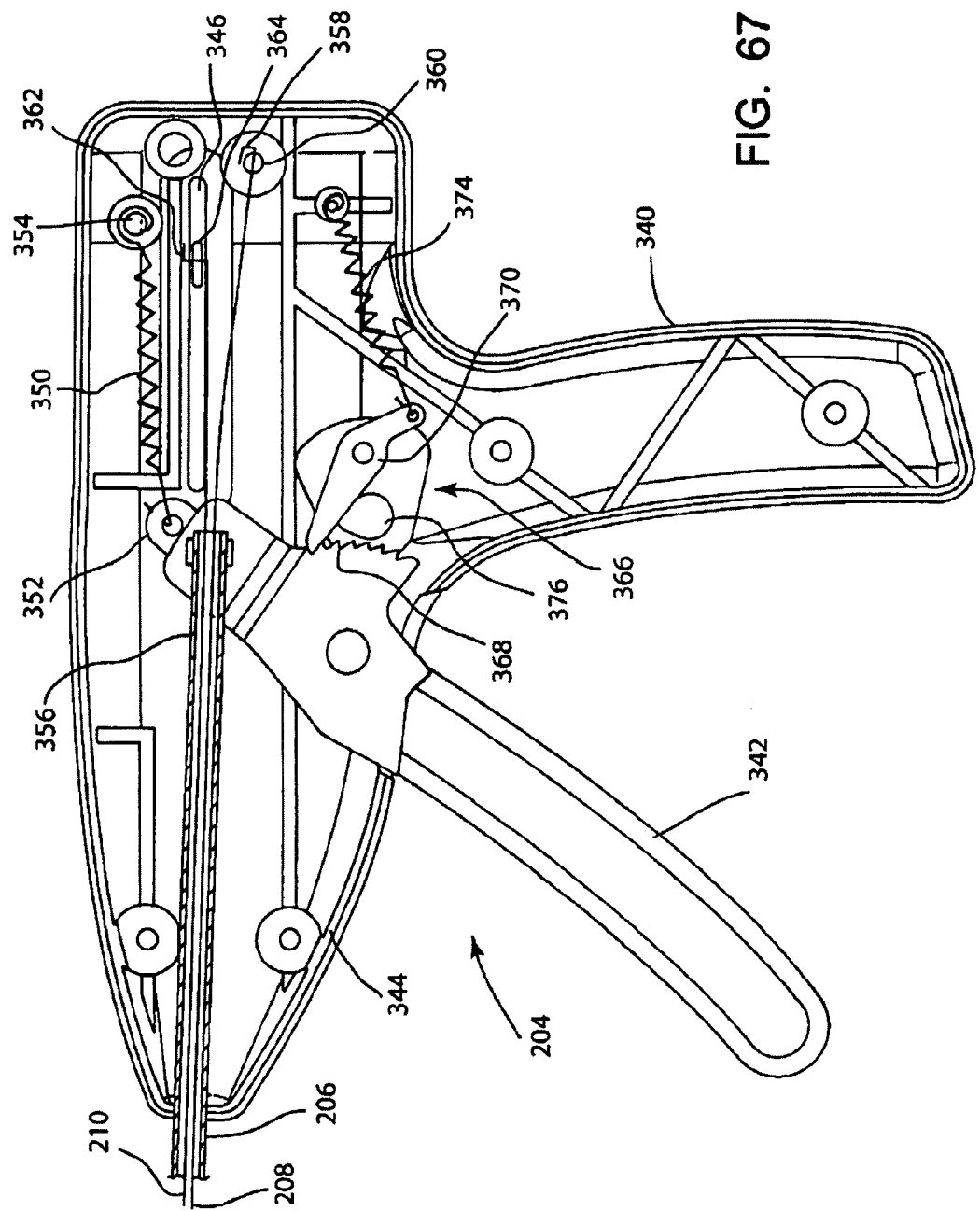
FIG. 67 is a fragmentary side elevational view of the proximal actuation handle of the instrument of FIG. 26 with a side of the handle housing removed for clarity.
Figure 68:
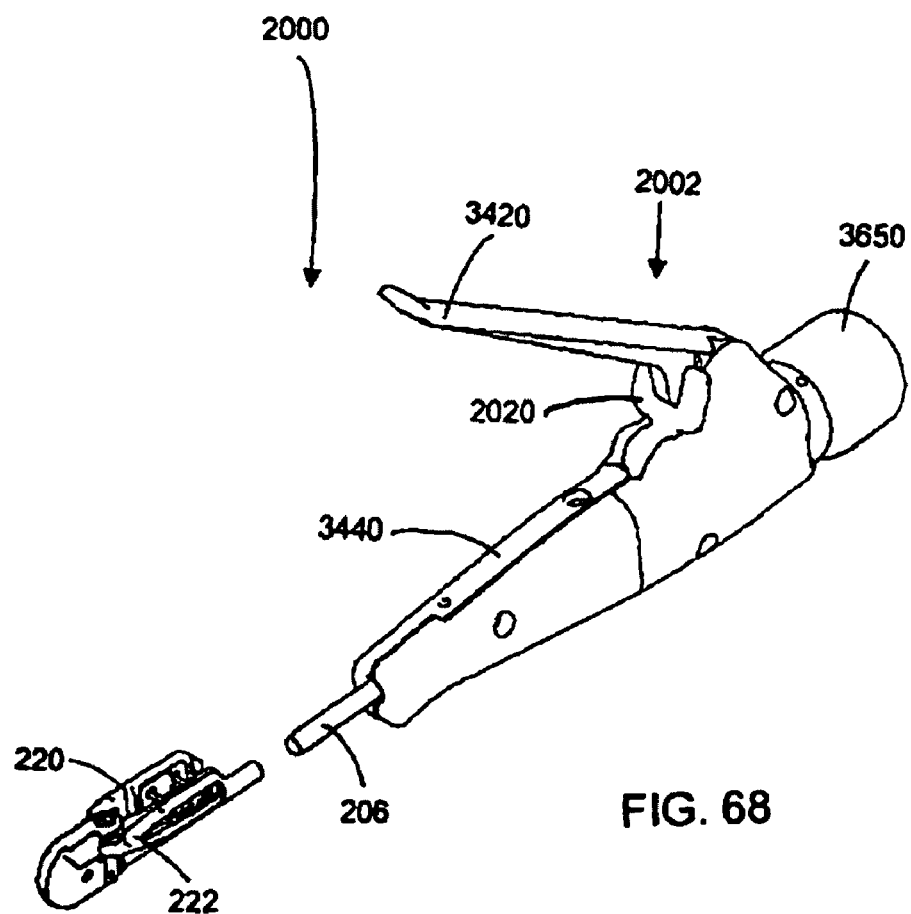
FIG. 68 is a fragmentary, reduced perspective view of a left side of an alternative embodiment of the proximal actuating handle of FIGS. 26 and 67, with an actuating handle in an un-actuated position.

Referring now to FIGS. 26 and 67, a first embodiment of the proximal actuation handle 204 has a pistol-grip style handle including a stationary handle 340 and a lever 342 rotatable relative thereto. The stationary handle 340 is integral with a housing 344, which defines a longitudinal slot 346. A proximal end 356 of the control shaft 206 extends into the housing 344 and is coupled to an upper portion of the lever 342. The first control element 208, which is coupled at its distal end 298 to the jaw arms 220, 222 through the first bell crank 294, includes a proximal control element end 358 that extends out of the proximal end 356 of the control shaft 206 and is fixed at a second mount 360 within the housing 344. The second control element 210, which operates to lock and release the fastener 10 through the second bell crank 302, includes a proximal end 362 that is coupled to a cross bar 364 movable within the longitudinal slot 346. The cross bar 364 includes a handle portion 365 (FIG. 26) disposed outside the housing 344.

Where the second control element 210 is a cable 209' in the two-pulley system of the second embodiment of the jaws 226', 228', the cross bar 364 can be an axle for the third pulley mentioned above and about which the third pulley rotates. In such a configuration, proximal movement of the slide lever 364, 365 and, therefore, the third pulley 3428 (see FIG. 74) equally imparts a proximally directed force to each of the two cable extents of the fastener control element 209' in the control shaft 206.

The lever 342 is biased into an open position with a first spring 350 that is coupled between a lever mount 352 on the lever and a first mount 354 within the housing 344. The lever 342 is also provided with a locking system 366 that operates to lock the position of the lever relative to the handle 340. The locking system 366 includes a plurality of teeth 368 on the lever, a pawl 370 mounted on a pivot 372 and biased with a second spring 374 toward the teeth 368, and a cam 376 that can be manually rotated with an external knob 378 (FIG. 26) to contact the pawl 370 and effect disengagement of the pawl from the teeth 368.

In operation, when the handle lever 342 is rotated toward the stationary handle 340, the control shaft 206 is moved distally relative to the first control element 208 (held stationary by the second mount 360) to effect a closing of the jaws 226, 228. With the jaws in a closed position, the cross bar 364 can be moved distally relative to the stationary handle 340 in order to operate the second bell crank 302 (through control element 210) to cause lock and release of the fastener 10. After a fastener 10 is released, the cam 376 can be operated to release the handle locking system 366 and permit the handle lever 342 to rotate relative to the stationary handle 340, thereby allowing the jaws to reopen.

While a pistol-grip embodiment of the handle 340 has been shown for operation of the instrument 200, as such a handle includes significant mechanical advantage, it may be preferred to use an inline-type handle or other handle configured to also provide the desired mechanical advantage.

Such a preferred handle is described below with respect to FIGS. 68 to 78, which illustrate another embodiment of the instrument 2000 depicted in FIGS. 26 and 67. Like the handle embodiments described above, actuating handle 2002 is used to control two operations: (1) a first operation in which the arms 220, 222 are closed or opened; and (2) a second operation in which the two parts 12, 14 of the fastener 10 are locked together.

The first operation, movement of the arms 220, 222, is controlled by rotation of a proximal knob 3650. Clockwise rotation of the knob 3650 closes the arms 220, 222 and counter-clockwise rotation of the knob 3650 opens the anus 220, 222, or vice-versa if desired.

Depressing an actuating lever 3420 towards a handle body or housing 3440 controls the second operation, locking of the fastener 10. As set forth above, locking of the fastener 10 is only desired when the arms 220, 222 (and, therefore, the jaws 226, 226', 228, 228', 726, 728) are aligned for optimal implantation. Therefore, the second operation should be restricted at least until the arms 220, 222 are approximately aligned in the optimal implantation position (see, e.g., FIG. 56).

To accomplish such restriction, two features are provided at the housing 3440. First, a blocking part 2010 is disposed in the housing 3440 (a two-part clamshell shown in FIGS. 73 and 74). The blocking part 2010 completely prevents depression of the actuating lever 3420 when the blocking part 2010 is disposed in a first blocking position and permits depression of the actuating lever 3420 when the blocking part 2010 is disposed in a second unblocked position. Second, a safety 2020 is operatively connected to the actuating lever 3420 to prevent accidental depression of the actuating lever 3420 when the blocking part 2010 is in the unblocked position. In other words, the user can depress the actuating lever 3420 only after deactivating the safety 2020. As shown in FIGS. 68 to 72, the safety 2020 acts to bar movement of the lever 3420 entirely by being disposed between the lever 3420 and the housing 3440 and being oriented substantially perpendicular to the longitudinal extent of the lever 3420 when the lever 3420 is in its un-actuated position (see, e.g., FIGS. 69 and 70).

Figure 69:
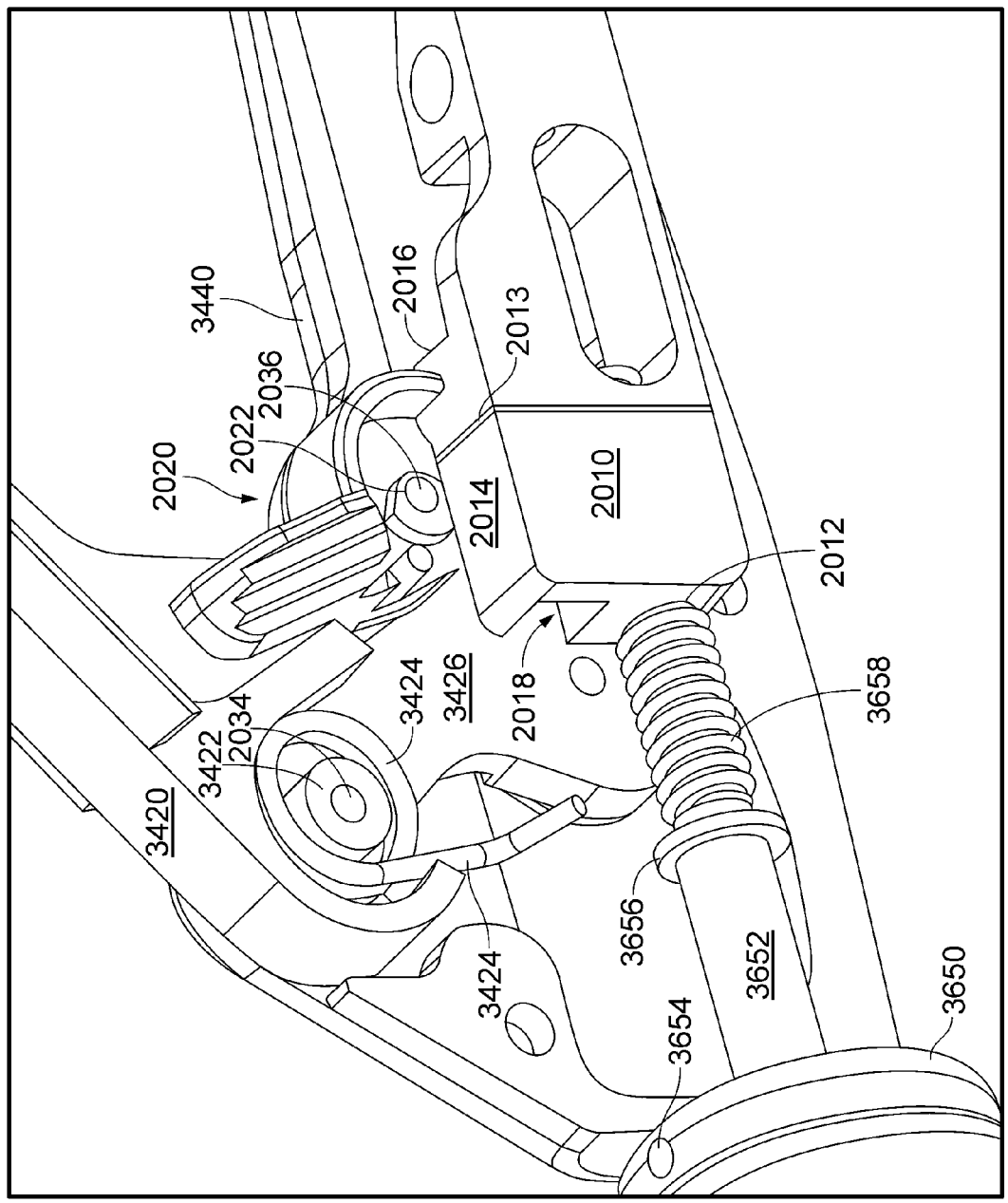
FIG. 69 is a fragmentary enlarged, partially hidden perspective view of a portion of the handle of FIG. 68 from the right side of the handle with a portion of the right side of the housing broken away and with a blocking part in a blocking position, a safety in a safe position, and the handle in the un-actuated position.
Figure 70:
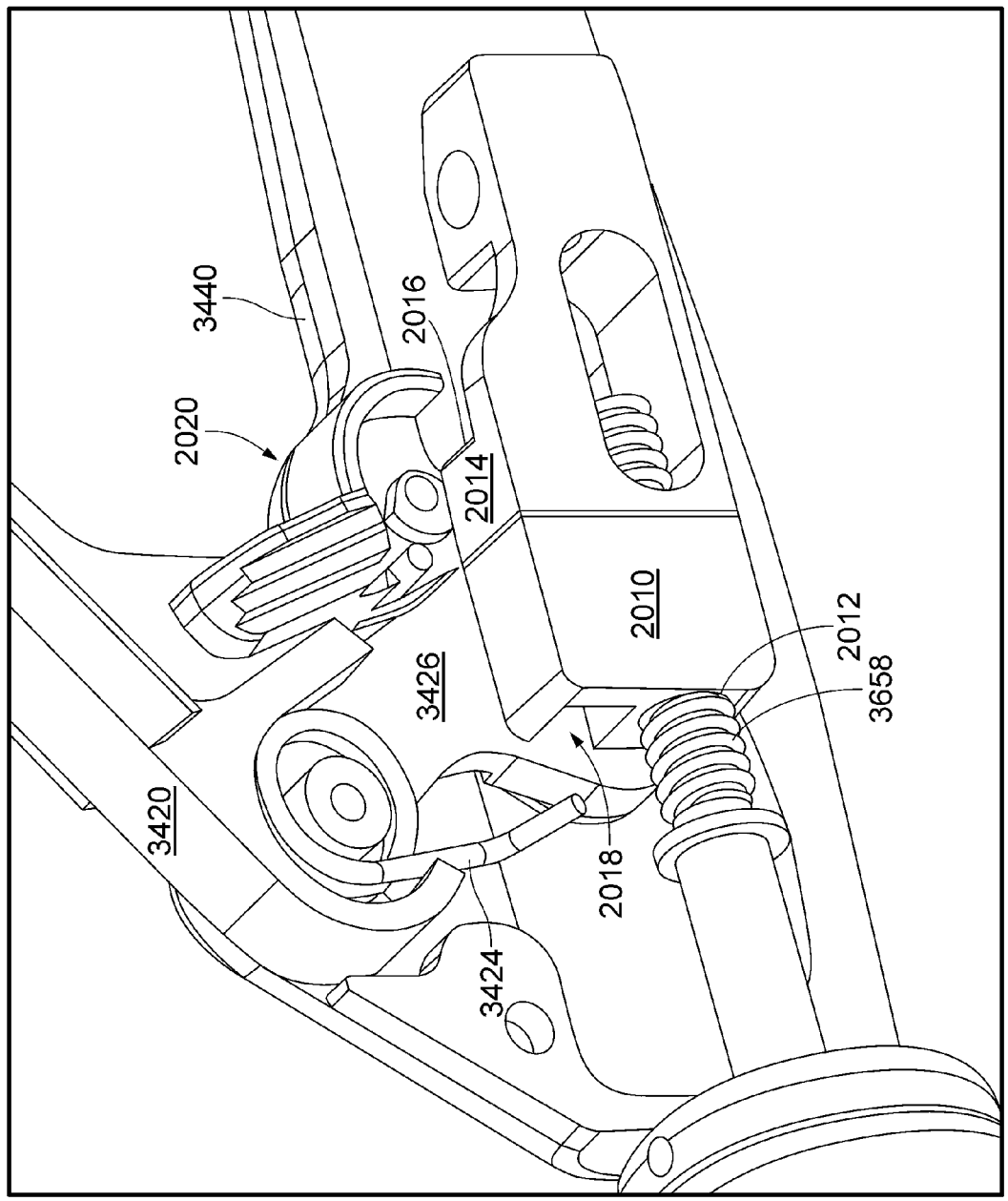
FIG. 70 is a fragmentary enlarged, partially hidden perspective view of the portion of the handle of FIG. 69 with the blocking part in an unblocked position, the safety in the safe position, and the handle in the un-actuated position.
Figure 71:
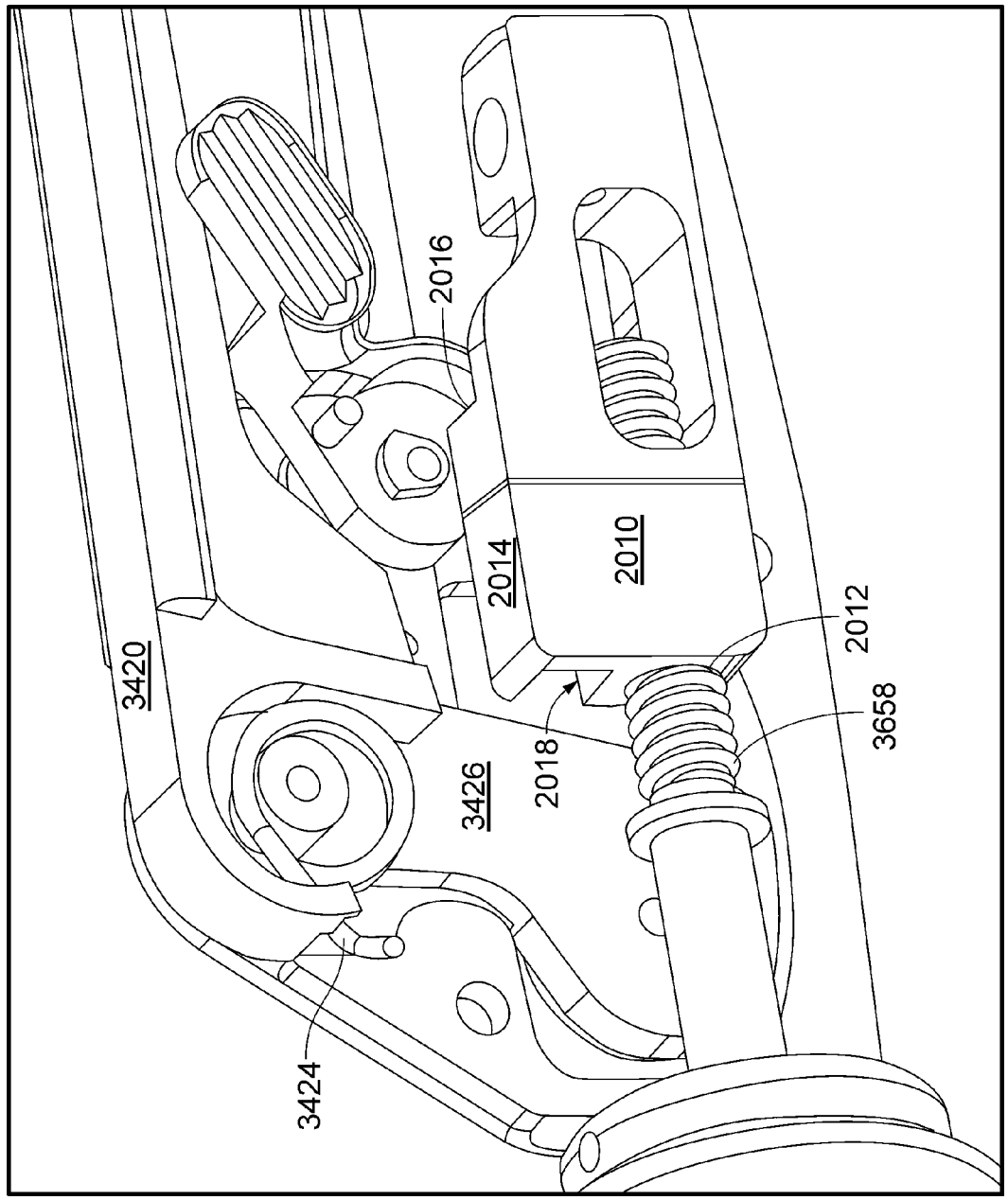
FIG. 71 is a fragmentary enlarged, partially hidden perspective view of the portion of the handle of FIG. 69 with the blocking part in an unblocked position, the safety in an opened position, and the handle in an actuated position.

Operation of the blocking part 2010 and the safety 2020 is illustrated successively in FIGS. 69, 70, and 71, which are enlarged views of the actuating mechanisms inside the housing 3440 with a near side of the housing 3440 (as viewed in the figures) removed.

A portion of the proximal knob 3650 is shown to the left in FIGS. 69 to 71. The knob 3650 is fixedly connected to a shaft 3652 and, therefore, rotational axes of the knob 3650 and the shaft 3652 are substantially aligned with one another. Preferably, a setscrew 3654 (or setscrews) provides the connection between the knob 3650 and the shaft 3652. Alternatively, the knob 3650 and the shaft 3652 are integral. The shaft 3652 is longitudinally fixed in the housing 3440 but remains freely rotatable with respect thereto. In a preferred configuration, the shaft 3652 has a protruding disk 3656 that slidably fits within a corresponding non-illustrated internal groove formed within the housing 3440 and forms a distal stop against a proximal wall of a hollow in the housing 3440 (as shown in FIGS. 75 to 78). The shaft 3652 also has a male threaded proximal end 3659 that is to be screwed into corresponding female threads inside the knob 3650, thereby, axially and rotationally fixing the knob 3650 to the shaft 3652. In such a configuration, the proximal and distal sides of the disk 3656 prevent longitudinal movement of the shaft 3652 and the substantially non-stick connection of the disk 3656 within the housing permits free rotational movement of the shaft 3652. An exterior (male) threaded portion 3658 is provided on a distal end of the shaft 3652.

The blocking part 2010 is disposed in the housing 3440 and the housing 3440 defines a cavity 3442 in which the blocking part 2010 moves. Movement of the blocking part 2010 is defined to completely prevent depression of the actuating lever 3420 when the blocking part 2010 is disposed in the blocking position (see FIG. 69) and to permit depression of the actuating lever 3420 when the blocking part 2010 is disposed in the unblocked position (see FIGS. 70 and 71), as will be explained in further detail below. Preferably, the blocking part 2010 defines a bore 2012 having infernal (female) threads corresponding to the external threads 3658 of the shaft 3652 and the shaft 3652 is, thereby, threaded into the bore 2012. It is noted that if the knob 3650 is rotated sufficiently counter-clockwise, the threads 3658 of the shaft 3652 could leave their connection with the internal threads of the bore 2012, thereby destroying the connection of the knob 3650 to the blocking part 2010. Such an event is entirely eliminated by providing the distal-most end of the shaft 3652 with no threads (see FIGS. 73 and 74) for a distance of at least approximately 2 mm. In other words, the threads 3658 do not extend all the way to the distal end of the shaft 3652 and a smooth portion of the shaft 3652 exists at the distal end thereof. The result of such a configuration allows the threads 3658 to cause distal movement of the blocking part 2010 only until the last thread engages the first thread of the bore 2012. After this point, the smooth distal end, which has a diameter no greater than the innermost internal diameter of the bore 2012, slidably rotates within the bore 2012, axially aligns and keeps the shaft 3652 inside the bore 2012, and does not engage the threads of the bore 2012 until the knob 3650 is rotated clockwise.

The blocking part 2010 has a blocking surface 2014 that is operatively coupled with the actuating lever 3420 when the blocking part 2010 is in the blocking position and is operatively disconnected from the actuating lever 3420 when the blocking part 2010 in the unblocked position. In particular, the blocking surface 2014 is an upper surface 2014 defining a notch 2016. The blocking position places the upper surface 2014 directly in the path of movement of the safety 2020 to entirely prevent movement of the safety 2020 and, thereby, entirely prevent depression of the actuating lever 3420. See FIG. 69. In contrast, the unblocked position places the notch 2016 directly in the path of movement of the safety 2020 (and the upper surface 2014 out of the path of movement of the safety 2020). See FIGS. 70 and 71. In other words, when the upper surface 2014 is moved out of the movement path of the safety 2020, the safety can move unimpeded.

FIG. 69 illustrates the upper surface 2104 in the movement path of the safety 2020. Turning the knob 3650, and, therefore, the threaded portion 3658 of the shaft 3652, causes longitudinal movement of the blocking part 2010. FIG. 70 illustrates the blocking part 2010 after the knob 3650 has been turned through a sufficient extent to move the upper surface 2104 out of the movement path of the safety 2020 and place the notch 2016 in the movement path. The linearity of movement of the blocking part 2010 along the shaft threads 3658 depends upon the thread spacing. In FIGS. 69 to 71, the threads 3658 are shown to have equal spacing. Therefore, the blocking part 2010 will move linearly with respect to rotation of the knob 3650. Alternatively, the threads 3658 can have a non-illustrated variable assembly that, for example, allows the arms 220, 222 to close quickly with initial turning of the threads and close ever more slowly as the blocking part 2014 approaches the disk 3656.

The housing 3440 defines a bore in which is inserted a pivot rod 2034 that, when inserted in the bore, projects from an interior wall of the housing 3440. The actuating lever 3420 is rotatably secured to the housing 3440 by sliding a hollow pivot 3422 of the lever 3420 over and about the rod 2034. The external shape of the rod 2034 corresponds to the internal shape of the pivot 3422 to permit rotation of the actuating lever 3420 about the rod 2034. The housing 3440 defines a second bore in which is inserted a second pivot rod 2036 that, when inserted in the second bore, projects from an interior wall of the housing 3440. The safety 2020 is rotatably secured to the housing 3440 by sliding a hollow pivot 2022 of the safety 2020 over and about the second rod 2036. The external shape of the second rod 2036 corresponds to the internal shape of the pivot 2022 to permit rotation of the safety 2020 about the rod 2036. These rods 2034, 2036 can take any form that allows both the actuating lever 3420 and the safety 2020 to rotate freely through a specified are with respect to the housing 3440. Preferably, the actuating lever 3420 is biased in its open position with a bias device 3424, in particular, in the form of a torsional or mousetrap spring shown in FIGS. 69 to 71. To depress the actuating lever 3420, the user must overcome the force of the spring 3424.

As shown in FIG. 71, the safety 2020 can be pivoted away from the actuating lever 3420 (in a clockwise direction with respect to the view of FIG. 71) to permit a rotation of the actuating lever 3420 about its pivot 3422 (in a clockwise direction with respect to the view of FIG. 71) and, thereby, effect an actuation of the release elements 259, 272 (see FIGS. 27 and 33) or elements 259' and 272' (see FIGS. 40 to 42, 45, and 46) to lock together the male and female parts 12, 14 of the fastener 10 and release the fastener 10 from the jaws 226, 226', 228, 228'.

As shown in FIGS. 35 to 37, the first and second control elements 208, 210 (preferably, wires, cables or flexible rods) extend between the handle and the end effector and are housed in the tubular control shaft 206. In the actuation handle embodiment of FIGS. 68 to 78, in comparison, to effect clamping and opening of the jaw assembly 218 (see FIG. 27), the knob 3650 is operatively connected to a proximal end of the control element 208, which, in turn, has a distal end 298 coupled to the input side of the first bell crank 294.

Figure 72:
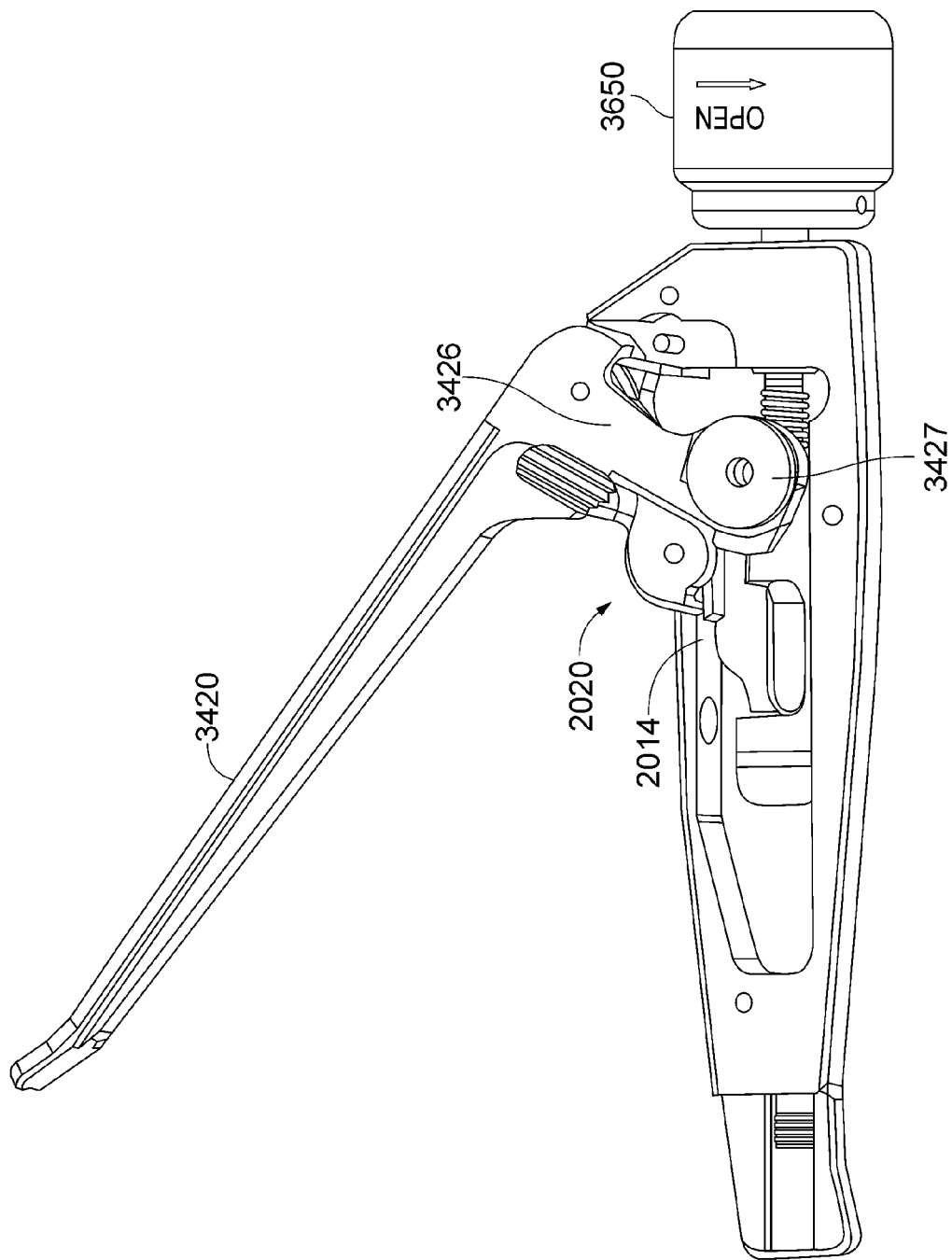
FIG. 72 is a fragmentary enlarged, partially hidden perspective view of the actuating handle of FIG. 68 from the left side of the handle with a portion of the left side of the housing broken away and with the blocking part in the blocking position, the safety in the safe position, and the handle in the un-actuated position.
Figure 74:
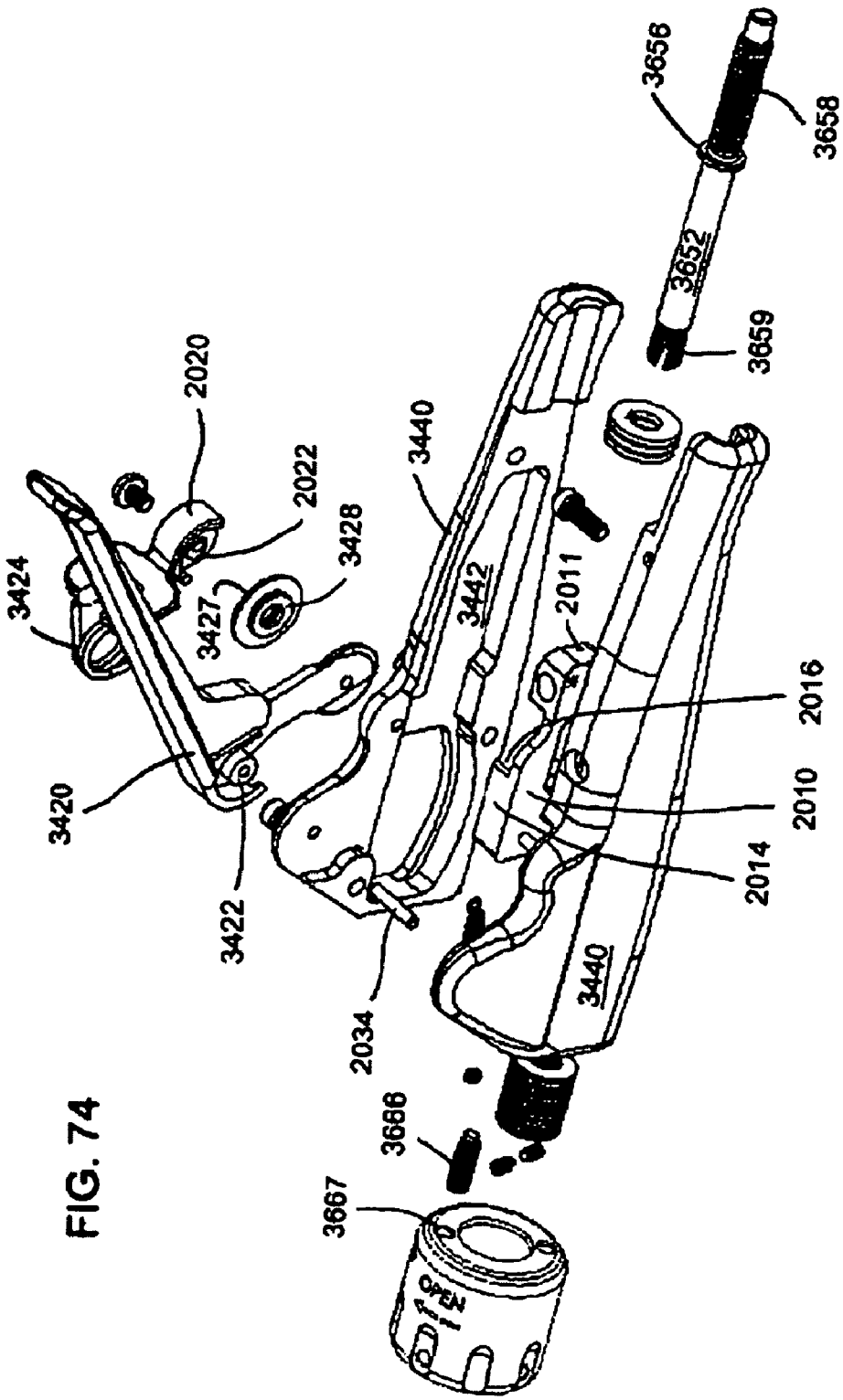
FIG. 74 is an exploded perspective view of the actuating handle of FIG. 68 from above the right side thereof.
Figure 75:
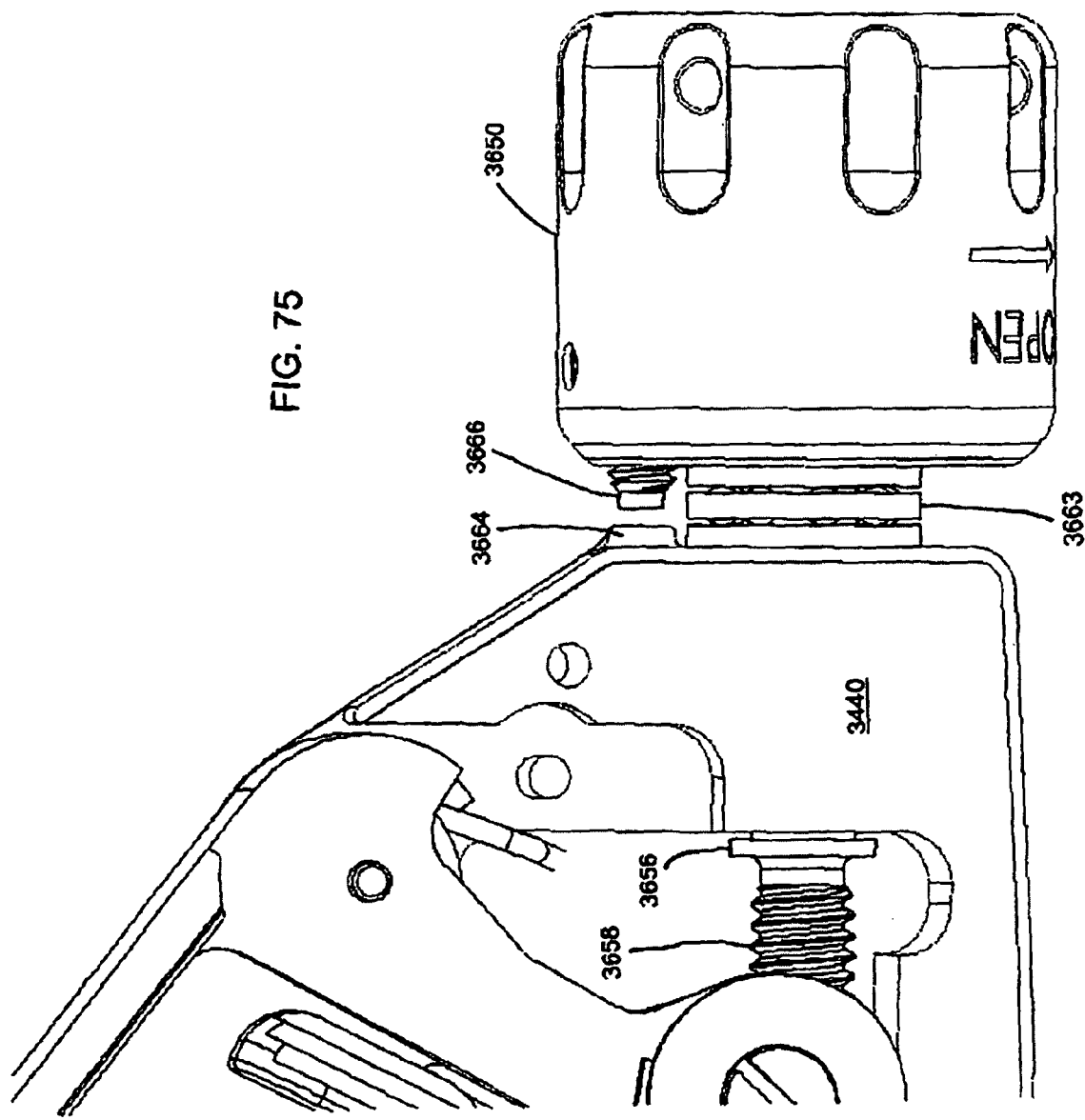
FIG. 75 is a fragmentary, enlarged, elevational view of a force-limiting knob of the actuating handle of FIG. 68 from the left side thereof with the left side of the housing removed for clarity and with the knob in a rotatable position.
Figure 76:
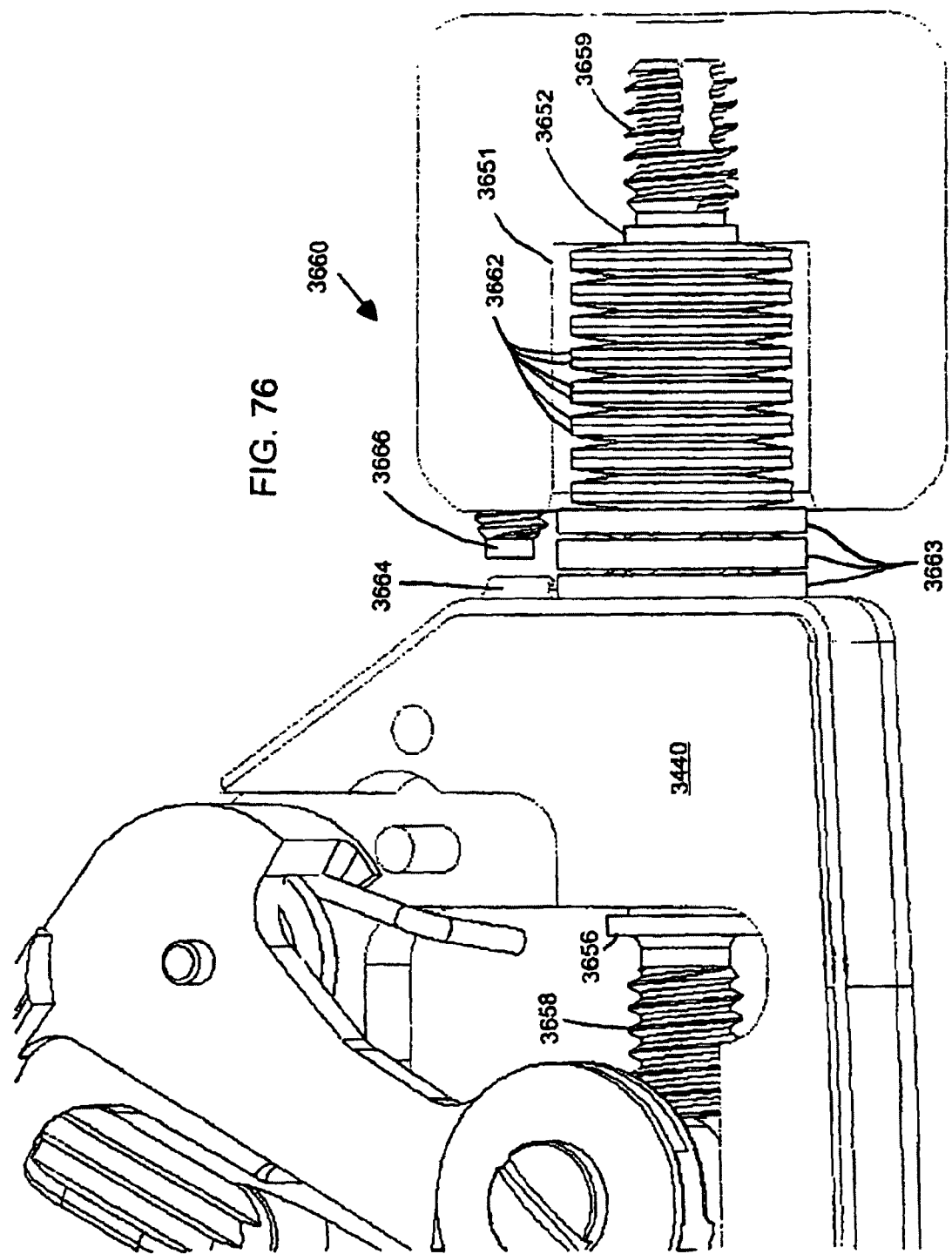
FIG. 76 is a fragmentary, enlarged, perspective view from below the actuating handle of FIG. 68 from the left side thereof with the left side of the housing removed for clarity and a cross-sectional view of the knob of FIG. 75.
Figure 77:
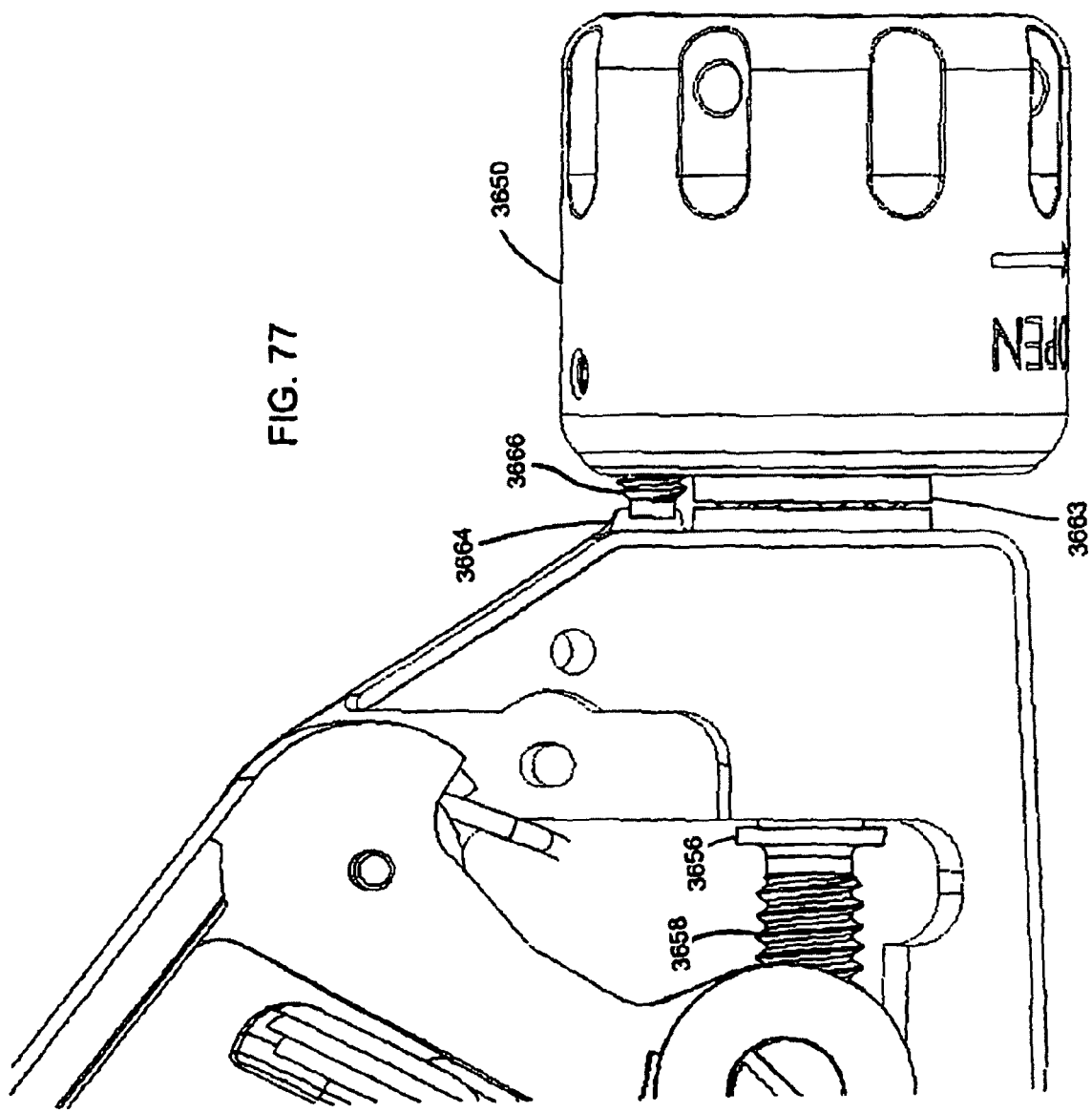
FIG. 77 is a fragmentary, enlarged, elevational view of a force-limiting knob of the actuating handle of FIG. 68 from the left side thereof with the left side of the housing removed for clarity and with the knob in a uni-directional rotating position.

To connect the knob 3650 to the control element 208, a proximal end of the control element 208 is fastened securely to the blocking part 2010, preferably, at a connection point 2011 on a distal end of the blocking part 2010 (see FIGS. 72 and 74). A preferred embodiment provides the distal face of the blocking part 2010 with a first bore having a shape substantially corresponding to the outer shape of the control element 208. To fasten the control element 208 in the first bore, a setscrew is disposed in a threaded second bore disposed orthogonal to the first bore on the near side of the blocking part 2010 as viewed in FIG. 69. Because the control element 208 and the control shaft 206 are substantially stiff and allow little play of the element 208 within the shaft 206, longitudinal movement of the blocking part 2010 directly translates into longitudinal movement of the control element 208. Accordingly, a rotation of the knob in a given direction causes the blocking part 2010 to move longitudinally, which causes the control element 208 to move longitudinally, which opens or closes the jaw assembly 218. If there is little or no play in this control system, a given rotation of the knob 3650 will directly correspond to a given movement of the jaw assembly 218.

For the handles of FIGS. 26 and 67, to lock and release the fastener 10, the actuating slide 364, 365 is operatively connected to a proximal end of the control element 210, which, in turn, has a distal end 306 attached to the input side of the second bell crank 302. In the actuation handle embodiment of FIGS. 68 to 78, in comparison, to effect a locking and release of the fastener 10, the lever 3420 is operatively connected to a proximal end of the looped cable 209', which, in turn, has a two distal ends each respectively coupled to the male and female locking and release devices, in particular, the post release slide 259' and stirrup 272'.

To effect the connection between the lever 3420 and the looped cable 209', the lever 3420 has an integral load arm 3426. The load arm 3426 is configured to transfer a depressing movement of the lever 3420 into a proximally directed force in a direction somewhat or substantially aligned with the shaft 206. Therefore, when the load arm 3426 is connected to the proximal end of the control cable 209', depression of the lever 3420 moves the cable 209' in a proximal direction.

Figure 73:
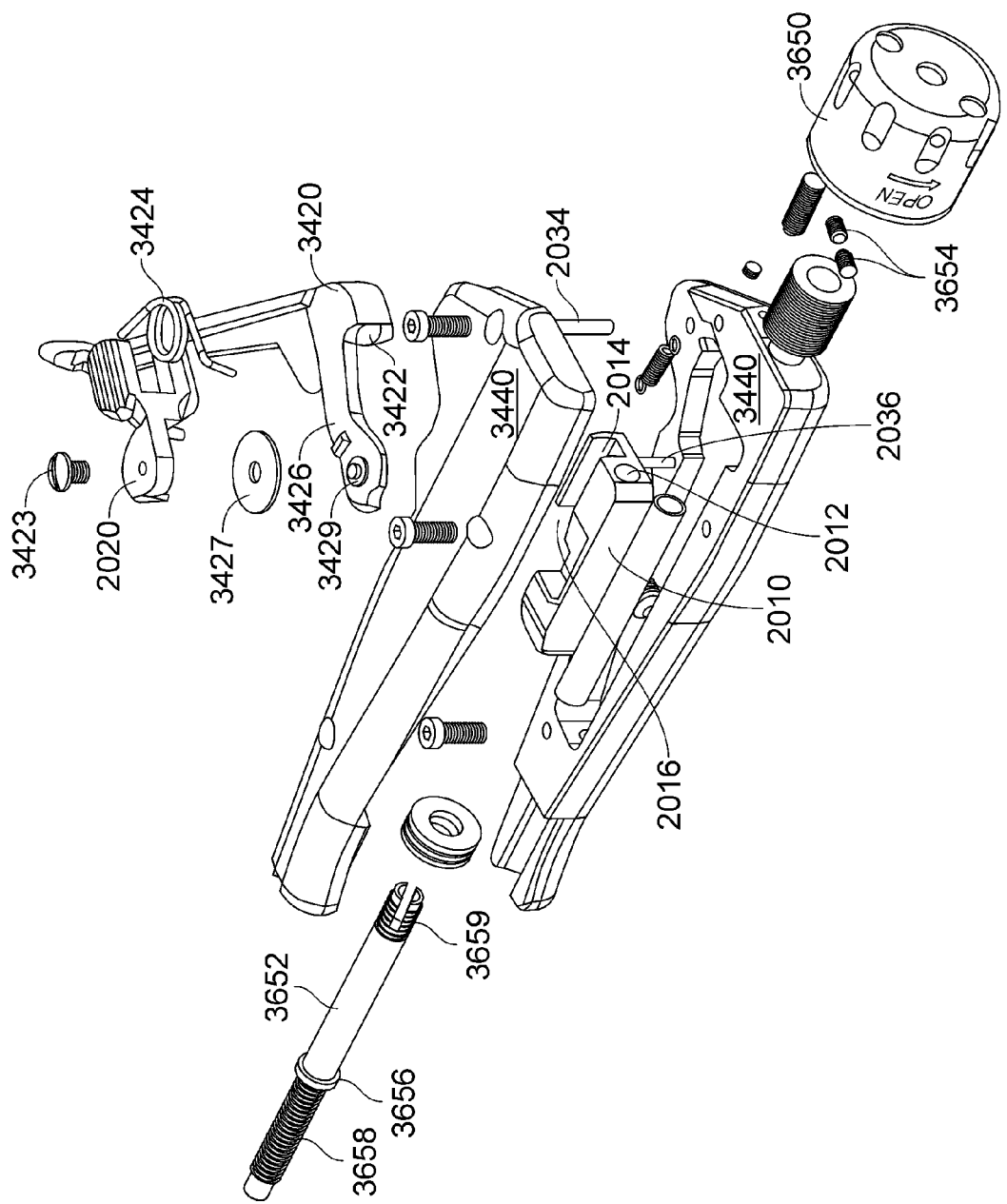
FIG. 73 is an exploded perspective view of the actuating handle of FIG. 68 from below the left side thereof.

The load arm 3426 has an assembly operatively connected to the control cable 209'. As set forth above, the cable is in the form of a loop at the proximal end inside the handle 2002. Therefore, a loop control device is disposed at the load arm 3426, a preferred configuration of which is illustrated in FIGS. 72 to 74. Specifically, the third pulley 3428 mentioned above is disposed rotatably between a washer 3427 and the load arm 3426. (The third pulley 3428 need not be rotatable if the cable can slide thereon with insignificant friction.) The washer 3427 has a diameter sufficiently greater than a diameter of the third pulley 3428 so that any amount of play in the loop of the control cable 209' (which, preferably, is minimal) does not allow the loop to disengage from the third pulley 3428. In a preferred configuration, the washer 3427 defines a central bore and is slidably disposed over an outer circumference of an internally threaded boss 3429 projecting from the load arm 3426. A male threaded bolt 3423 is inserted through a bore of the washer 3427 and a bore of the third pulley 3428 and screwed into the interior female threads of the boss 3429. In such a configuration, when the lever arm of the lever 3420 is depressed from the orientation shown in FIGS. 68, 69, 70, and 72 to the orientation shown in FIG. 71, the load arm 3426, along with the third pulley 3428, moves in a proximal direction, thereby pulling both extents of the cable 209' in the control shaft 206 proximally and actuating both the unlocking and releasing features 259', 272' in each of the male and female jaws 226', 228'.

It is desirable for the blocking part 2010 to be fixed in all respects except for longitudinal movement along the extent of the threads 3658 (in the direction of the rotational axis of the shaft 3652). To fix the blocking part 2010 in all directions orthogonal to the longitudinal axis of the shaft, the blocking part 2010 defines a groove 2018. See FIGS. 69 to 71. The housing 3440 can be provided with a non-illustrated block having a shape corresponding to the shape of the groove 2018. The block, therefore, acts as a guide to only permit the blocking part 2010 to move in the desired direction of the rotational axis of the shaft 3652. Preferably, the block has a sufficient length to prevent any rotation of the blocking part 2010 in a direction orthogonal to the rotational axis of the shaft 3652 (i.e., in a direction parallel to the pivot axes of the lever 3420 and the safety 2020). Preferably, the cavity 3442 in the housing 3440 is shaped to act as a guide to only allow the blocking part 2010 to move in the desired direction. Such a shape can be seen, in particular, in FIG. 74.

FIG. 72 shows an alternative view of the handle of FIGS. 68 to 71 and is a view of the opposite, left side of handle of FIGS. 69 to 71 with a portion of the left side of the housing broken away and clearly showing the washer 3427 loop control device. As can be seen in FIG. 72, the blocking surface 2014 of the blocking part 2010 is in the blocking position, the safety 2020 is in the safe position, and the handle 3420 is in the un-actuated position.

It is desirable to have markers indicating to a user that the jaws are in the proper aligned position substantially parallel to one another for fastener implantation. See. e.g., FIGS. 52 to 55. The markers described above, however, are all present at the distal end of the instrument 200; in other words, when the user desires to view the relative positions of the aforementioned indicators, they are all located within the patient's body—a location that may not be optimal for user viewing. It would, therefore, be desirable to have visual indicators at the handle 2002, which indicators would provide the user with substantially the same information as the markers present at the distal end of the instrument 200. However, there is a problem associated with relying solely on markers at the proximal end of the instrument 200. If there is any play in a jaw assembly control system, then circumstances could occur where the user sees proper alignment of these proximal markers but that jaw assembly actually is not in the optimal position for locking the fastener. Such a condition is undesirable and should be prevented.

As set forth above, the connection between the knob 3650 and the control element 208 is one that has substantially no play. Therefore, the configuration of the jaw assembly control system (3650, 3652, 3658, 2010, 208, 292, 300) of the present invention substantially eliminates any possibility of the jaw assembly 218 being improperly aligned when the proximal handle markers are aligned. FIGS. 69 to 71 indicate one possible embodiment of a set of alignment markers for the actuating handle 2002. First, the blocking part 2010 is provided with one marker 2013 of a pair of markers. The marker 2013 can be only on the upper surface 2014, only on another surface, on a combination of surfaces, or can entirely encircle the blocking part 2010 as shown in FIGS. 69 to 71. A non-illustrated opening is provided in the housing 3440, allowing the user to view clearly the marker 2013 inside on the blocking part 2010. The opening can be merely a hole or, to allow fluid-tight integrity of the interior space of the housing 3440 for purposes of sterilization, can be a clear viewing window. To complete the marker pair, the opening can have co-axial indicator lines on the exterior of the housing that line up with the marker 2013 when the knob 3650 has been rotated to place the jaw assembly 218 in the implantation position. In comparison, the clear viewing window can have the second marker of the pair extend entirely across the window and, like the indicator lines mentioned above, line up with the marker 2013 disposed thereunder when the knob 3650 has been rotated to place the jaw assembly 218 in the implantation position.

Alternatively, or additionally, alignment marks can be placed on the knob 3650 and on a proximal-most surface of the housing 3440 near the knob 3650. Alignment of these marks would indicate that the jaw assembly 218 is in the optimal position for locking the fastener. Such an embodiment, however, must clearly prevent the knob 3650 from rotating more than 360 degrees because the alignment marks align in every 360° rotation of the knob 3650.

The preferred embodiment of the knob 3650 is shown in FIGS. 73 to 78. As indicated above, the jaw control element 208 is, preferably, a rod having a fixed length and is attached to the first bell crank 294 at the distal end thereof and to the blocking part 2010 at the proximal end thereof. Because the rod 208 is not elastic along its longitudinal extent, and because the blocking part 2010 pulls the rod proximally to close the jaws 226, 226', 228, 228' of the end effector 202, there exists the possibility of applying too much force upon the assembly at the end of the rod 208 and/or applying too much force on the tissue disposed between the male 12 and female 14 fastener parts and/or closing the jaws 226, 226', 228, 228' too much. In other words, as the blocking part 2010 is moved proximally, thereby, pulling the rod 208 and placing it in tension, a tuned compensation device could substantially or entirely prevent the application of too much force to the rod 208 from a further turning of the knob 3650.

To provide this advantageous feature, the actuating handle 2002 has a tuned compensation assembly 3660. A substantial portion of the compensation assembly 3660 is disposed within a central main cavity 3651 of the knob 3650. The compensation assembly 3660 includes a bias device 3662, 3663—disposed between the knob 3650 and the housing 3440 in the main cavity 3651—and a knob-limiting assembly 3664, 3666—disposed between the knob 3650 and the housing 3440.

Figure 78:
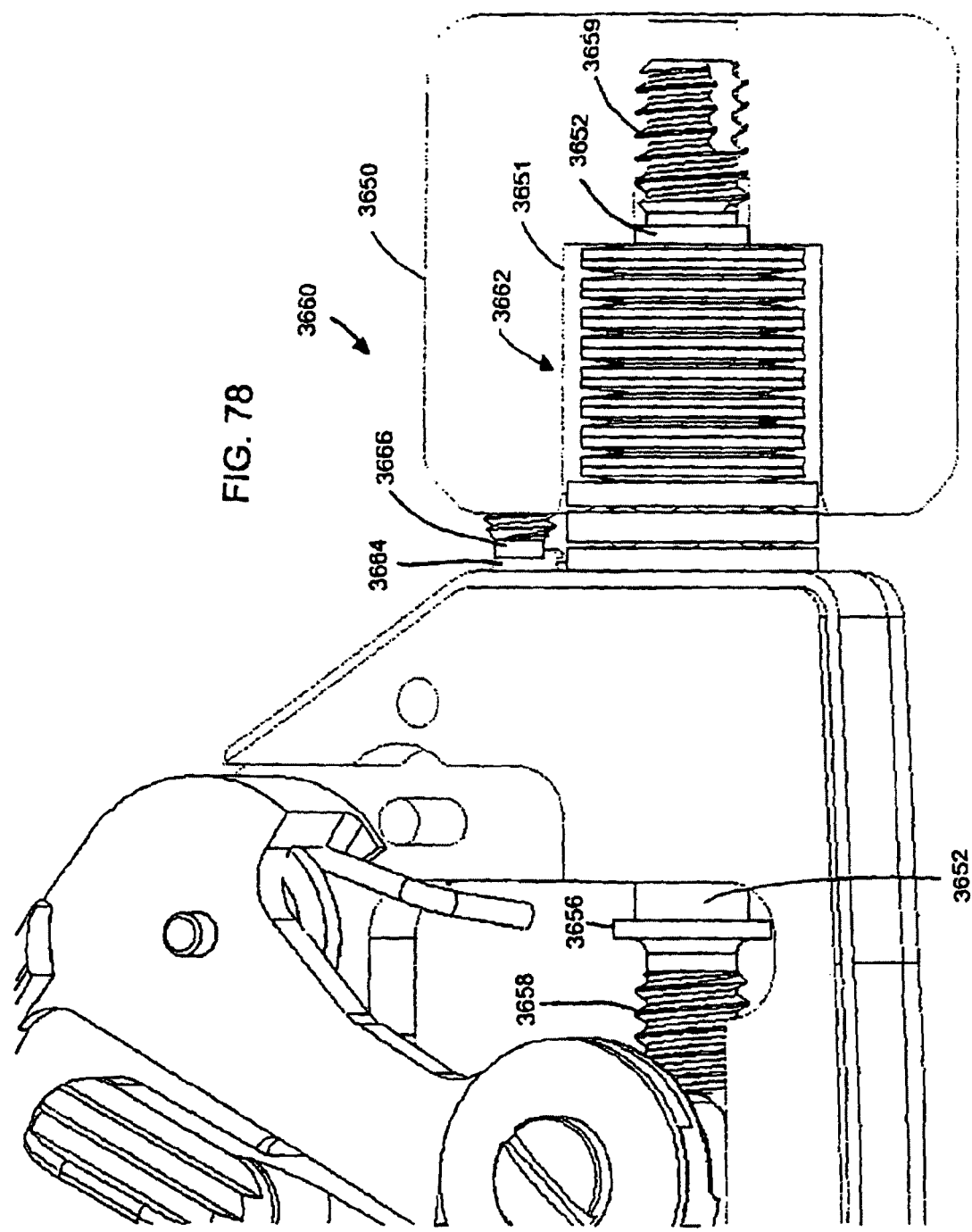
FIG. 78 is a fragmentary, enlarged, perspective view from below the actuating handle of FIG. 68 from the left side thereof with the left side of the housing removed for clarity and a cross-sectional view of the knob of FIG. 77.

In a preferred embodiment shown in FIGS. 73 to 78, the bias device includes a disk spring or a set of disk springs 3662 and a ball thrust bearing assembly 3663. Both the spring(s) 3662 and thrust bearing 3663 have non-illustrated hollow center areas configured to fit therein the smooth portion of the shaft 3652. Therefore, the spring(s) 3662 and thrust bearing 3663 are disposed between the knob 3650 and the proximal-most outer surface of the housing 3440 and are mechanically coupled with both the knob 3650 and the housing 3440 but are decoupled from the outer smooth surface of the shaft 3652. Thus, as a distally directed force is imparted upon the distal end of the shaft 3652 (caused by tension of the rod 308 pulling the blocking part 2010 distally), the knob 3650 is also forced distally. Until the bias of the disk spring(s) 3662 is overcome by the distally directed force, the knob 3650 does not move in a distal direction. See FIG. 76. However, when the force is greater than the bias of the spring(s) 3662, the spring(s) 3662 compresses and the knob 3650 moves distally as shown in FIG. 78.

The preferred knob-limiting assembly includes a protrusion 3664 disposed at the proximal-most outer surface of the housing 3440 and an adjustable rotation stop 3666 connected to the distal-most surface of the knob 3650. So long as the spring(s) 3662 is not compressed, the knob 3650 is free to rotate such that the stop 3666 does not contact the protrusion 3664, thereby preventing further rotation of the knob 3650 (preferably, in a clockwise direction for jaw 226, 226', 228, 228' closure). To adjust a distance between a distal-most surface of the stop 3666 with respect to a distal-most surface of the knob 3650, a female threaded bore 3667 (shown in FIG. 74) is defined in the distal-most surface of the knob 3650 and the stop 3666 is formed with a male thread corresponding to the threaded bore 3667 in the knob 3650. If the bore 3667 has a depth greater than a longitudinal length of the stop 3666, then the stop 3666 can be easily adjusted (by providing a distal end of the stop 3666 with an outer shape of a nut or with a groove for receiving a tool, e.g., a screwdriver) between a fully inserted position and a fully extended position. It is to be understood that the protrusion 3664 and the stop 3666 can be reversed in position on the housing 3440 and the knob 3650 and that other rotational stopping mechanisms can be used as well.

The spring(s) 3662 and the thread frequency of the distal threads 3658 of the shaft 3652 are tuned so that a single rotation of the knob 3650 brings the stop 366 from a completely non-contacting position with respect to the protrusion to a substantially contacting position with the protrusion, the contact being sufficient to prevent further rotation of the knob 3650 (preferably, further clockwise rotation thereof). The non-contacting and contacting positions of the stop 366 and protrusion 3664 are shown in a comparison of FIGS. 75 and 77 (and FIGS. 76 and 78). A preferred thread frequency of the distal threads 3658 is between 20 and 30 per inch, in particular, 24 per inch. The preferred distance for the single rotation switch of non-contact to contact is between 0.015" and 0.030" and greater than 0.005', in particular, approximately 0.020'. A preferred k-factor of an assembly of disc springs 3662 is 500 pounds per inch.

Figure 79:
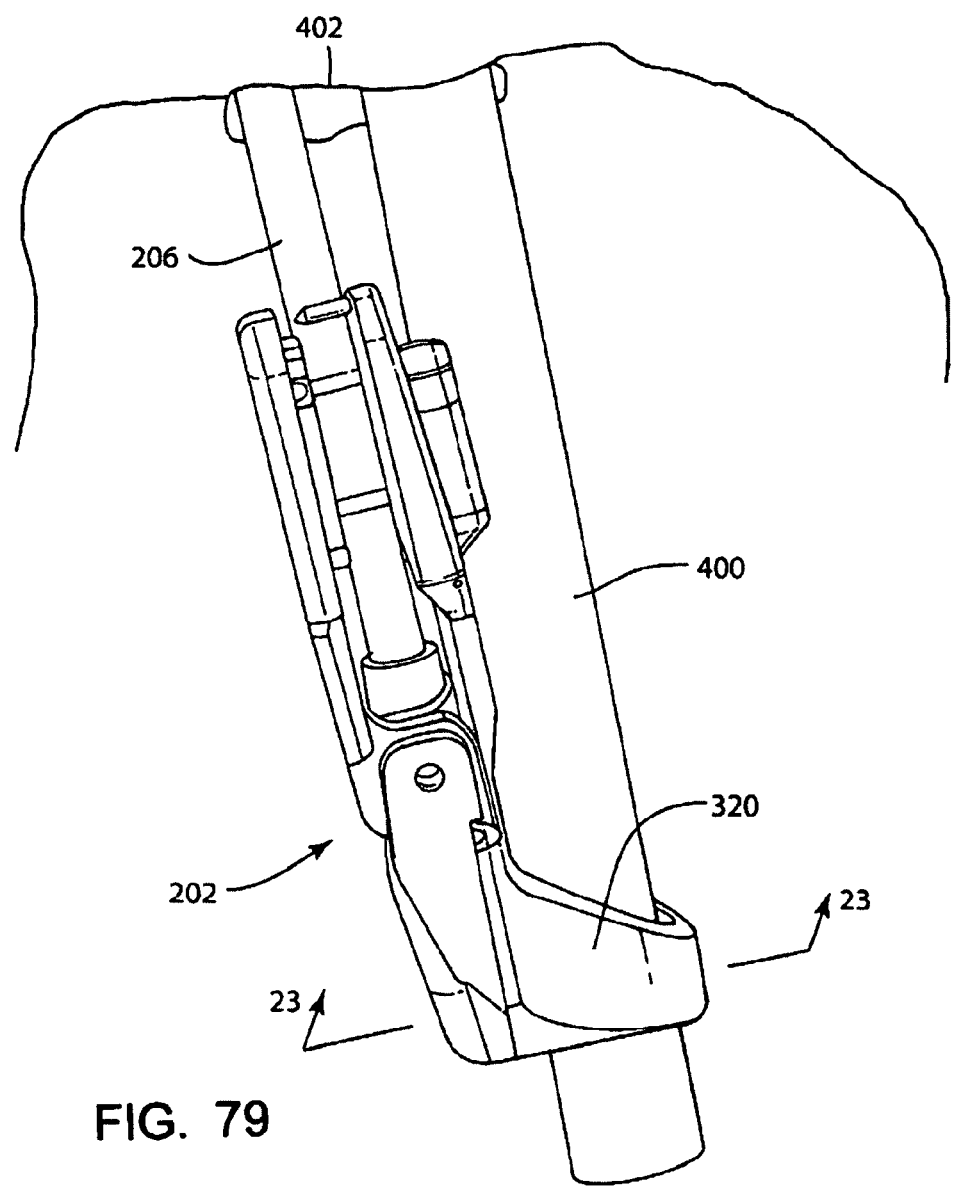
FIG. 79 is a fragmentary, side view of the instrument according to the invention coupled to an endoscope during insertion thereof into the stomach.

According to one embodiment of the method of the invention, the instrument 200 may be operated as follows with respect to the treatment of GERD. Turning to FIG. 79, the sleeve 320 of the distal end effector 202 is slidably coupled over the distal end of an endoscope 400 and the end effector is slid proximally over the endoscope. The distal end of the endoscope 400 is, then, inserted past the Cricopharyngeal Junction and moved through the esophagus and into the stomach until the end effector 202 of the instrument 200 reaches a distance from the distal end of the endoscope 400, preferably, by approximately 20 cm. The handle 204 and/or control shaft 206 are, then, manipulated in gross to slide the distal end effector 202 over the distal end of the inserted endoscope 400 and into the stomach, with the endoscope 400 functioning as a guidewire for the sleeve 320. Optionally, the endoscope 400 may be retroflexed to look back toward to the LES 402 of the esophagus and visualize the advancement of the end effector 202.

Figure 80:
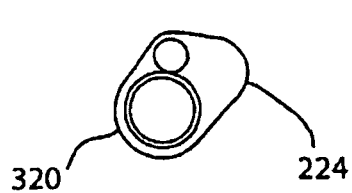
FIG. 80 is an end view schematic illustration of a cross-sectional area across section line 80-80 in FIG. 26 at a portion of the distal end effector of the instrument.
Figure 81:
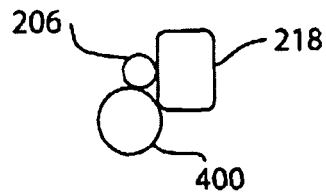
FIG. 81 is an end view schematic illustration of a cross-sectional area across section line 81-81 in FIG. 26 at a portion of the distal end effector of the instrument with an endoscope.
Figure 82:
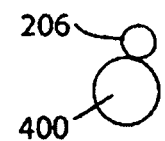
FIG. 82 is a schematic illustration of the cross-sectional area of the endoscope and the control shaft.

Referring to FIG. 80, it is particularly noted that during insertion of the end effector 202 over the endoscope 400 and into the patient (and later withdrawal of the end effector 202 from the patient), the maximum cross-sectional area of the system extending within the esophagus occurs with the combined area of the sleeve 320 and the portion of the clevis 224 that extends outside the footprint of the sleeve; i.e., approximately 188 mm$^2$—smaller than any of the existing or proposed devices in the prior art. The second largest cross-sectional area of the system within the esophagus is at the location of the jaws 226, 228 with the jaws loaded with a fastener 10. Referring to FIG. 81, this area includes the footprint of the jaw assembly 218 loaded with a fastener, as well as the control shaft 206 and the endoscope 400, and is approximately 178 mm$^2$. The portions of the system having the cross-sectional areas of FIGS. 80 and 81 are located within the esophagus only during insertion and removal of the end effector 202 into the patient. Referring to FIG. 82, at all other times and along all other portions of the present system proximal the distal end effector 202, the cross-sectional area of the system in the esophagus is substantially smaller, limited to the combined cross-sectional areas of the endoscope 400 (approximately 63.6 mm$^2$ for a 9 mm scope) and the control shaft 206 (approximately 12.6 mm$^2$ for a 4 mm control shaft); i.e., a total cross-sectional area of approximately 76.2 mm$^2$ or less.

Figure 83:
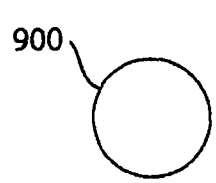
FIG. 83 is a schematic illustration of the cross-sectional area of a prior art device.

In contrast, the prior art diagrammatically illustrated in FIG. 83 shows the relative size of a cross-sectional area corresponding to a prior art device 900 having a diameter of 18 mm (254 mm$^2$), such as the NDO Surgical, Inc. device described above in the State of the Art section. This relatively larger area obstructs the esophagus throughout the procedure.

Figure 84:
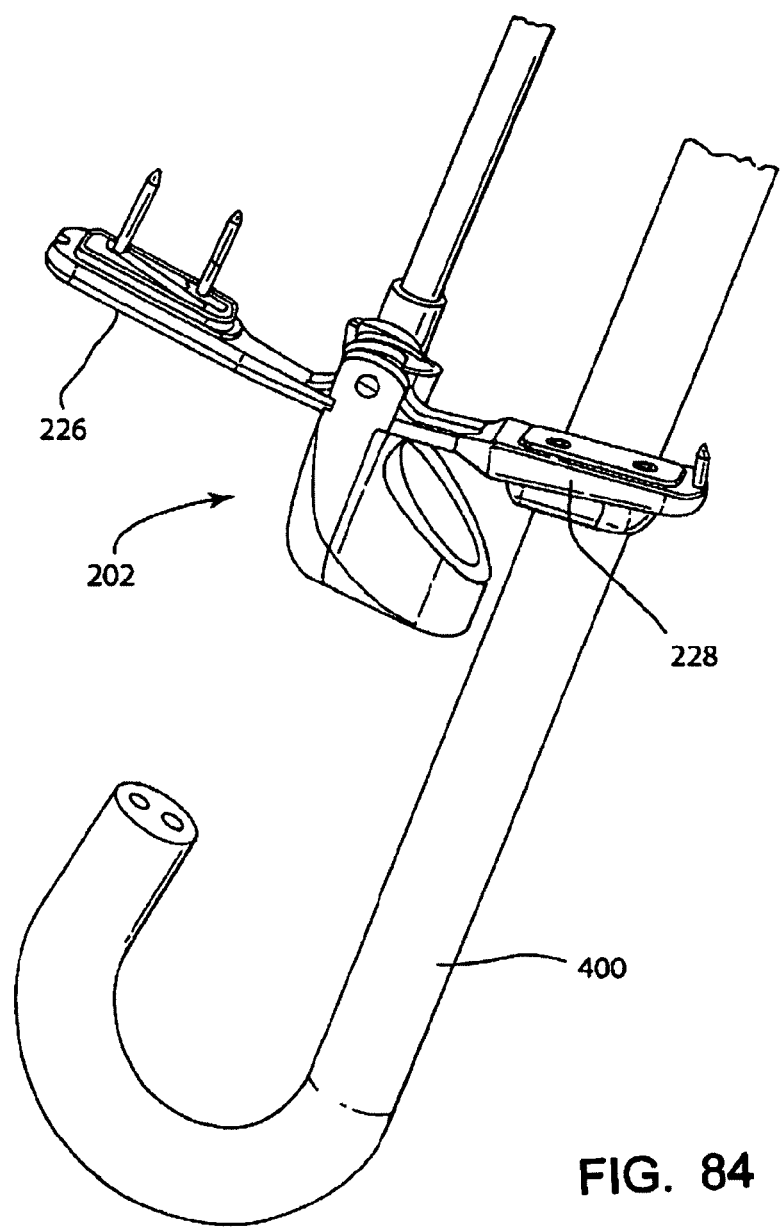
FIG. 84 is a fragmentary, side perspective view of the instrument according to the invention separated from the endoscope with the jaws in an open position.

If the endoscope is retroflexed during insertion of the distal end effector 202, the passage of the distal end effector into the stomach is performed under view of the endoscope 400. Once the distal end effector is located in the stomach, the endoscope is, preferably, straightened, if it was retroflexed, and the end effector is moved distally off the endoscope such that the endoscope 400 and instrument 200 are completely separated. Referring to FIG. 84, the endoscope 400 is then, again, retroflexed and the instrument handle 204 is operated to open the jaws 226, 228 of the end effector 202, as described above.

Figure 85:
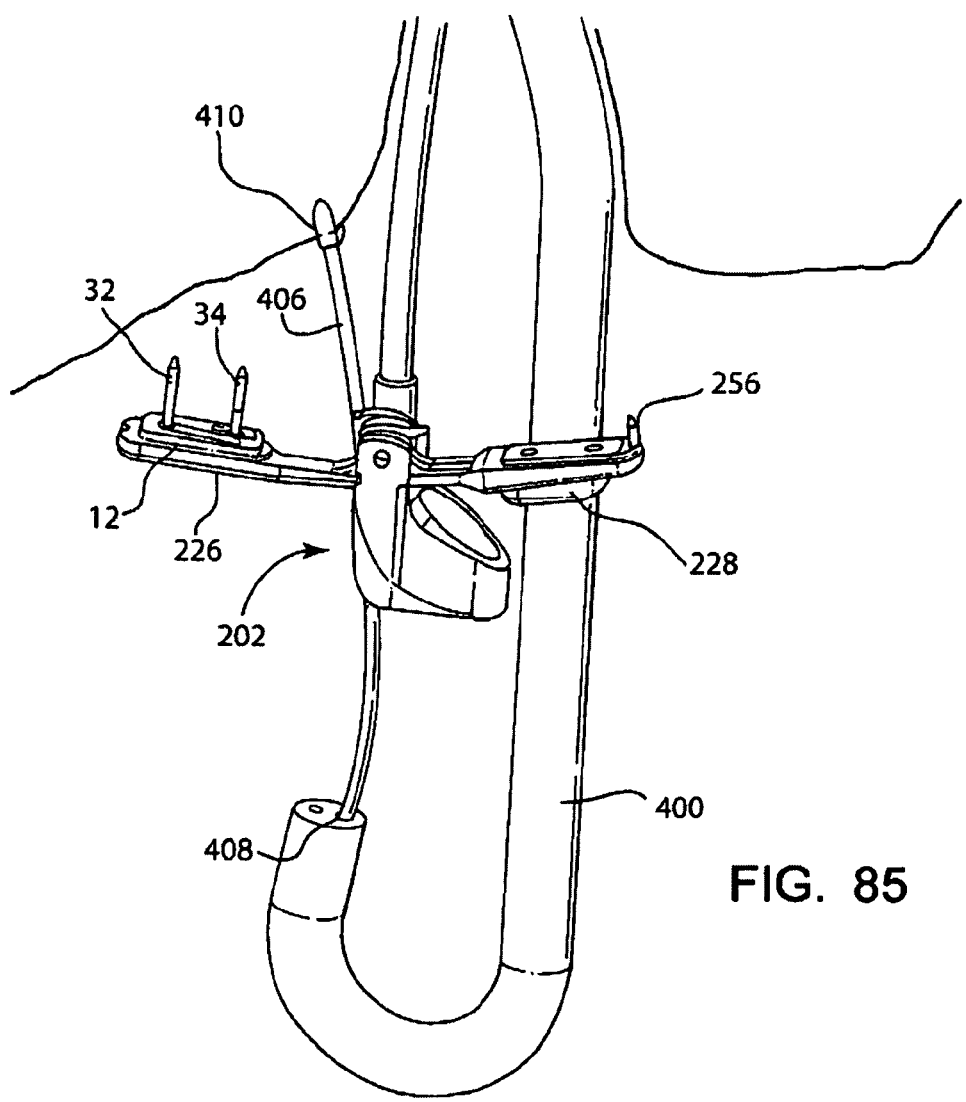
FIG. 85 is a fragmentary, side perspective view of the instrument of FIG. 84 with a grasping instrument advanced through the endoscope and engaging target tissue at which a plication is desired to be made.

Referring to FIG. 85, a tissue-grasping instrument 406, e.g., a forceps, helical needle, needle retractor, or tagging device, is, preferably, then inserted through a working channel 408 of the endoscope 400 and is directed at target tissue 410 one to three centimeters into the stomach adjacent the LES where the center of a plication is to be located. The grasping instrument 406 engages the tissue 410 and pulls the tissue back between the jaws 226, 228 of the end effector 202 of the instrument 200. In addition, the handle 204 and/or control shaft 206 of the instrument 200 are pulled back in gross (i.e., in the direction of withdrawing the instrument) such that the jaws approach the tissue 410 in a direction substantially parallel to the esophagus. This is a highly desirable angle of approach that has been previously unattainable with endoscopic GERD treatment instruments, that is, any device that retroflexes must extend through an arc.

Figure 86:
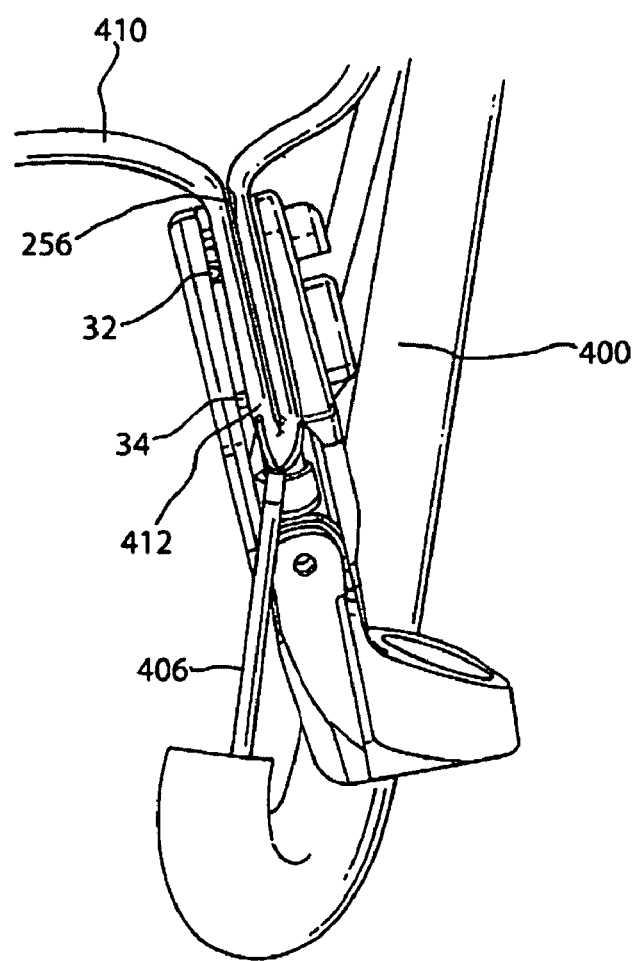
FIG. 86 is a fragmentary, side perspective view of the instrument of FIG. 85 with the jaws of the instrument plicating the target tissue and the fastener in a locked configuration.

The proximal actuation handle 204 is, then, operated to cause the jaws 226, 228 to close, as shown in FIG. 86. As a central point of the tissue 410 is held in a fixed location between the jaws by the grasping instrument 406 during movement of the jaws, a tissue plication 412 is formed by the jaws as the male and female parts 12, 14 of the fastener 10 are brought together with the plication 412 clamped therebetween. When the jaws 226, 228 are closed about the tissue plication 412, the posts 32, 34 of the male part 12 of the fastener 10, preferably, pierce the tissue down to the serosa, and the piercing post 256 of the female jaw 228, preferably, pierces through the deep muscle of the tissue sufficiently to damage the tissue to cause serosa-to-serosa contact. Experimental procedures have shown that serosa-to-serosa contact results in tissue adhesion after healing, such that the tissue is permanently reconfigured, i.e., even if the fastener 10 is removed later. In this manner, a zone of reduced compliance is created about the LES.

The location and size of the plication as well as the relative positions of the fastener parts are observed through the endoscope. Moreover, more or less clamping pressure can be applied to the plicated tissue by control of the proximal actuation handle 204.

At this point, it is noted that various natural complications exist when the posts 32, 34 first contact the tissue 410 and when the posts 32, 34 are passing through the tissue 410 on the way to the holes 58, 60 in the female part 14 of the fastener 10. When the posts 32, 34 are held in the male part 12 with any lateral play, slight misalignment can occur when there is no obstacle between the tip 323, 343 of the post 32, 34 and the holes 58, 60, for example, due to gravity acting upon the male part 12 when it is not exactly level with ground. When the posts 32, 34 are required to pass through tissue on the way to the holes 58, 60, substantially increased forces act upon the posts 32, 34. These forces are created in various ways.

One kind of force is generated because the tissue 410 is not homogeneous in density. Thus, as the posts 32, 34 pass through the tissue 410 (the inner post 34 passing through the tissue 410 before the outer post 32 due to its tighter arc of travel), more dense areas in the tissue 410 can cause deflection of a post 32, 34 out of its intended direction of travel.

More significantly, however, is the fact that the tissue 410 is being compressed between the jaws 226, 228 as the jaws 226, 228 close. Such compression is not uniform. The tissue 410 between the post 34 closest to the clevis 224 (referred to herein as the inner post 34) is compressed more than the tissue 410 that, ultimately, will be in between the inner post 34 and the other post 32 (referred to herein as the outer post 32). The tissue 410 near the outer post 32 further away from the clevis 224 will be compressed even less. Therefore, the most compressed tissue 410 near the clevis 224 will impart a different and more substantial lateral load on the inner post 34 than the lateral load imposed on the outer post 32, in particular, a load directing the inner post 34 toward the outer post 32 and away from the hole 60.

To account for these forces, as mentioned above, the chamfered openings of the holes 58, 60 (see FIG. 6) facilitate mating with the posts 32, 34 by guiding the posts 32, 34 into the holes 58, 60 if the parts 12, 14 are misaligned slightly. The chamfered opening, however, may not be sufficient. Therefore, each post 32, 34 can be altered to overcome the lateral forces. First, the post 32, 34 can be manufactured with an increased diameter or a beveled diameter (see, e.g., FIG. 8). Second, the holds 58, 60 can be created with a diameter substantially larger than the outer diameter of the post 32, 34.

Figure 87:
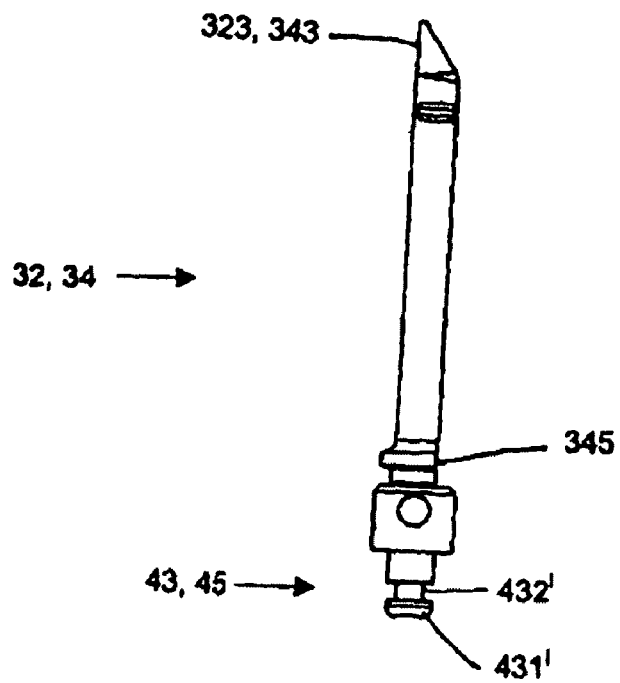
FIG. 87 is a side elevational view of an alternative embodiment of a post of FIGS. 1 to 10 separated from the male part of the fastener.
Figure 88:
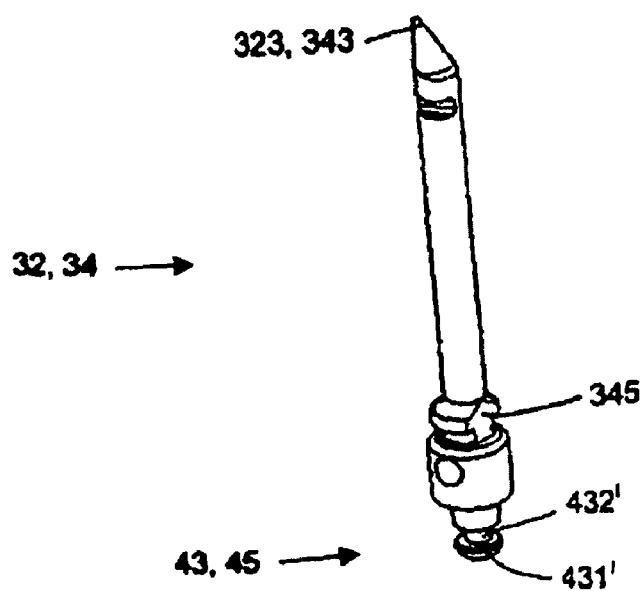
FIG. 88 is a perspective view of the post of FIG. 87.

A preferred adaptation of the post 32, 34 lies in creating a tip 323, 343 that guides the post 32, 34 in an optimal direction for mating with the holes 58, 60. Such a tip 323, 343 is illustrated, for example, in FIGS. 87 and 88. The tip 323, 343 shown in FIGS. 87 and 88, instead of being centered along the central longitudinal axis of the post 32, 34 is, instead, off-axis. The off-axis distance can be slight, or, as shown in FIGS. 87 and 88, can be such that an end of the tip 323, 343 lies at the outer circumferential surface (shown best in FIG. 87). Alternatively, depending on manufacturing considerations, it may be easier to merely bend the tip 323, 343 in the desired direction to move the end of the tip 323, 343 off-axis. In such a case, the end of the tip 323, 343 can be further away from the central longitudinal axis of the post 32, 34 than a substantial portion of the outer circumferential surface thereof. Because the preferred configuration of the posts 32, 34 is not axially symmetric, see flattened area 345 in FIGS. 9, 87, 88, when the posts 32, 34 are installed in the male part 12 in a given orientation, the tip 323, 343 will be positioned in the desired location.

With regard to the inner post 34, the force imparted by the folded tissue 410 (see FIG. 86) is directed towards the outer post 32. Therefore, to counteract this force, the off-axis direction of the tip of the inner post 34 is placed closer to the clevis 224. Such placement allows the inner post 34 to move directly toward the holes 58, 60 in spite of the lateral force by faking advantage of the density of the tissue 410. Because the tip 323, 343 is off-axis, parting of the tissue 410 around the post 32, 34 will tend to burrow the tip 323, 343 in a direction opposite the forces acting upon the post 32, 34, thus negating the lateral force caused by tissue 410 compression. The tip 323, 343 shown in FIGS. 87 and 88 is only illustrative and can be made in any shape that will counteract forces tending to move the tip 323, 343 in a direction that is not towards the hole 58, 60.

Figure 89:
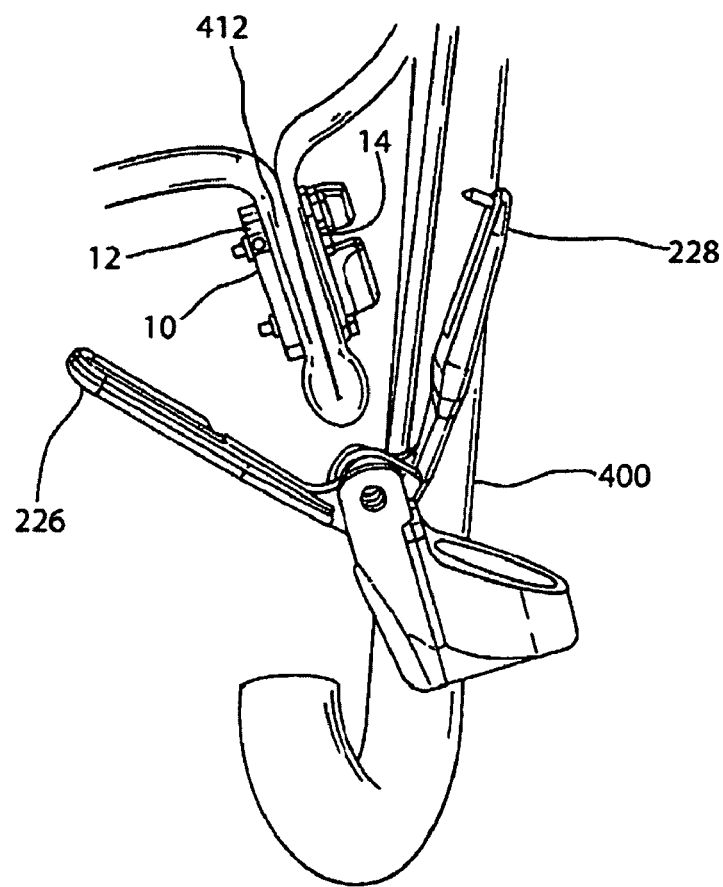
FIG. 89 is a fragmentary, side perspective view of the instrument of FIG. 86 with the jaws of the instrument in an open position and the fastener holding the plicated tissue together.

Referring to FIG. 89, if the plication 412 appears satisfactory (and if the user has visual confirmation that the alignment markers 214, 215 or other indicators 219, 227, 293, 295 are aligned with one another—thus, providing the user with the information that the fastener 10 is in a proper implantation position)—the proximal actuation handle 204 is operated, as described above, to lock the male and female parts 12, 14 of the fastener 10 and release the coupled fastener from the jaws 226, 228. If the plication or fastener position is not satisfactory, or if the alignment markers 214, 215 or indicators 219, 227, 293, 295 are not aligned, prior to locking and release, the jaws can be opened and reoriented if necessary, and another plication can be formed.

After the fastener is applied, the jaws are, then, closed to the overtouch position, the endoscope is straightened, and the end effector is re-docked over the distal end of the endoscope. The instrument and endoscope are together withdrawn through the esophagus and out of the patient. Alternatively, the endoscope may be withdrawn first, followed by the withdrawal of the instrument, preferably, under visualization with the endoscope.

As discussed above, if, at any time, the fastener or either of the parts thereof becomes loose during the implantation procedure or any time after the procedure, the sharps on the fastener elements are adapted to assume a safe configuration or are covered permanently. As such, the fastener or its parts may be safely passed through the gastrointestinal system of the patient.

Figure 90:
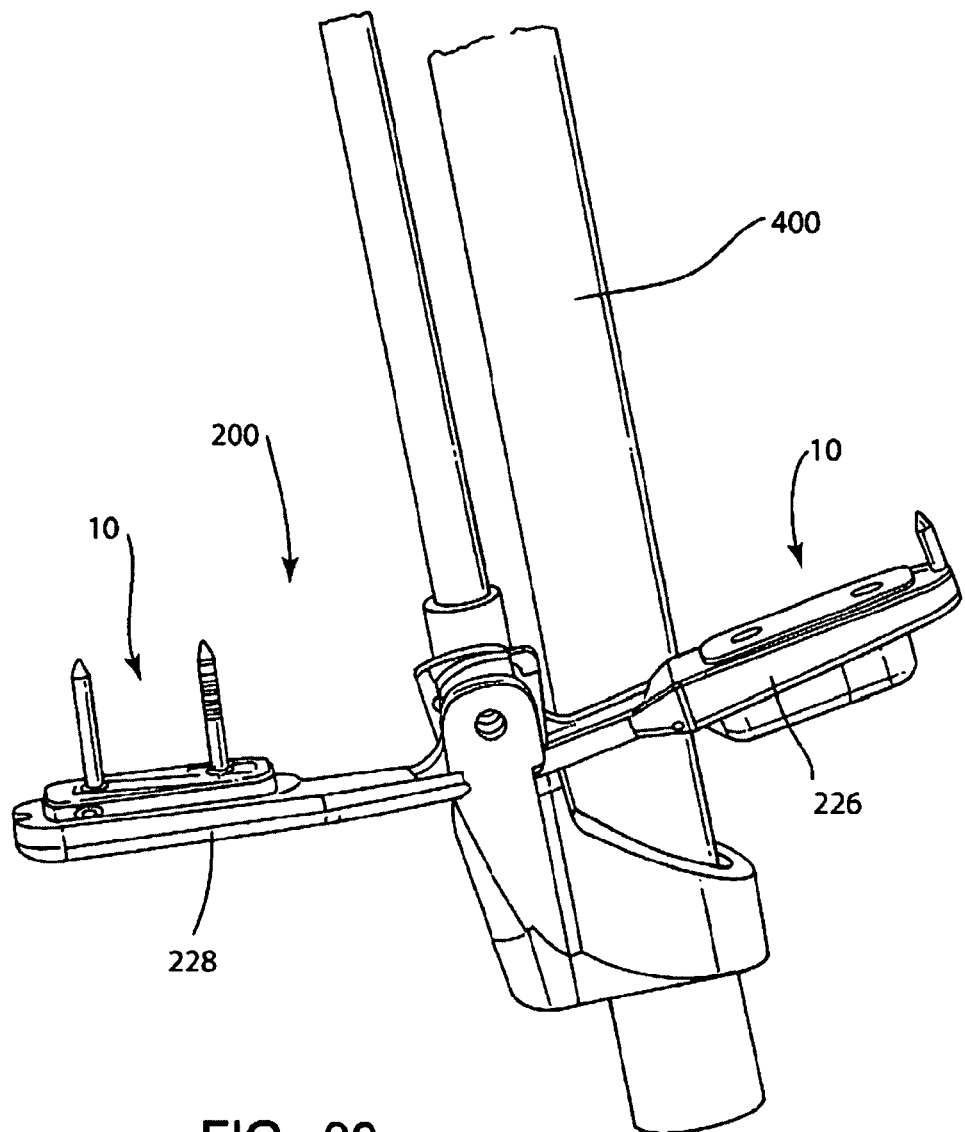
FIG. 90 is a fragmentary, perspective view of the instrument of FIGS. 84 to 86 in an alternative procedure in which the end effector is operated while coupled to an endoscope.

While it is preferable to decouple the instrument from the endoscope during the procedure, it is appreciated that the instrument may be operated while coupled to the endoscope. That is, referring to FIG. 90, the target tissue is approached by opening the jaws 226, 228 and simply retracting the instrument 200 along the endoscope 400 until the tissue about the LES is contacted. The jaws 226, 228 are, then, closed and the fastener 10 applied, as described above. In order to utilize such a procedure, the sleeve 320 of the instrument should be offset relative to the jaws 226, 228 so that the jaws can clear the endoscope when opening and closing. Such a procedure might, advantageously, incorporate the use of a rear-looking endoscope.

Figure 91:
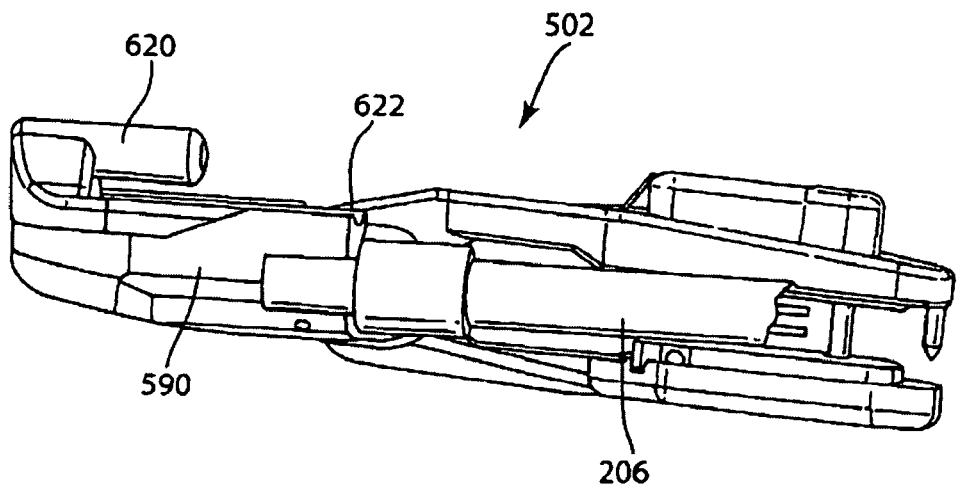
FIG. 91 is a side elevational view of another embodiment of the distal end effector according to the invention adapted to be coupled in the distal opening of a working channel of an endoscope.
Figure 92:
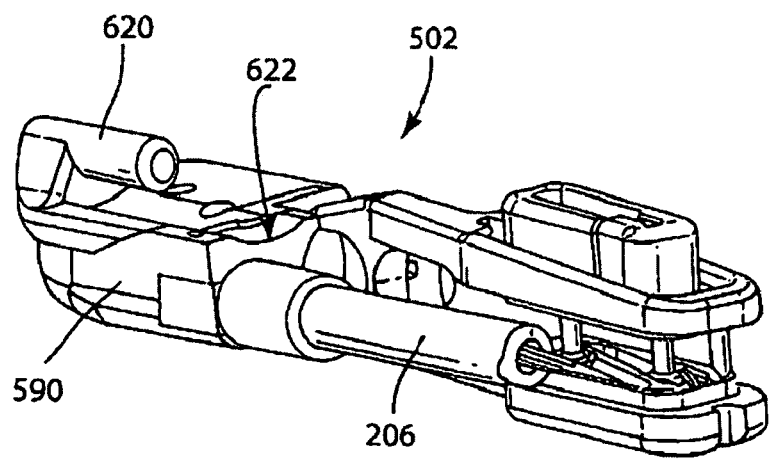
FIG. 92 is a perspective view of the embodiment of the distal end effector of FIG. 91 from a side thereof.

Turning now to FIGS. 91 and 92, a first alternative embodiment of a distal end effector 502 of the instrument 200 according to the invention is shown. The end effector 502 is adapted to couple within the distal end of a working channel of an endoscope, rather than be coupled about the endoscope with a sleeve. To that end, the housing 590 of the end effector 502 is provided with a proximally directed peg 620 preferably located above, but in line with, the control shaft 206 and sized to be received within the distal end of a working channel of an endoscope. In addition, the housing 590 also includes a concave surface 622 permitting the housing 590 and endoscope to be adjacent in a minimized profile.

In use, the end effector is docked with the distal end of the endoscope using the peg 620, and the control shaft 206 is held taught relative to the endoscope to maintain the coupling. The cross-sectional area for the system at the end effector (end effector and endoscope coupled together) is approximately 150 mm². It is noted that the cross-sectional area of such a system is smaller than the area defined by a system utilizing a sleeve, as the endoscope is close fitting with the end effector and the sleeve dimensions are eliminated. The endoscope, with end effector 502 attached at its distal end, is, then, inserted into the patient's stomach. The proximal handle 204 and/or control shaft 206 is, then, manipulated in gross to disengage the end effector. Thereafter, the procedure continues, preferably as discussed above, until plication and fastener application is achieved. Then, prior to removal of the instrument and endoscope, the end effector 502 is re-docked with the endoscope, and the instrument and endoscope are withdrawn from the patient. Alternatively, the endoscope and instrument are separately removed.

Figure 93:
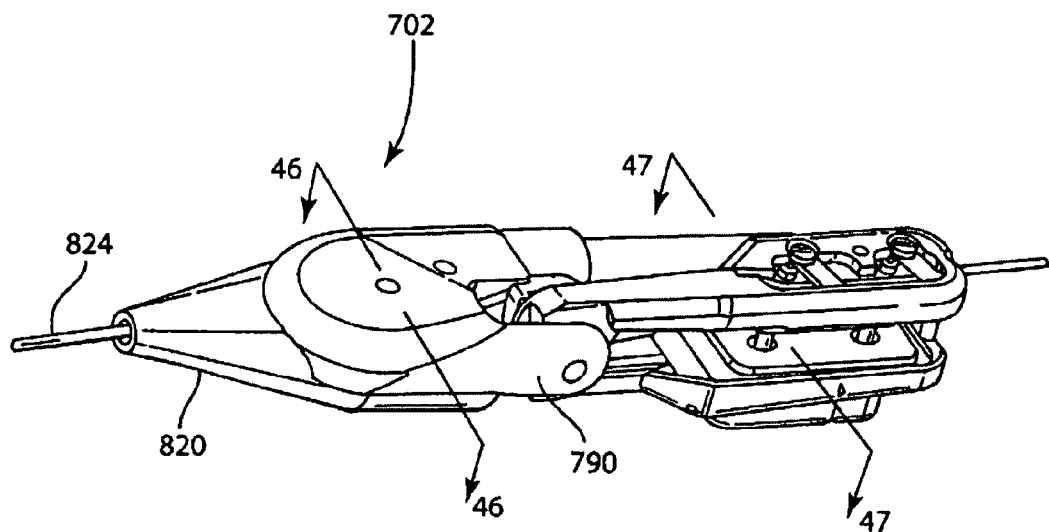
FIG. 93 is a perspective view of yet another embodiment of the distal end effector according to the invention adapted to be advanced over a guidewire.
Figure 94:
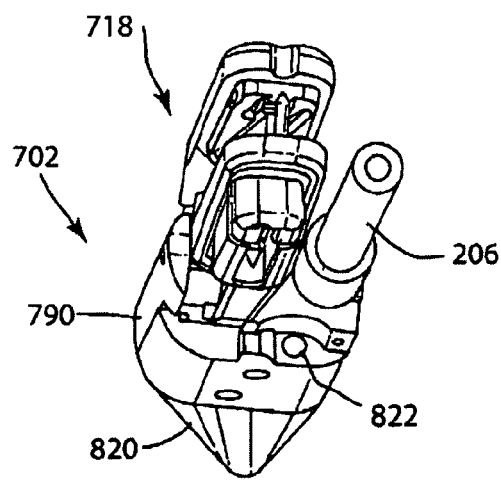
FIG. 94 is a perspective view the distal end effector of FIG. 93 from below and proximally thereof.

While the instrument has been shown adapted to be coupled to an endoscope, it is recognized that the instrument may be modified for use in a manner in which it is always decoupled from an endoscope. Referring now to FIGS. 93 and 94, a second alternative embodiment of the distal end effector 702 of the instrument 200 is shown. The housing 790 of the end effector 702 is provided with a tapered nosepiece 820 defining a longitudinal passage 822 sized to receive a guidewire 824. The guidewire 824 may have a diameter less than one millimeter. Preferably, the nosepiece 820 is formed from a highly flexible material such as silicone.

FIGS. 38 through 47 and 52 through 66 illustrate a third, preferred, alternative embodiment of the distal end effector 802 of the instrument 200. The housing 890 of the end effector 802 is provided with a rounded and tapered nosepiece 820 defining a longitudinal passage 822 sized to receive a guidewire 824. The guidewire may have a diameter less than one millimeter. Preferably, the nosepiece 820 is formed from a highly flexible material such as silicone but can also be stainless steel.

Figure 95:
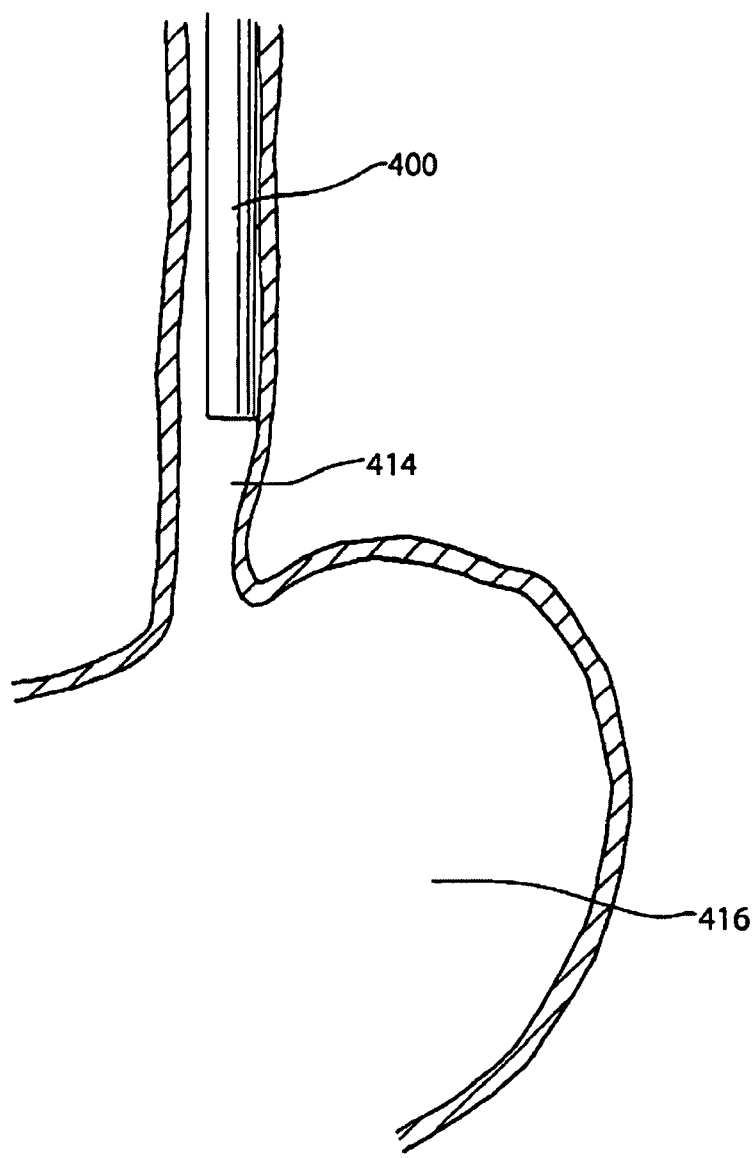
FIGS. 95 through 105 are fragmentary partially cross-sectional and partially elevational views illustrating another embodiment of the procedure according to the invention in which the end effector is advanced over a guidewire into the stomach and operated under view of an endoscope.
Figure 96:
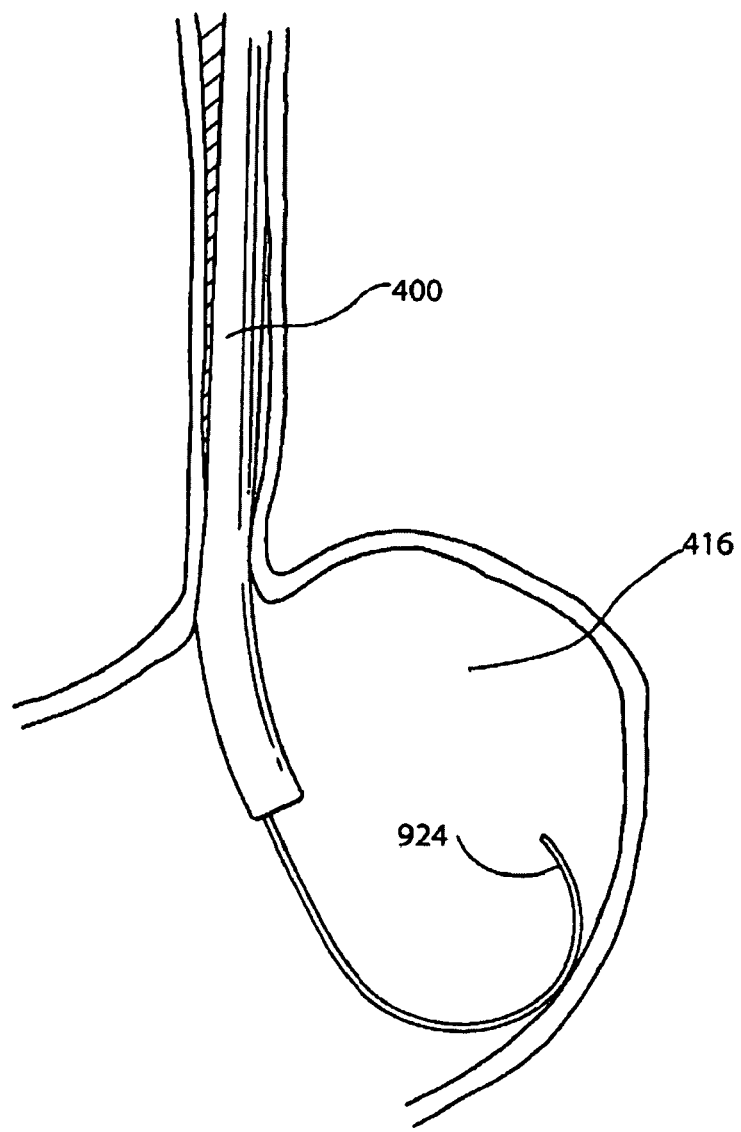
Figure 97:
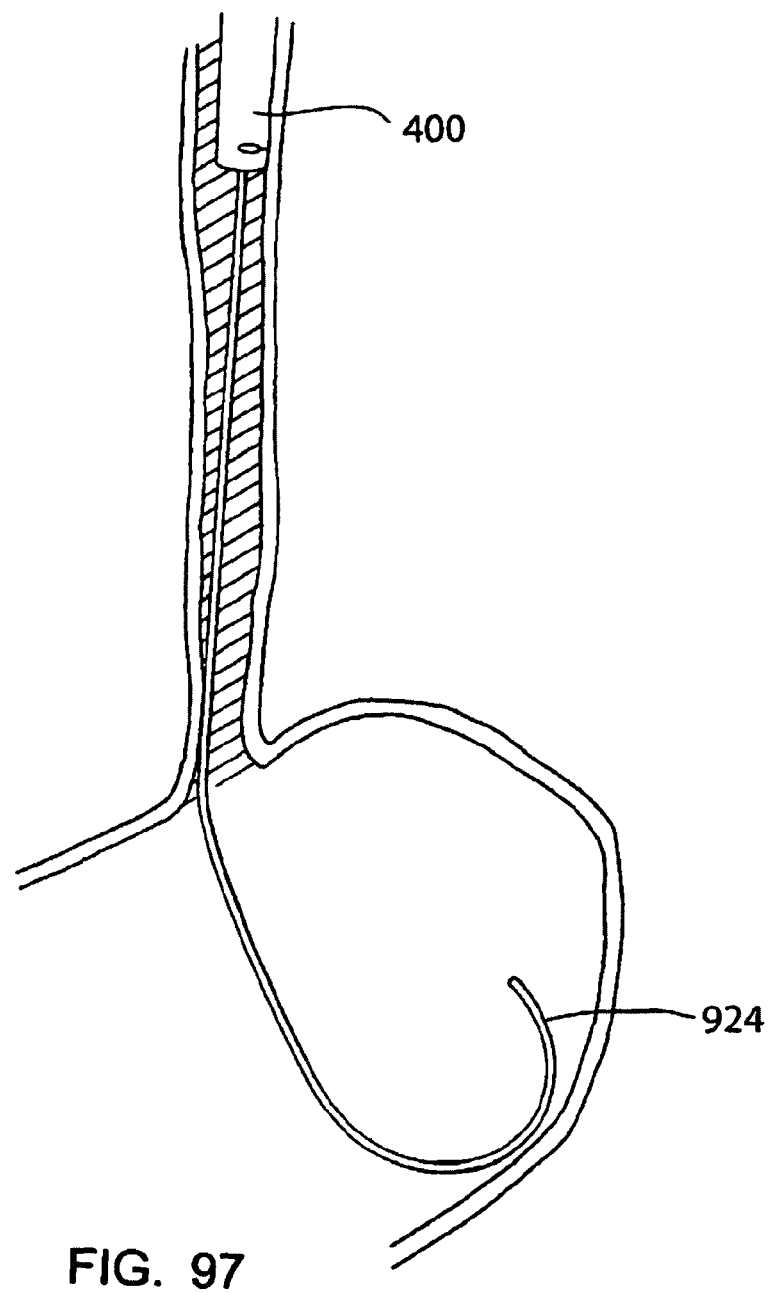
Figure 98:
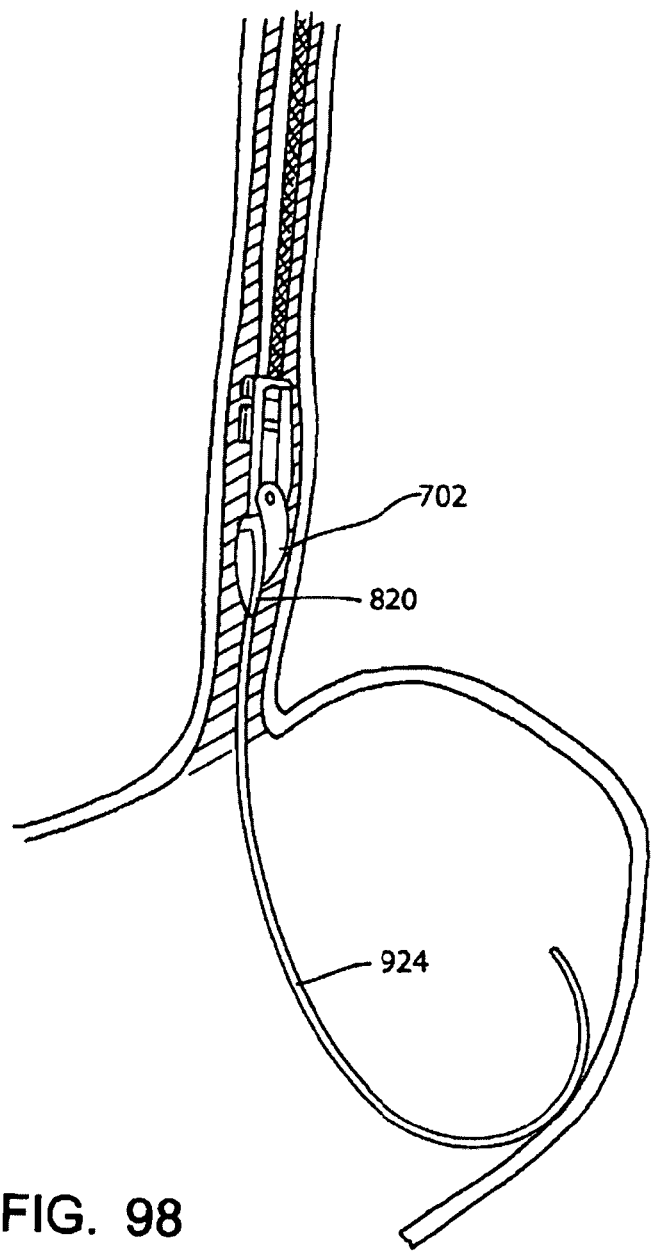
Figure 99:
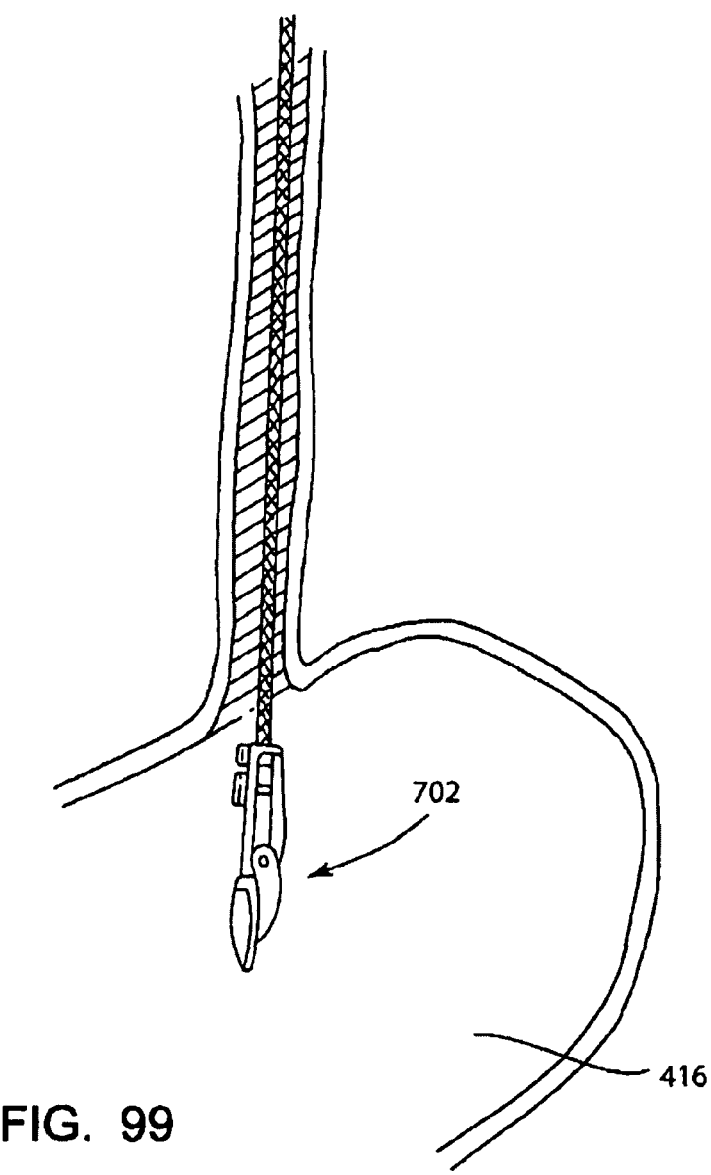

According to a preferred method of use, referring to FIG. 95, an endoscope 400 is, preferably, first inserted past the Cricopharyngeal Junction, through the gastroesophageal junction 414, and into the stomach 416 in accord with a well-known procedure. Next, referring to FIG. 96, a guidewire 924 is advanced through the endoscope 400 into the stomach 416. Referring to FIG. 97, the endoscope 400 is, then, preferably withdrawn from over the guidewire 824. Referring to FIG. 98, the end effector 702 is, then, blindly advanced over the guidewire 924 and introduced into the stomach 416. The tapered nosepiece 820 and relatively small head-on cross-sectional area of the system facilitate the introduction. Referring to FIG. 99, after the end effector 702 is located in the stomach 716, the guidewire 824 is, preferably, withdrawn from the stomach 716.

Figure 100:
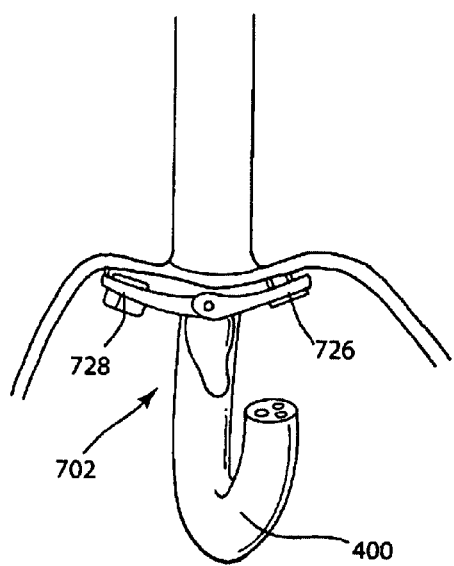
Figure 101:
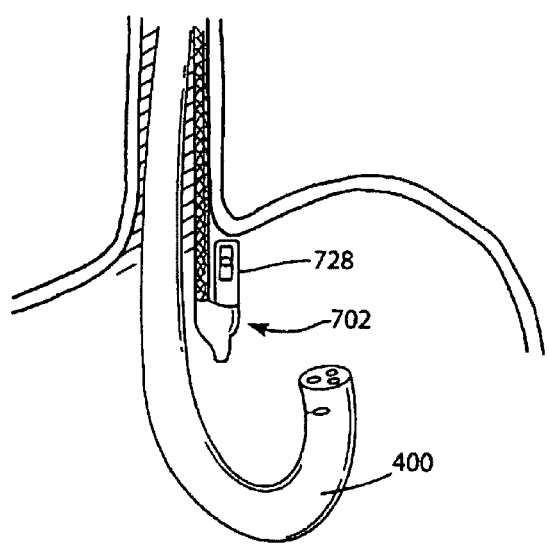
Figure 102:
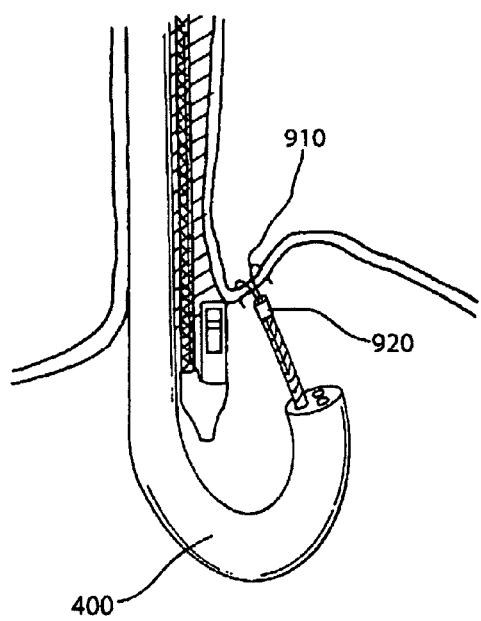
Figure 103:
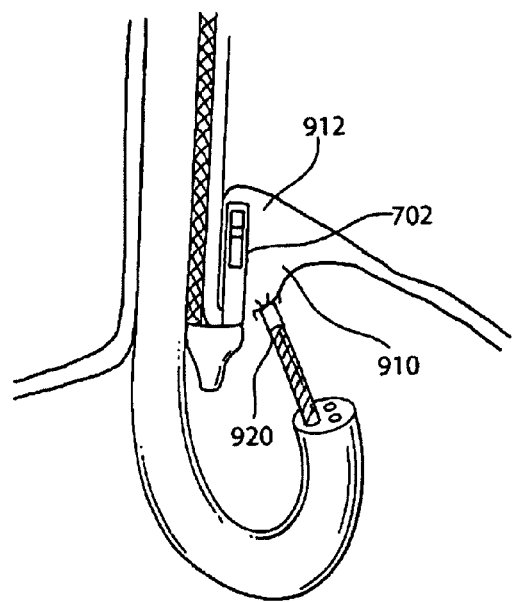
Figure 104:
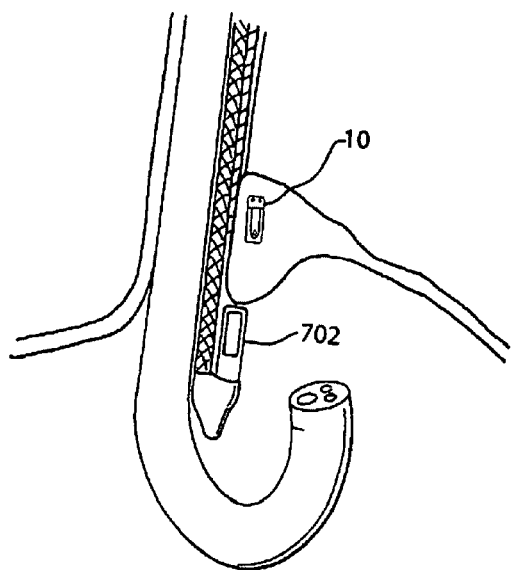
Figure 105:
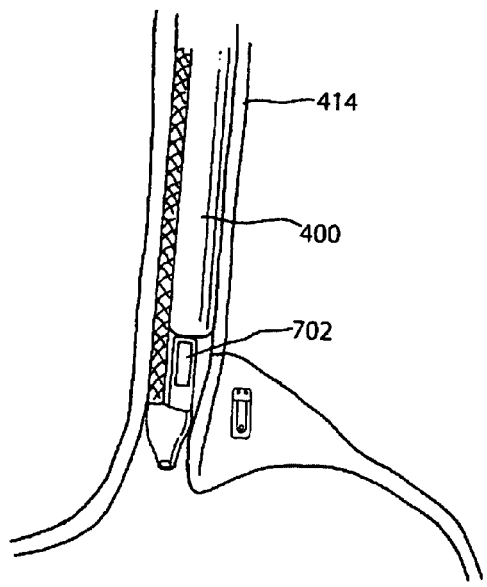

Referring now to FIGS. 100 and 101 the endoscope 400 is, then, reintroduced alongside the control shaft 206 of the instrument, advanced into the stomach 716, and retroflexed to view the end effector 702. The jaws 726, 728 of the end effector 702 are, also, opened and brought adjacent the tissue 910 that is to be plicated. Referring to FIG. 102, a tissue-grabbing device 920 is deployed through a working channel 408 of the endoscope 400 and operated to engage tissue 910 at a location at which the fold of a plication is desired. The tissue-grabbing device 920, preferably, includes piercers that extend through the mucosa and the muscularis (deep muscle) to, thereby, hold these layers together and prevent delamination. Turning to FIG. 103, the jaws of the end effector 702 are closed, forming a plication 912 about the engaged tissue 910, the plication 912 being substantially parallel to the esophagus. The plication 912 extends from the location held by the tissue-grabbing device 920 to the end of the jaws of the instrument 702. If implantation of the fastener 10 is considered to be good, the fastener 10 is locked and deployed. Then, the jaws of the end effector 702 are opened and withdrawn from the fastened plication 912, as shown in FIG. 104. Referring to FIG. 105, the jaws of the end effector 702 are closed, and the end effector 702 is withdrawn through the esophagus 414 under visualization of the endoscope 400. Preferably, the closed jaws of the end effector 702 are positioned directly distal of the endoscope 400 to minimize the cross-sectional area of the endoscope/instrument system as well as to permit constant visualization of the end effector during the retraction of the end effector through the esophagus, in particular, during retraction through the Cricopharyngeal Junction.

Figure 106:
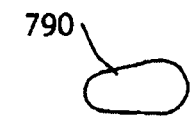
FIG. 106 is an end view schematic illustration of a cross-sectional area across line 106-106 in FIG. 93.
Figure 107:
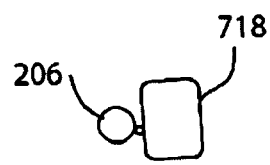
FIG. 107 is an end view schematic illustration of a cross-sectional area across line 107-107 in FIG. 93.

It is noted that this embodiment provides the smallest cross-sectional area for the system in the esophagus because the area is limited to either (1) the end effector or (2) the endoscope and control shaft, but not both (1) and (2) at the same time. Referring to FIG. 106, for (1), the end effector cross-sectional area across the clevis 790 distal of the jaw assembly is approximately 75 mm². Also for (1), the end effector cross-sectional area proximal of the clevis and across the jaw assembly 718 is (with the jaw assembly in a closed position) approximately 115 mm² (calculated as the approximately 102 mm² cross-sectional area of the jaw assembly 718 plus the 12.6 mm² cross-sectional area of a 4 mm control shaft 206). See FIG. 107. For (2), the combined cross-sectional area of the endoscope and control shaft is 76.2 mm², calculated as 63.6 mm² for a 9 mm endoscope and 12.6 mm² for a 4 mm control shaft.

The instrument 200, 2000 is highly torqueable with great ability to direct the end effector 202, 702, 802 through manipulation of the handle 204, 2002 in gross. That is, the instrument 200, 2000 has a torsionally rigid flexible shaft, particularly for its length of at least approximately 25 to 30 cm, and more likely approximately between 30 and 50 cm length. This torqueability permits the end effector assembly 202, 702, 802 to be rotated through 180° (for any approach toward target tissue) through rotation of the handle 204, 2002, preferably, by no more than approximately 180°. This is facilitated, in part, by rotationally fixing the control element 208 to the handle 340. The control element 208 is relatively large in diameter, and is, most preferably, an approximately 0.035 inch (0.0889 cm) stainless steel wire. A wire of similar construct having a diameter, preferably, between approximately 0.020 inch (0.0508 cm) and approximately 0.062 inch (0.1575 cm) is also suitable.

It is generally understood that twisting of endoscopic instruments to impart a torque to tissue is to be avoided and is an action that is not desirable. However, use of the instrument according to the present invention has revealed a surprising discovery that substantially improves stomach tissue plication and, therefore, provides significantly better results for treatment of GERD. The improvement arises from the instrument's (200, 2000) ability to rotate the end effector 202, 702, 802 in an almost 1:1 ratio, thus providing a very high degree of rotational controllability. Combined with a specific orientation of the male and female jaws 226, 228 as explained below, the present invention is the first that allows execution of the preferred plication method.

In the first embodiment of the plication method according to the present invention (described above), the retractor 920 pulls the target tissue 910 between the jaws 226, 228 as shown in FIG. 102. Thereafter, the jaws 226, 228 are closed about the target tissue 910 and, if a closed fastener 10 makes a satisfactory plication, the fastener 10 is locked and released as shown in FIG. 104.

Because the male jaw 226 is on a particular side of the end effector 202, 702, 802 (as shown, for example, in FIGS. 52, 54, 56, 58 to 66, and 68), when the end effector 202, 702, 802 is inserted in the stomach (see FIGS. 85, 86, 89, and, in particular, FIGS. 100 to 105), the male jaw 226 is positioned near stomach tissue 416 on an anterior side of the gastroesophageal junction (GEJ) or esophagus 414, which is a particularly advantageous position for the male jaw 226 (the female jaw 228 is, likewise, disposed at stomach tissue on a posterior side of the GEJ). As set forth above, the instrument 200, 2000 has the ability to move in a three-dimensional space completely independent of the endoscope 400. Such independent movement allows the jaws to be closed at the GEJ and create a plication that, tightens the GEJ in the treatment of GERD.

In the alternative preferred plication method, before the jaws 226, 228 are fully closed but after the posts 32, 34 have pierced the target tissue on the anterior side of the GEJ as clearly shown in FIG. 100, the handle 204, 2002 is rotated up to approximately 180° (counter-clockwise with respect to FIGS. 108 to 116). This rotation causes tissue pierced by the two posts 32, 34 at the anterior side of the GEJ to move around and behind (as viewed in FIG. 100) the endoscope 400, thus placing stomach tissue originally disposed at the anterior side of the GEJ at a final position near the posterior side of the GEJ. Such wrapping of the anterior-GEJ stomach tissue about the endoscope 400 creates a GEJ seal that is more constricted than the first plication method as described above.

Specifically, the posts 32, 34 anchor into anterior tissue at the GEJ and drag the anchored anterior tissue over towards an area where the female jaw 228 was originally placed (towards posterior) and about the tent/plication/bulge created between the jaws 226, 228 by the tissue retractor 920. The dragging is carried out by torqueing the instrument 200, 2000 in the appropriate direction (counter-clockwise with respect to FIGS. 108 to 116), which movement pivots the end effector 202, 702, 802 around the endoscope 400. Rotation of anterior-GEJ tissue towards the posterior side produces a plication between the jaws 226, 228 that is considerably larger than in the above-mentioned first plication method and is substantially larger to any prior art plication method. Simply put, by torqueing the instrument 200, 2000 with the posts 32, 34 engaged in the anterior-GEJ tissue, the jaws 226, 228 are allowed to incorporate much more GEJ tissue into the plication than tissue simply-disposed between two open jaws 226, 228. Such twisting also allows the user to gather an extended amount of tissue of the GEJ and approximate it for better anatomical placement of the fastener 10. Additionally, depending on the extent, of the torqueing/twisting/rotation, the new technique allows the user to select varying degrees of tightness of the tissue wrap around the endoscope 400. Tighter wrapping of the engaged tissue results in gathering more GEJ tissue into the plication, which creates a tighter GEJ seal after the fastener 10 is closed and locked.

Figure 108:
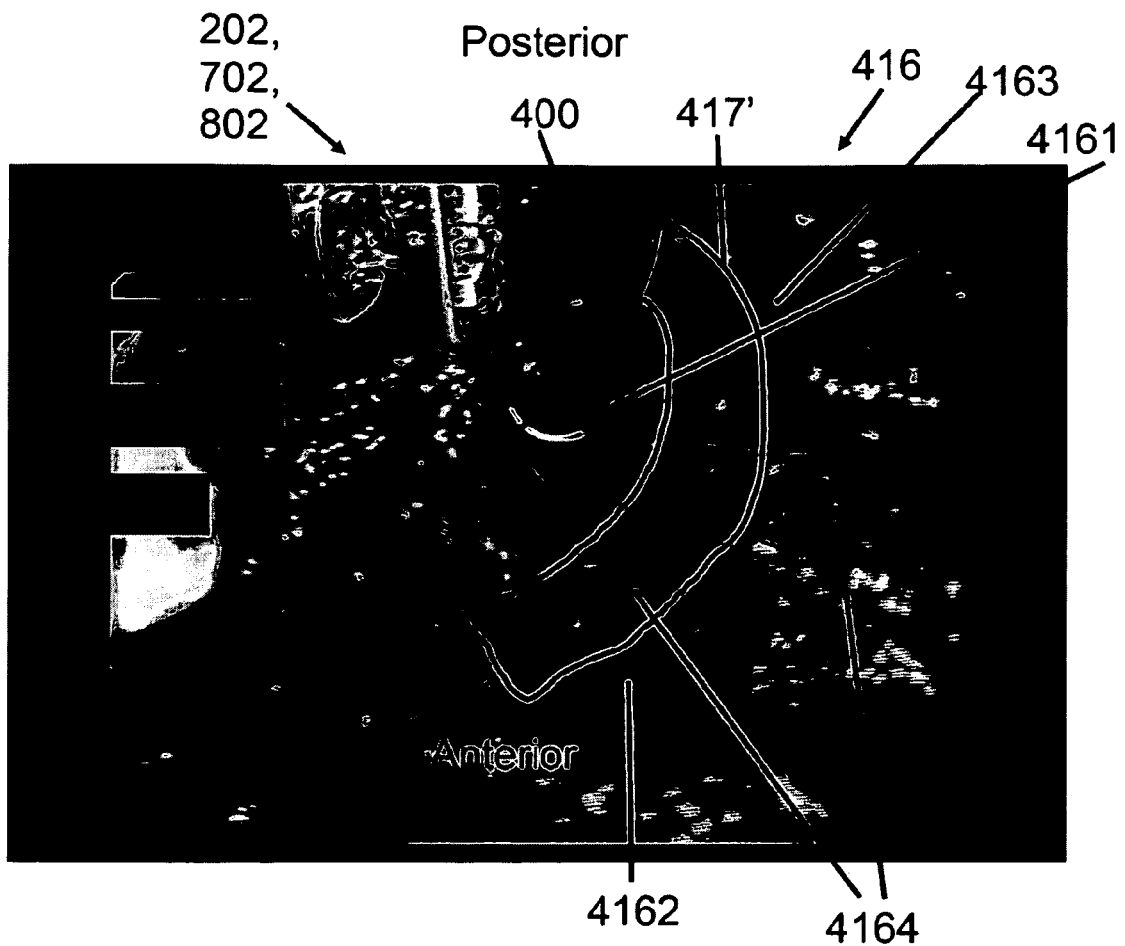
FIG. 108 is a color photograph of stomach and GEJ tissue viewed from an inside of the stomach towards the esophagus showing a portion of an endoscope and an end effector, in a closed position, inside the stomach.

This second embodiment is now described with reference to FIGS. 108 to 111, which are pictures of the end effector 202, 702, 802 inside a human stomach. FIG. 108 is a view from a camera at a distal end of an endoscope 400 that is disposed inside the stomach along with the end effector 202, 702, 802. The endoscope 400 and the end effector 202, 702, 802 in FIG. 108 are in a position similar to that shown in FIG. 101. The bottom of FIG. 108 is an anterior side 4162 of the GEJ 4161 and the top of FIG. 108 is a posterior side 4163 of the GEJ 4161. A tissue fold 4164 is clearly shown in FIG. 108. This fold 4164 has a parabolic shape with the opening of the parabola facing the right side of FIG. 108.

Figure 109:
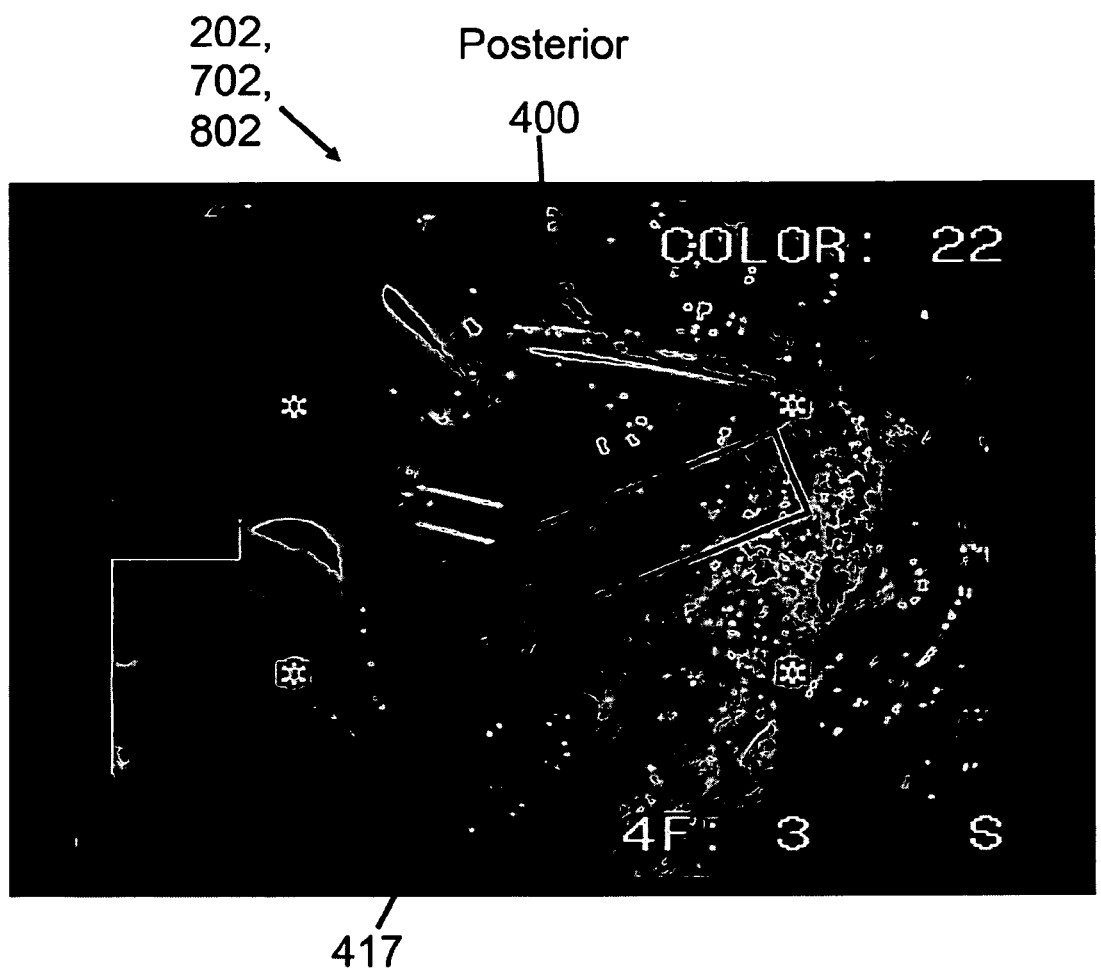
FIG. 109 is a color photograph similar to FIG. 108 with the end effector in an open position inside the stomach.
Figure 110:
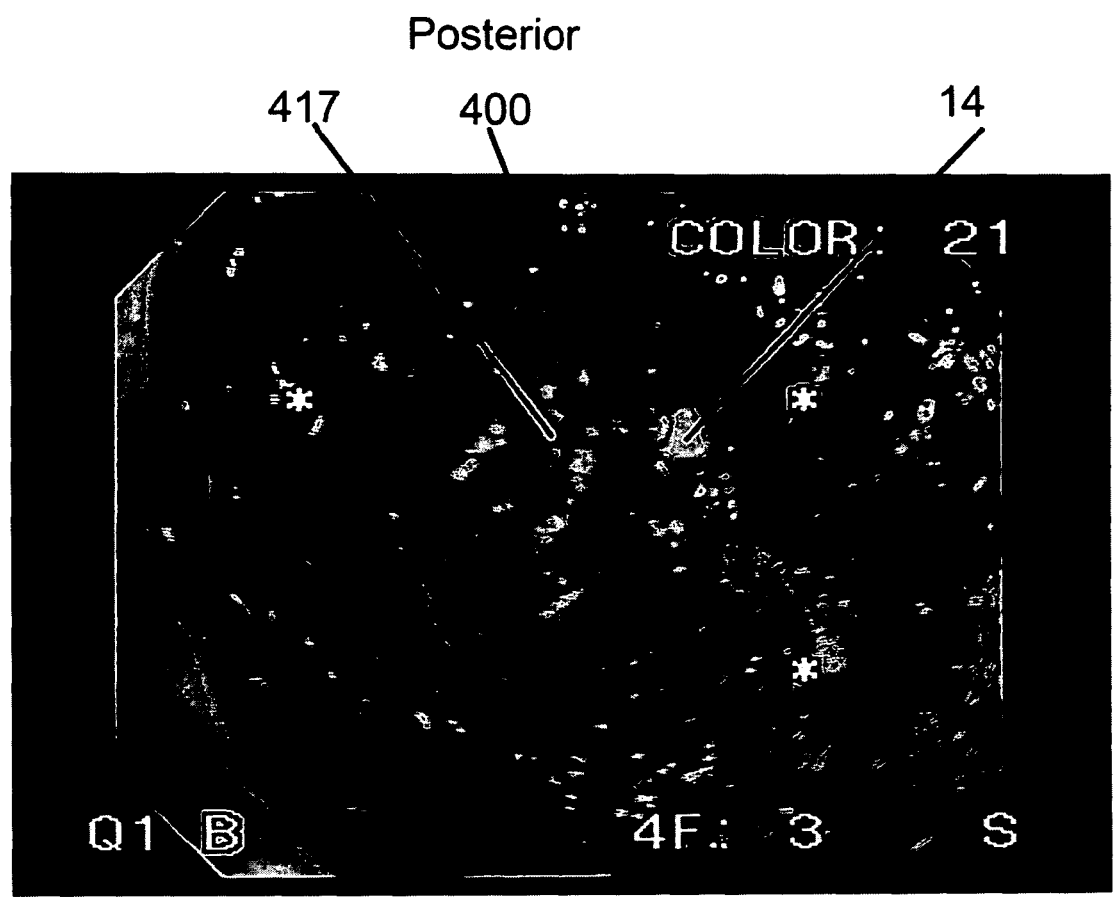
FIG. 110 is a color photograph similar to FIG. 108 with the end effector closed about plicated stomach and/or GEJ tissue.
Figure 111:
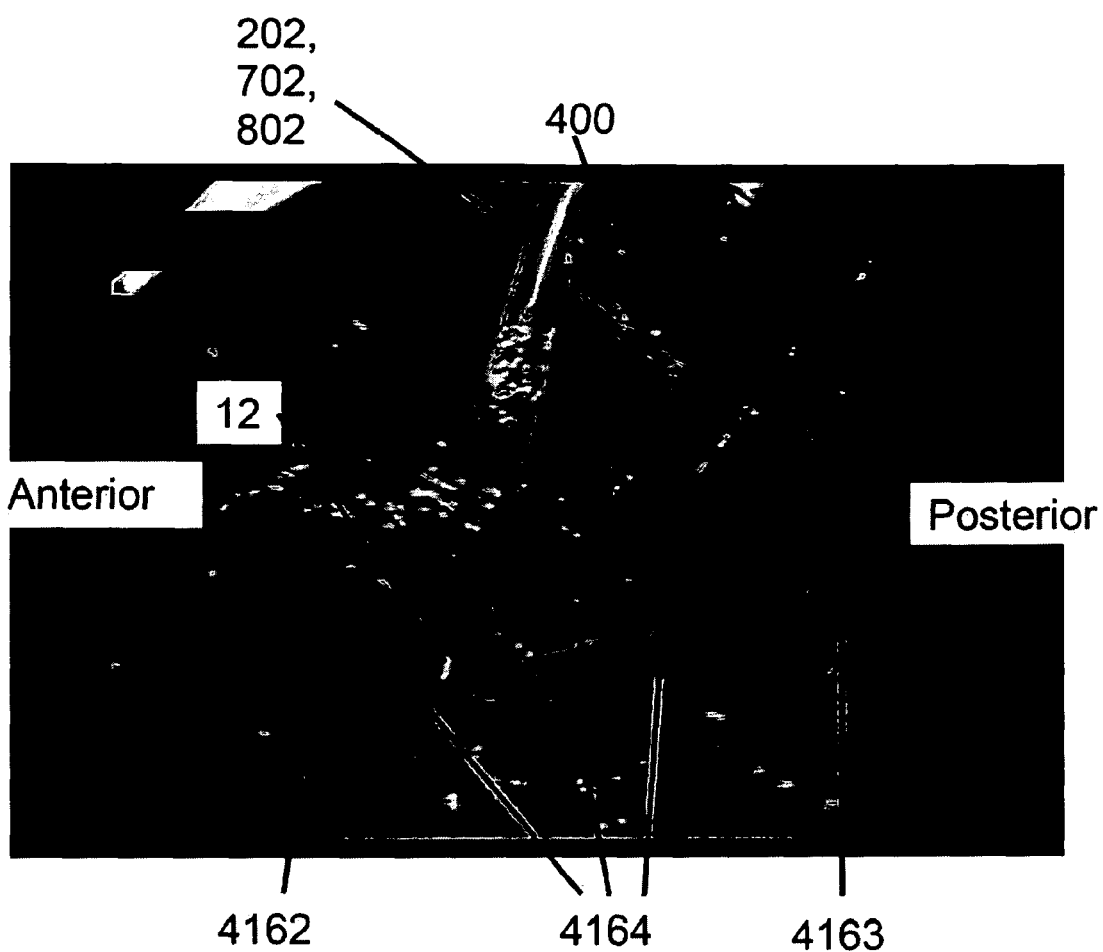
FIG. 111 is a color photograph similar to FIG. 108 with the end effector in the closed position and stomach and/or GEJ tissue plicated by a locked fastener.

FIG. 109 shows the end effector 202, 702, 802 with the jaws 226, 228 open and about to be moved proximally to engage target tissue 417 in the region of the GEJ 4161. The initial target tissue 417 is the same tissue that is plicated with the first embodiment of the method according to the present invention. The area forming the target tissue 417 is approximately rectangular in shape (or ovular due to the viscoelastic nature of the tissue 417). In contrast thereto (see FIGS. 108 and 115), the area defining the target tissue 417' of the second plication embodiment is arc-shaped and is substantially larger than the initial target tissue 417. Thus, more tissue is gathered into the plication in the second embodiment. The amount of tissue 417' actually used for the plication is illustrated in FIG. 110 as a large bulbous mass in the center of the figure. The plicated tissue is so large that only a small portion of the female part 14 can be seen in FIG. 110. FIG. 111 shows the resulting plication fastened by an implanted fastener 10. A small portion of the fastener 10 can be seen on the anterior side 4162 of the GEJ 4161. A comparison of the tissue folds 4164 in FIGS. 108 and 111 reveals a very tight seal about the endoscope 400. Thus, when the endoscope 400 and end effector 202, 702, 802 are removed from the stomach, a strong GEJ seal remains to treat and/or cure GERD.

Figure 112:
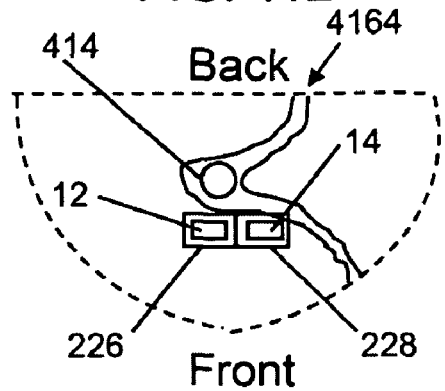
FIG. 112 is a diagrammatic plan view from a bottom of a stomach looking upwards towards the esophagus with an end effector in the stomach in an open position.
Figure 115:
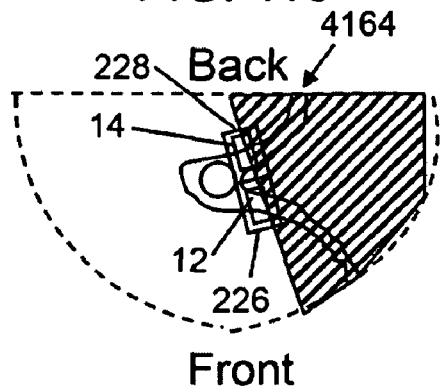
FIG. 115 is a diagrammatic plan view from the bottom of the stomach of FIG. 112 with the end effector in an open position at the right side of the esophagus and about both anterior and posterior portions of the Z-line.
Figure 113:
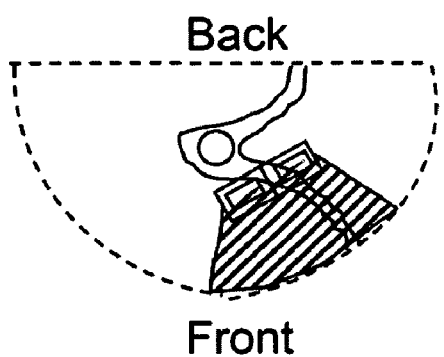
FIG. 113 is a diagrammatic plan view from the bottom of the stomach of FIG. 112 with an end effector in an open position about a Z-line.

The second plication method is further illustrated in FIGS. 112 to 116. FIG. 112 is a diagrammatic view from inside a stomach 416 looking upwards towards the esophagus 414. The stomach 416 has a hemispherical shape in FIGS. 112 to 116 to illustrate the fact that a person's back (bones and muscle) somewhat flattens the posterior side of the stomach 416. This shape is somewhat exaggerated for the sake of clarity. The open position of the jaws 226, 228 shown in FIGS. 100 and 109 is also shown in FIG. 112.

In the first plication method, the male and female parts 12, 14 of the fastener 10 grasp tissue at the GEJ, for example, at a location shown in FIG. 112. Alternatively, the jaws 226, 228 can be placed on either side of the tissue fold 4164 such that after closing the fastener 10, a foldings-back of the tissue fold 4164 lies between the fastener parts 12, 14. As can be seen by the striped area in FIG. 113, when the jaws 226, 228 grasp GEJ tissue without torqueing or twisting of the end effector 202, 702, 802, the area of GEJ tissue that becomes available for the plication is relatively small in comparison to a full 360° about the esophagus 414.

Figure 116:
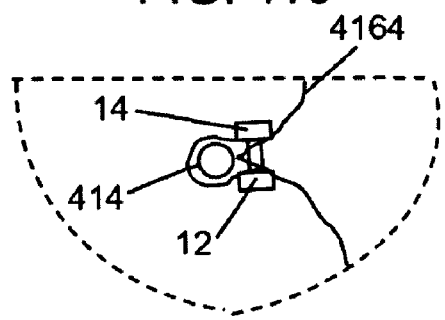
FIG. 116 is a diagrammatic plan view from the bottom of the stomach of FIG. 115 with a fastener plicating stomach tissue to the right of the esophagus according to a second method of the invention.
Figure 114:
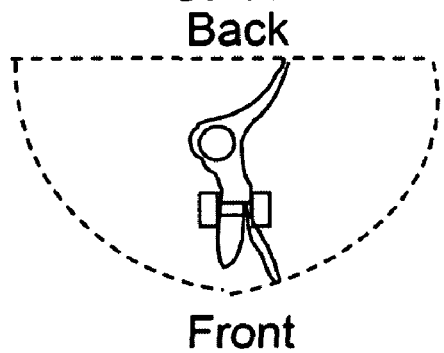
FIG. 114 is a diagrammatic plan view from the bottom of the stomach of FIG. 112 with a fastener plicating anterior stomach tissue according to a first method of the invention.

In comparison, before plication occurs, the second plication method has the posts 32, 34 of the male part 12 enter the GEJ tissue in the anterior (front) of the esophagus 414. Then, the instrument 200, 2000 is torqued counter-clockwise with respect to FIG. 112 until the jaws 226, 228 reach the position illustrated in FIG. 115, for example. As shown by the striped area in FIG. 115, when the jaws 226, 228 grasp tissue after torqueing/twisting the end effector 202, 702, 802, the area of GEJ tissue that becomes available for the plication is large in comparison to the prior method and is almost half the circumference of the esophagus 414, to wit, almost 180°. FIG. 116 illustrates a fastener implanted with the jaw positions shown in FIG. 115. Both extents of the tissue fold 4164 on either side of the esophagus 414 and all of the tissue therebetween is incorporated within the final plicated tissue.

There have been described and illustrated herein several embodiments of fasteners, instruments, systems, and methods for the endoluminal treatment of gastroesophageal reflux disease (GERD). While particular embodiments of the invention have been described, it is not intended that the invention be limited thereto, as it is intended that the invention be as broad in scope as the art will allow and that the specification be read likewise. For example, while particular preferred dimensions have been provided for both elements of the instrument and fastener, as well as cross-sectional areas of the system, it is appreciated that the system and its elements may have different relative sizes. For example, the cross-sectional areas can be decreased further if a pediatric endoscope (4 to 6 mm) is used. Also, while a "looking back" instrument has been disclosed particularly for fastener application designed to treat GERD, it is appreciated that a "forward looking" straight instrument with similar jaw assembly can be used to apply the fastener for treatments of other conditions, e.g., obesity, ulceration, stomach cancer, implantation of pH measurement or monitoring devices, feeding tubes, etc. Moreover, a straight device can be smaller in diameter and be operated through a working channel of an endoscope. Furthermore, the visualization apparatus of an endoscope may be incorporated directly into the device, thus eliminating or augmenting the use of a traditional endoscope. It will, therefore, be appreciated by those skilled in the art that yet other modifications could be made to the provided invention without deviating from its spirit and scope as so claimed.

We claim:

1. A surgical fastener with a safety position, the fastener comprising:
   a lower base having:
      first and second piercing posts each having a fixed end and a coupling end;
      a first base portion fixedly-attached to the first piercing post at the fixed end thereof;
      a second base portion fixedly-attached to the second piercing post at the fixed end thereof;
      a hinge foldably coupling the first base portion to the second base portion and having a longitudinal axis; and
      a bias device imparting a bias force on at least one of the first base portion and the second base portion in a direction toward the other and substantially perpendicular to the longitudinal axis of the hinge; and
   an upper fastening portion operable to receive and selectively couple the coupling ends of the at least two piercing posts; and the lower base having:
      a piercing position for coupling with the upper fastener portion where the first piercing post is substantially parallel to the second piercing post; and
      a folded position where a distance between the coupling end of the first piercing post and the coupling end of the second piercing post is less than a distance between the fixed end of the first piercing post and the fixed end of the second piercing post.

2. A surgical fastener with a safety position, the fastener comprising:
   a lower base having:
      first and second piercing posts each having a fixed end and a coupling end;
      a first base portion fixedly-attached to the first piercing post at the fixed end thereof;
      a second base portion fixedly-attached to the second piercing post at the fixed end thereof;
      a hinge foldably coupling the first base portion to the second base portion and having a longitudinal axis; and
      a bias device imparting a bias force on at least one of the first base portion and the second base portion in a direction toward the other of the first and second base portions and substantially perpendicular to the longitudinal axis of the hinge; and
      a receiving portion operable to receive and selectively couple the coupling ends of the first and second piercing posts.

3. The surgical fastener assembly according to claim 2, wherein the base further comprises:
   a piercing position for coupling with the receiving portion where the first piercing post is substantially parallel to the second piercing post; and
   a folded position where a distance between the coupling end of the first piercing post and the coupling end of the second piercing post is less than a distance between the fixed end of the first piercing post and the fixed end of the second piercing post.

4. The surgical fastener assembly according to claim 2, further comprising:
   a fixed cover portion fixedly attached to the receiving portion; and
   a slide cover portion slidably attached to the receiving portion, the slide cover portion including:
      a first position operable to engage the receiving portion with at least one of the first and second piercing posts; and
      a second position operable to disengage the receiving portion from the at least one of the first and second piercing posts.

5. The surgical fastener assembly according to claim 4, further comprising:
   an unlocking member with a first end physically coupled to the slide cover portion and operable to move the slide cover portion in an unlocking direction to decouple the receiving portion from the at least one of the first and second piercing posts when tension is placed on the member.

6. The surgical fastener assembly according to claim 5, wherein the unlocking member has a second end physically coupled to the fixed cover portion.

7. The surgical fastener assembly according to claim 5, further comprising:
a retrieval tool including:
a shaft having a grapple at a distal end thereof; and
a cowling surrounding a portion of the shaft, shaped to house the grapple, and movable in relation to the grapple,
wherein the shaft is slidable inside and in relation to the cowling, causing a distal edge of the cowling to place a first force on the unlocking member as the grapple places a second force, opposite the first force, on the unlocking member.

8. The surgical fastener assembly according to claim 2, wherein at least one of the first and second piercing posts further comprise:
a longitudinal axis; and
a single slot substantially perpendicular to the longitudinal axis, engagable by the receiving portion, and spaced from the fixed end at a distance sufficient to prevent tissue necrosis when the fastener is applied to tissue.

9. The surgical fastener assembly according to claim 2, wherein:
the first base portion has a first tissue compression surface;
the second base portion has a second tissue compression surface;
the first piercing portion is attached to the first base portion substantially perpendicular to the first tissue compression surface; and
the second piercing portion is attached to the second base portion substantially perpendicular to the second tissue compression surface.

10. A surgical fastener assembly with a safety position, the fastener comprising:
a first base portion having:
a first tissue-compression surface; and
a first piercing post coupled to and extending from the first tissue-compression surface;
a second base portion foldably coupled to the first base portion by a hinge, the second base portion having:
a second tissue-compression surface; and
a second piercing post coupled to and extending from the second tissue-compression surface;
a bias device imparting a bias force on at least one of the first base portion and the second base portion in a direction toward the other of the first and second base portions and substantially perpendicular to a longitudinal axis of the hinge;
a receiving portion having:
a first aperture for accepting and engaging a distal end of the first piercing post; and
a second aperture for accepting a distal end of the second piercing post so that the first piercing post and the second piercing post are substantially parallel with each other.

11. The surgical fastener assembly according to claim 10, wherein:
the first piercing post has a first piercing end and a first base-attachment end;
the second piercing post has a second piercing end and a second base-attachment end; and
the first base portion and the second base portion further comprise:
a piercing position for coupling with the receiving portion where the first piercing post is substantially parallel to the second piercing post; and
a folded position where a distance between the first piercing end and the second piercing end is less than a distance between the first base-attachment end and the second base-attachment end.

12. The surgical fastener assembly according to claim 10, further comprising:
a fixed cover portion fixedly attached to the receiving portion; and
a slide cover portion slidably attached to the receiving portion, the slide cover portion including:
a first position operable to engage the receiving portion with at least one of the first and second piercing posts; and
a second position operable to disengage the receiving portion from the at least one of the first and second piercing posts.

13. The surgical fastener assembly according to claim 12, further comprising:
an unlocking member having a first end physically coupled to the slide cover portion and operable to move the slide cover portion in an unlocking direction to decouple the receiving portion from the at least one of the first and second piercing posts when tension is placed on the member.

14. The surgical fastener assembly according to claim 13, wherein the unlocking member has a second end physically coupled to the fixed cover portion.

15. The surgical fastener assembly according to claim 14, further comprising:
a retrieval tool including:
a shaft having a grapple at a distal end thereof; and
a cowling surrounding a portion of the shaft, shaped to house the grapple, and movable in relation to the grapple,
wherein the shaft is slidable inside and with respect to the cowling sufficient to cause a distal edge of the cowling to place a first force on the unlocking member as the grapple places a second force, opposite the first force, on the unlocking member.

16. The surgical fastener assembly according to claim 10, wherein the first piercing post further comprises:
a longitudinal axis; and
a single slot substantially perpendicular to the longitudinal axis, engagable by the receiving portion, and spaced from the proximal end at a distance sufficient to prevent tissue necrosis when the fastener is applied to tissue.

17. The surgical fastener assembly according to claim 10, wherein:
the first piercing post is attached to the first base portion substantially perpendicular to the first tissue-compression surface; and
the second piercing post is attached to the second base portion substantially perpendicular to the second tissue-compression surface.

18. A two-piece surgical fastener assembly, comprising:
a piercing piece having:
a piercing base having:
a first portion with a first tissue-compression surface; and
a second portion with a second tissue-compression surface;
a first piercing post having:
a first end attached to the first portion and projecting from the first tissue-compression surface; and
a second end opposite the first end and defining a slot at a predefined distance from the first tissue-compression surface;

a second piercing post having:
  a third end attached to the second portion and projecting from the second tissue-compression surface; and
  a fourth end opposite the third end;
a hinge having a hinge axis and pivotally coupling the first portion of the piercing base to the second portion of the piercing base; and
a bias device imparting a bias force on at least one of the first and second base portions in a direction toward the other of the first and second base portions and substantially perpendicular to the hinge axis; and
a coupling piece having:
  a coupling body with a third tissue-compression surface, the coupling body defining:
    a first aperture dimensioned to receive the second end and the slot; and
    a second aperture dimensioned to receive the fourth end; and
  a coupling assembly at the coupling body operable to selectively engage the slot to retain the piercing piece thereat and position the first tissue-compression surface substantially at a second predefined distance from the third tissue-compression surface.

19. The surgical fastener assembly according to claim 18, wherein:
  the fourth end defines a second slot at the predefined distance from the second tissue-compression surface;
  the second aperture is dimensioned to receive the fourth end and the second slot; and
  the coupling assembly is operable to selectively engage the second slot to retain the piercing piece thereat and position the second tissue-compression surface substantially at the second predefined distance from the third tissue-compression surface.

* * * * *